(12) United States Patent
Tsai et al.

(10) Patent No.: US 10,668,032 B2
(45) Date of Patent: Jun. 2, 2020

(54) USE OF LITHIUM BENZOATE FOR TREATING CENTRAL NERVOUS SYSTEM DISORDERS

(71) Applicant: SyneuRx International (Taiwan) Corp., New Taipei (TW)

(72) Inventors: Guochuan Emil Tsai, Pasadena, CA (US); Hong-Jung Chen, Taipei (TW); Wei-En Hsu, New Taipei (TW); Weiju Chang, New Taipei (TW); Jing-Jia Huang, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 0 days.

(21) Appl. No.: 16/040,005

(22) Filed: Jul. 19, 2018

(65) Prior Publication Data

US 2018/0318243 A1 Nov. 8, 2018

Related U.S. Application Data

(63) Continuation of application No. PCT/CN2017/088043, filed on Jun. 13, 2017.

(60) Provisional application No. 62/349,600, filed on Jun. 13, 2016.

(51) Int. Cl.
*A61K 31/192* (2006.01)
*A61P 25/00* (2006.01)

(52) U.S. Cl.
CPC ............ *A61K 31/192* (2013.01); *A61P 25/00* (2018.01)

(58) Field of Classification Search
CPC ......... A61K 31/192; A61P 25/00; A61P 25/28
See application file for complete search history.

(56) References Cited

U.S. PATENT DOCUMENTS

| | | | |
|---|---|---|---|
| 4,810,497 A * | 3/1989 | Horrobin | A61K 31/19 424/677 |
| 2007/0049565 A1 | 3/2007 | Gwag et al. | |
| 2008/0167492 A1 | 7/2008 | Hwang et al. | |
| 2010/0189818 A1 * | 7/2010 | Tsai | A61K 31/11 424/722 |
| 2012/0301551 A1 * | 11/2012 | Gwag | A61K 31/137 424/600 |
| 2012/0301552 A1 | 11/2012 | Shinagawa et al. | |
| 2013/0017274 A1 | 1/2013 | Andersen et al. | |
| 2013/0102781 A1 | 4/2013 | Bevill et al. | |
| 2013/0338199 A1 | 12/2013 | Saxena | |

FOREIGN PATENT DOCUMENTS

| | | |
|---|---|---|
| CN | 101036669 A | 9/2007 |
| CN | 105218386 A | 1/2016 |
| RU | 2582962 C1 * | 4/2016 |
| RU | 2582962 C1 | 4/2016 |
| WO | 35/14481 A1 | 6/1995 |
| WO | 2004/000786 A1 | 12/2003 |
| WO | WO 2008/055224 A2 | 5/2008 |
| WO | WO 2010/085452 * | 7/2010 |
| WO | WO 2012/030050 A2 | 3/2012 |
| WO | WO 2012/076165 A1 | 6/2012 |
| WO | WO 2012/129568 A2 | 9/2012 |

OTHER PUBLICATIONS

Huang (Biomedical Reports 4, 519-522, May, 2016, published online Mar. 2016). (Year: 2016).*
Faldu et al. (IJRPC 2012, 2(4), p. 921-925) (Year: 2012).*
ISGLI, https://www.igsli.org/general-information-on-lithium/adverse-effects-of-lithium-salts.html, 2018 (Year: 2018).*
Gribkoff et al. Neuropharmacology, 2017 (Year: 2017).*
Bak et al., The co-crystal approach to improve the exposure of a water-insoluble compound: AMG 517 sorbic acid co-crystal characterization and pharmacokinetics. J Pharm Sci. Sep. 2008;97(9):3942-56. doi: 10.1002/jps.21280.
Butterhof et al., Influence of Cation Size on the Co-crystallisation of Benzoic Acid with Different Benzoates. J Inorganic General Chemistry. 2013;308-311.
Smith et al., Improving lithium therapeutics by crystal engineering of novel ionic cocrystals. Mol Pharm. Dec. 2, 2013;10(12):4728-38. doi:10.1021/mp400571a. Epub Nov. 18, 2013.
Mahoney, Douglas J., et al.; "Effects of High-Intensity Endurance Exercise Training in the G93A Mouse Model of Amyotrophic Lateral Sclerosis"; Muscle and Nervemuscle; vol. 29, No. 5; May 1, 2004; pp. 656-662.

* cited by examiner

*Primary Examiner* — Umamaheswari Ramachandran
(74) *Attorney, Agent, or Firm* — Polsinelli PC

(57) ABSTRACT

Methods for treating central nervous system (CNS) disorders or attenuating pain with a lithium benzoate compound.

22 Claims, 43 Drawing Sheets

A.

A.

D.

E.

F.

G.

H.

A.

A.

A.

B.

A.

USE OF LITHIUM BENZOATE FOR TREATING CENTRAL NERVOUS SYSTEM DISORDERS

RELATED APPLICATIONS

This application is a continuation of, and claims priority under 35 U.S.C. § 120 to, international PCT Application No. PCT/CN2017/088043, filed Jun. 13, 2017, which claims priority under 35 U.S.C. § 119(e) to U.S. Provisional Application No. 62/349,600, filed Jun. 13, 2016, the entire contents of each of which are hereby incorporated by reference herein.

BACKGROUND OF THE INVENTION

The central nervous system (CNS) includes the brain and spinal cord. The CNS is vulnerable to various disorders, which may be caused by various factors, including trauma, infections, degeneration, structural defects and/or damages, tumors, blood flow disruption, and autoimmune disorders. Symptoms of a CNS disorder would depend on the area of the nervous system that is involved and the cause of the disorder.

The development of effective therapies for CNS disorders has lagged behind other therapeutic areas due to the complexity of such disorders and the lack of efficient technology for delivering therapeutic agents through the blood-brain barrier. As such, it is of great interest to develop new treatment approaches for CNS disorders.

SUMMARY OF THE INVENTION

The present disclosure is based at least in part on the unexpected results that lithium benzoate exhibited protective effects in various in vitro and in vivo CNS disease models. For example, lithium benzoate successfully rescued neuron toxicity induced by 3-nitropropionic acid (3-NP), which is known to induce mitochondria dysfunction, oxidative stress, and reactive oxygen species overproduction; enhanced spare respiratory capacity for mitochondria function, which plays an important role in various CNS disorders; ameliorated disease progression in an amyotrophic lateral sclerosis (ALS) animal model; protected neurons from oxygen and glucose deprivation; reduced cell death and behavior disability from toxicity induced by 1-methyl-4-phenyl-1,2,3,6-tetrahydropyridine (MPTP) either alone, or in combination with 3-NP; and protected neuron damages caused by amyloid-β peptides. Further, lithium benzoate was observed unexpectedly to alleviate pain. Finally, lithium benzoate unexpectedly showed better pharmacokinetic features and therapeutic efficacies as compared with sodium benzoate and lithium chloride in combination.

Accordingly, one aspect of the present disclosure features a method for treating a central nervous system (CNS) disease, the method comprising administering to a subject in need thereof an effective amount of a lithium benzoate compound, which may be formulated into a composition further comprising a carrier. In some examples, the composition may be a pharmaceutical composition, a medical food, or a health food, which may further comprise a pharmaceutically acceptable carrier.

In some embodiments, the CNS disease is a neurodegenerative disease, including, but not limited to, the neurodegenerative disease is Huntington's disease, multiple system atrophy (MSA), seizure-associated neurotoxicity, Parkinson's disease, mitochondrial dysfunctions-induced CNS disorders, mitochondrial myopathy encephalomyopathy lactic acidosis stroke-like symptoms (MELAS), neuropathy ataxia retinitis pigmentosa and ptosis (NARP), myoneurogenic gastrointestinal encephalopathy (MNGIE), Leber hereditary optic neuropathy (LHON), Leigh syndrome, Alzheimer's disease, amyotrophic lateral sclerosis (ALS), myoclonic epilepsy, multiple sclerosis, ischemia stroke, vascular dementia, traumatic brain injury, spinal cord injury, Down syndrome, Lewy body dementia (LBD), sporadic inclusion body myositis (sIBM), or sporadic cerebral amyloid angiopathy (CAA), frontotemporal dementia (FTD), fragile X syndrome (FXS), periventricular leukomalacia, Friedreich's Ataxia, Gaucher disease, subarachnoid hemorrhage, perinatal hypoxic ischemic encephalopathy, progressive supranuclear palsy (PSP), intracranial hypertension, sporadic Creutzfeldt-Jacob disease, tardive dyskinesia, Rett syndrome, lateral sclerosis, hereditary spastic paraparesis, progressive bulbar palsy, spinal muscular atrophy, or X-linked spinobulbar muscular atrophy (Kennedy disease).

In some embodiments, the CNS disease is associated with oxidative stress, reactive oxygen species over-production, or both. Examples include, but are not limited to, periventricular leukomalacia, Friedreich's Ataxia, Gaucher disease, subarachnoid hemorrhage, perinatal hypoxic ischemic encephalopathy, progressive supranuclear palsy (PSP), intracranial hypertension, sporadic Creutzfeldt-Jacob disease, tardive dyskinesia, Rett syndrome, or a motor neuron disease (e.g., ALS, primary lateral sclerosis, hereditary spastic paraparesis, progressive bulbar palsy (some have SOD1 mutation), spinal muscular atrophy, or X-linked spinobulbar muscular atrophy (Kennedy disease)).

In some embodiments, the subject is a human patient having a genetic defect associated with motor neuron function. In one example, the human patient has a mutated superoxide dismutase 1 (SOD1) gene. In other examples, the subject is a human patient having mitochondrial dysfunction. Alternatively, or in addition, the subject is a human patient having or suspected of having the CNS disease. In some examples, the subject is on another CNS disease treatment.

In another aspect, the present disclosure features a method of alleviating pain in a subject, the method comprising administering to a subject in need thereof an effective amount any of the lithium benzoate compound as described herein (e.g., lithium benzoate or LiBen), which may be formulated into a composition (e.g., a pharmaceutical composition, a medical food, or a health food) that further comprises a carrier, e.g., a pharmaceutically acceptable carrier. The subject may be a human patient suffering acute pain, chronic pain, neuropathic pain, complex regional pain syndrome, or pain caused by diabetic neuropathy, inflammation, or osteoporosis. In some examples, the subject is on another anti-pain treatment.

In any of the methods described herein, the subject may be administered the lithium benzoate compound at about 5 to about 150 mg/kg, e.g., at about 15 to about 140 mg/kg; at about 25 to about 130 mg/kg; at about 35 to about 120 mg/kg; at about 45 to about 110 mg/kg; at about 55 to about 100 mg/kg; at about 65 to about 90 mg/kg; or at about 75 to about 80 mg/kg. Alternatively, or in addition, the subject can be administered the lithium benzoate compound at a frequency of four times a day to one time a month. The lithium benzoate compound, which may be formulated into a pharmaceutical composition, may be administered by a systemic route, e.g., oral administration or parenteral administration.

Also within the scope of the present disclosure are (i) pharmaceutical compositions for use in treating the target CNS disorders as described herein or for alleviating pain, the pharmaceutical composition comprising a lithium benzoate compound (e.g., lithium benzoate) and a pharmaceutically acceptable carrier; and (ii) uses of a lithium benzoate compound such as lithium benzoate for manufacturing a medicament for use in treating any of the target CNS diseases or alleviating pain.

The details of one or more embodiments of the invention are set forth in the description below. Other features or advantages of the present invention will be apparent from the following drawings and detailed description of several embodiments, and also from the appended claims.

Figure 15:
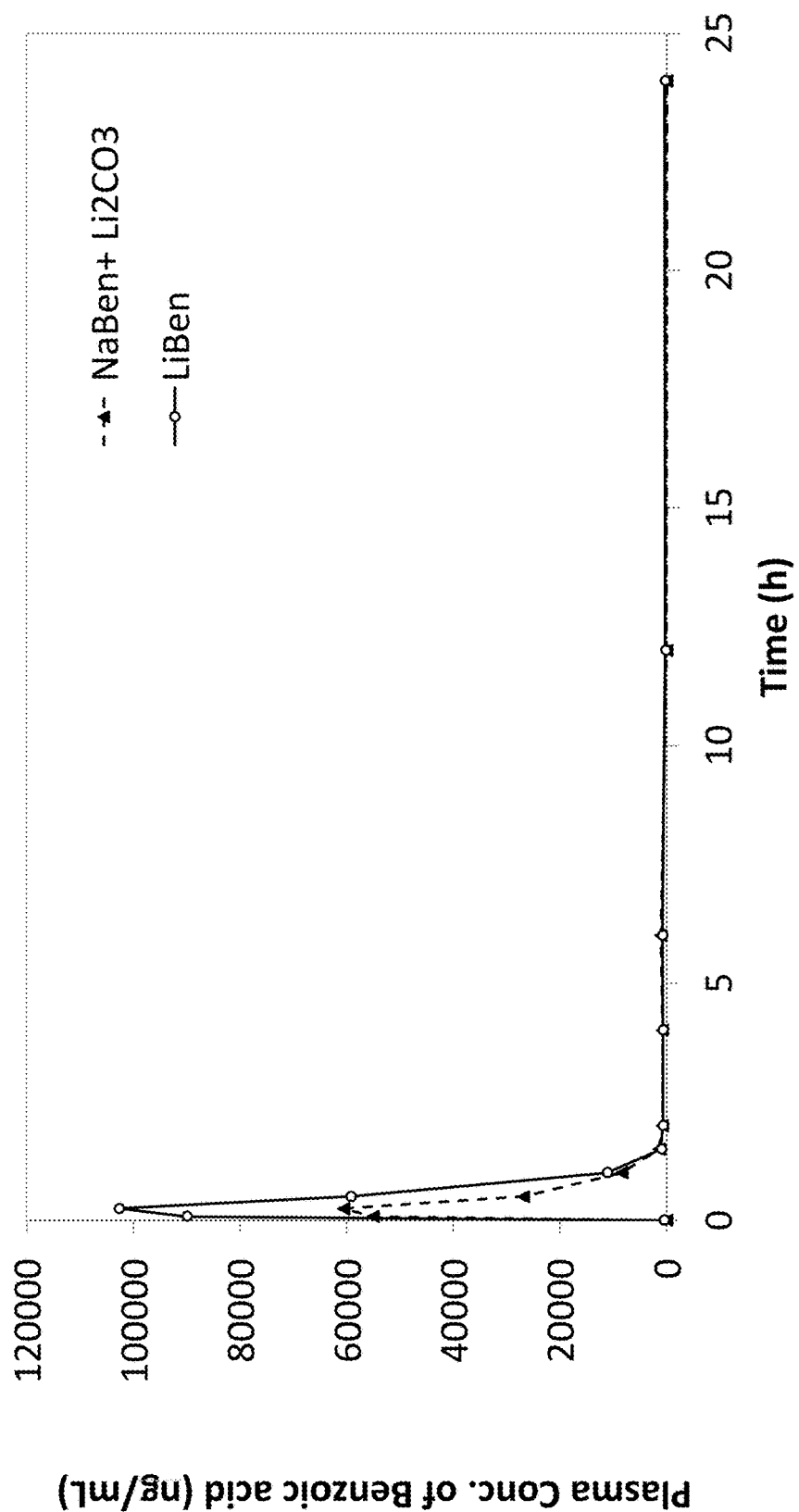
Figure 15:
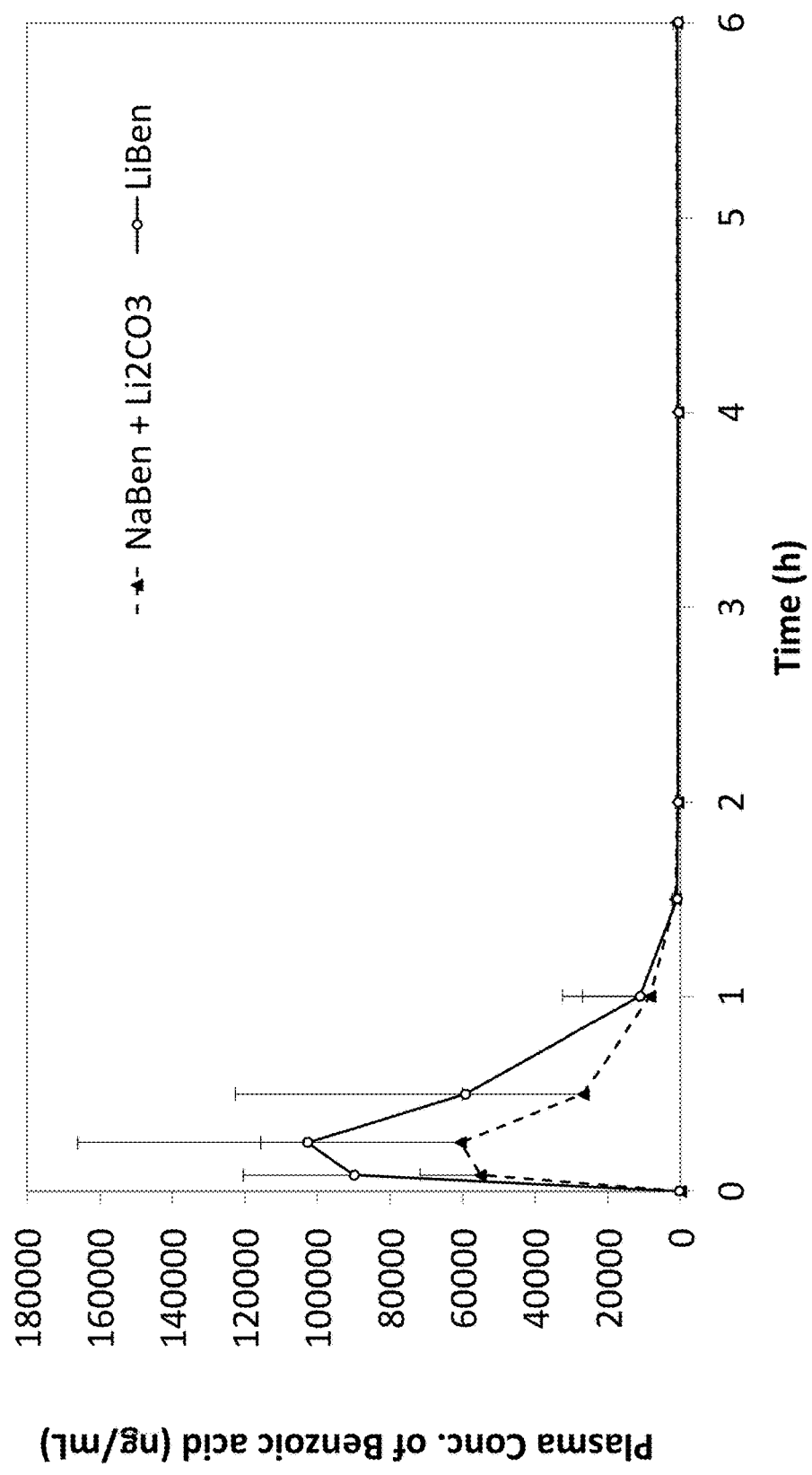

FIG. 15 includes diagrams showing line charts of plasma concentration-time curve of benzoic acid. A: a chart showing plasma concentration of benzoic acid from 0 min to 1440 min. B: a chart showing plasma concentration of benzoic acid from 0 min to 360 min. Lithium benzoate gives rise higher benzoate concentration than equimolar combination of lithium carbonate and sodium benzoate.

Figure 16:
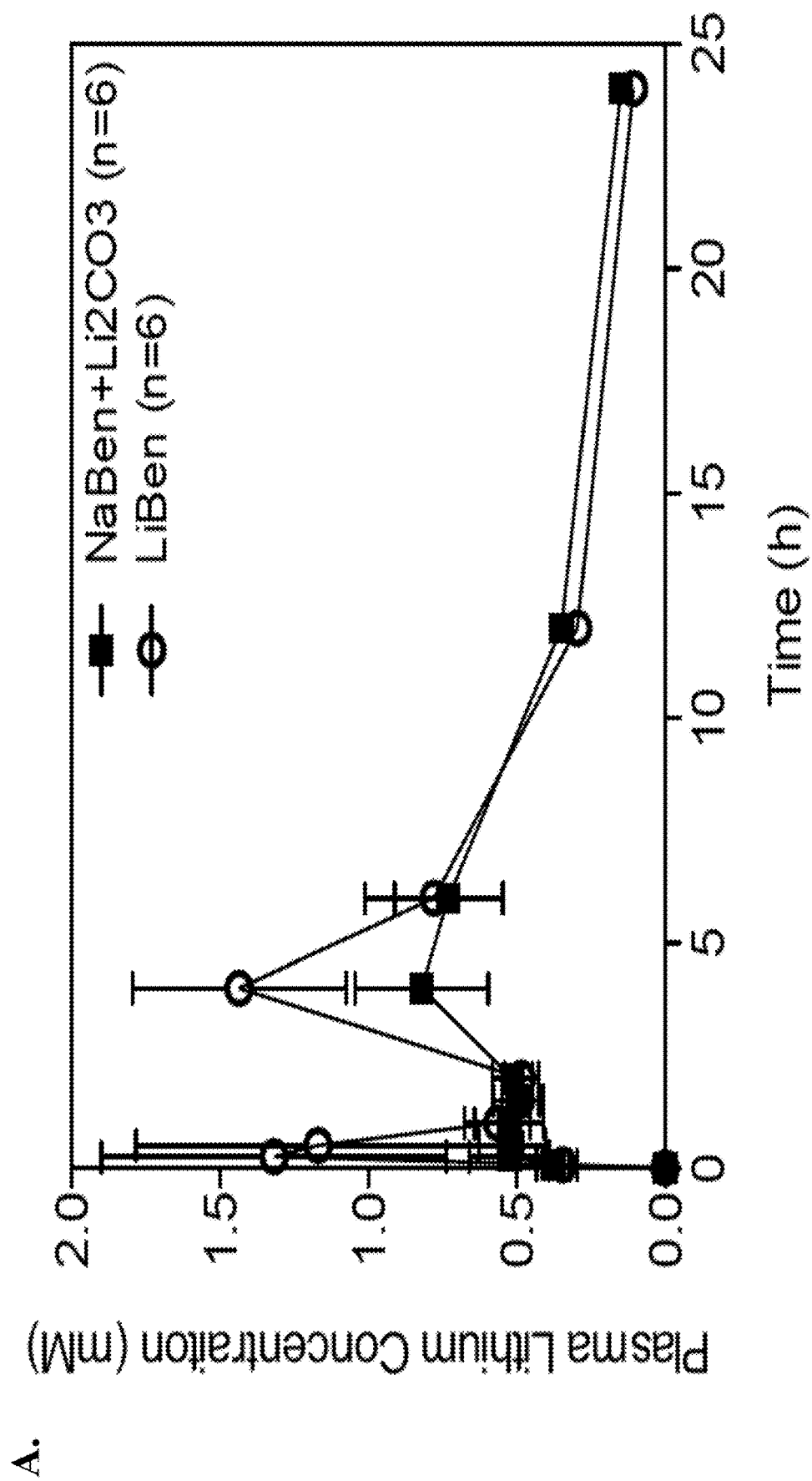
Figure 16:
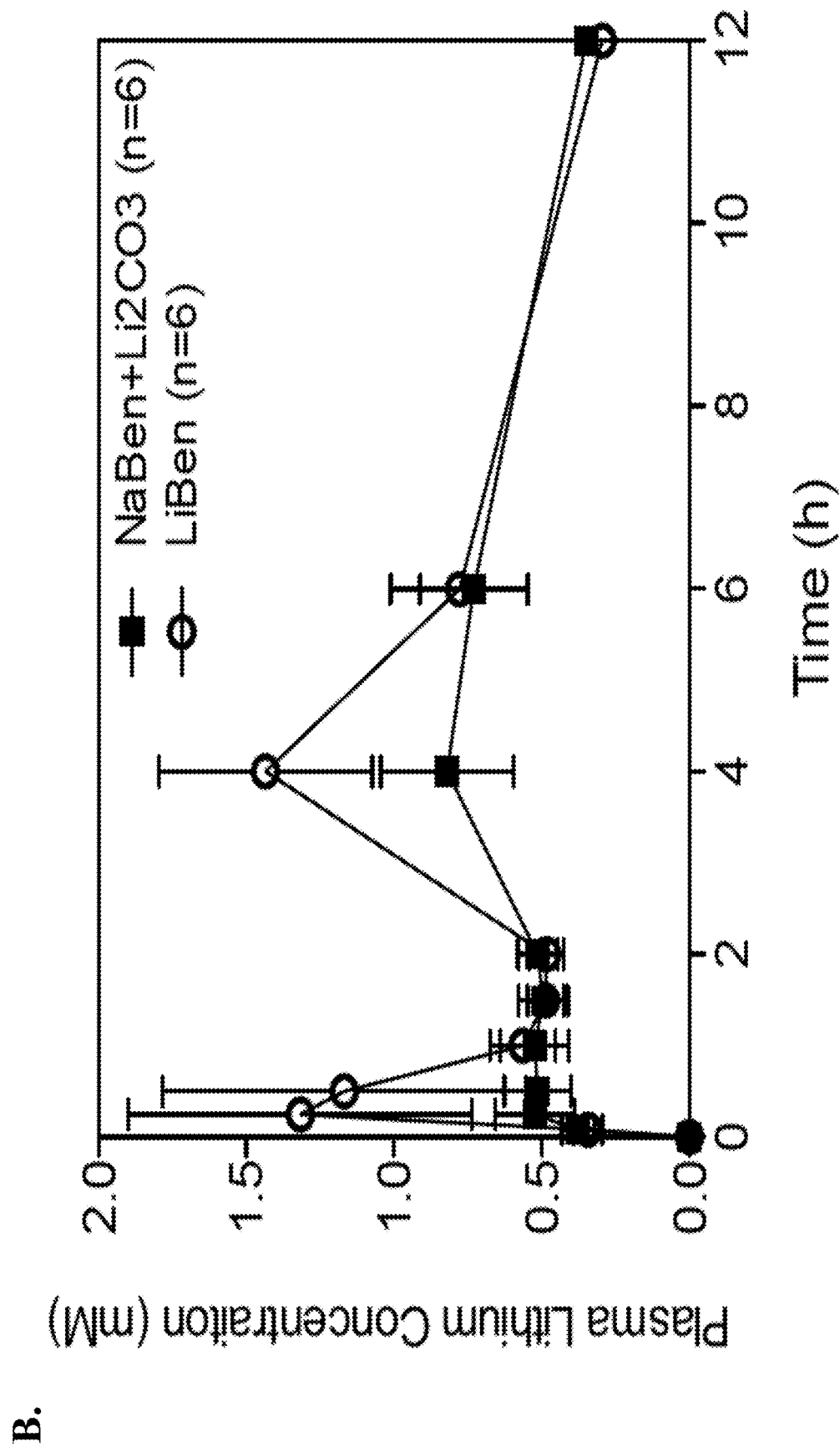

FIG. 16 includes plasma concentration-time curves of lithium. A: a chart showing plasma concentration of benzoic acid from 0 min to 1440 min. B: a chart showing plasma concentration of benzoic acid from 0 min to 720 min. Lithium benzoate gives rise higher lithium concentration than equimolar combination of lithium carbonate and sodium benzoate at several time points.

Figure 17:
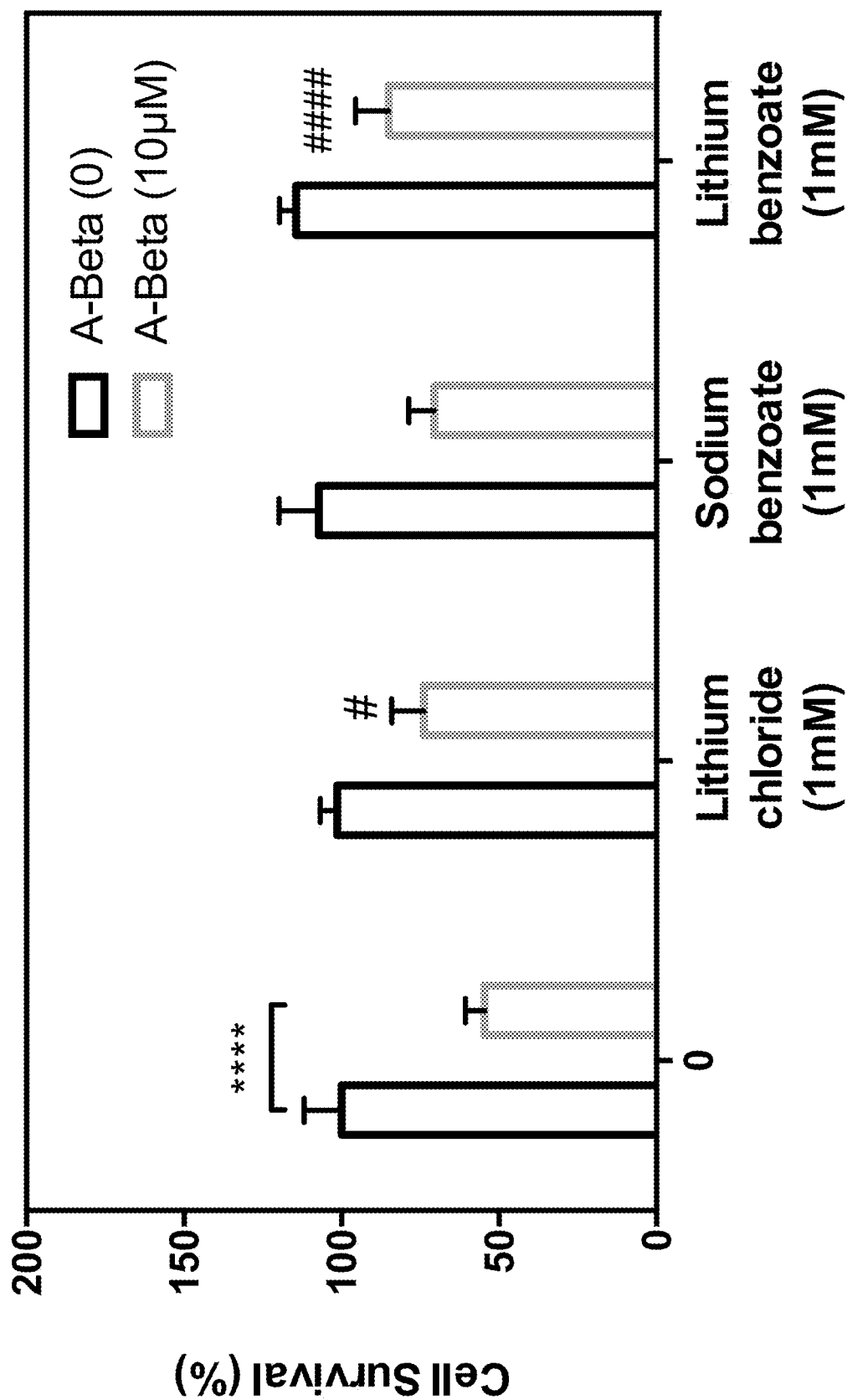

FIG. 17 is a bar graph of an MTT assay showing that, after Aβ25-35 treatment, LiCl and LiBen significantly increased the percentages of cell survival as compared to a control group. LiBen treatment has better protection than LiCl.

Figure 18:
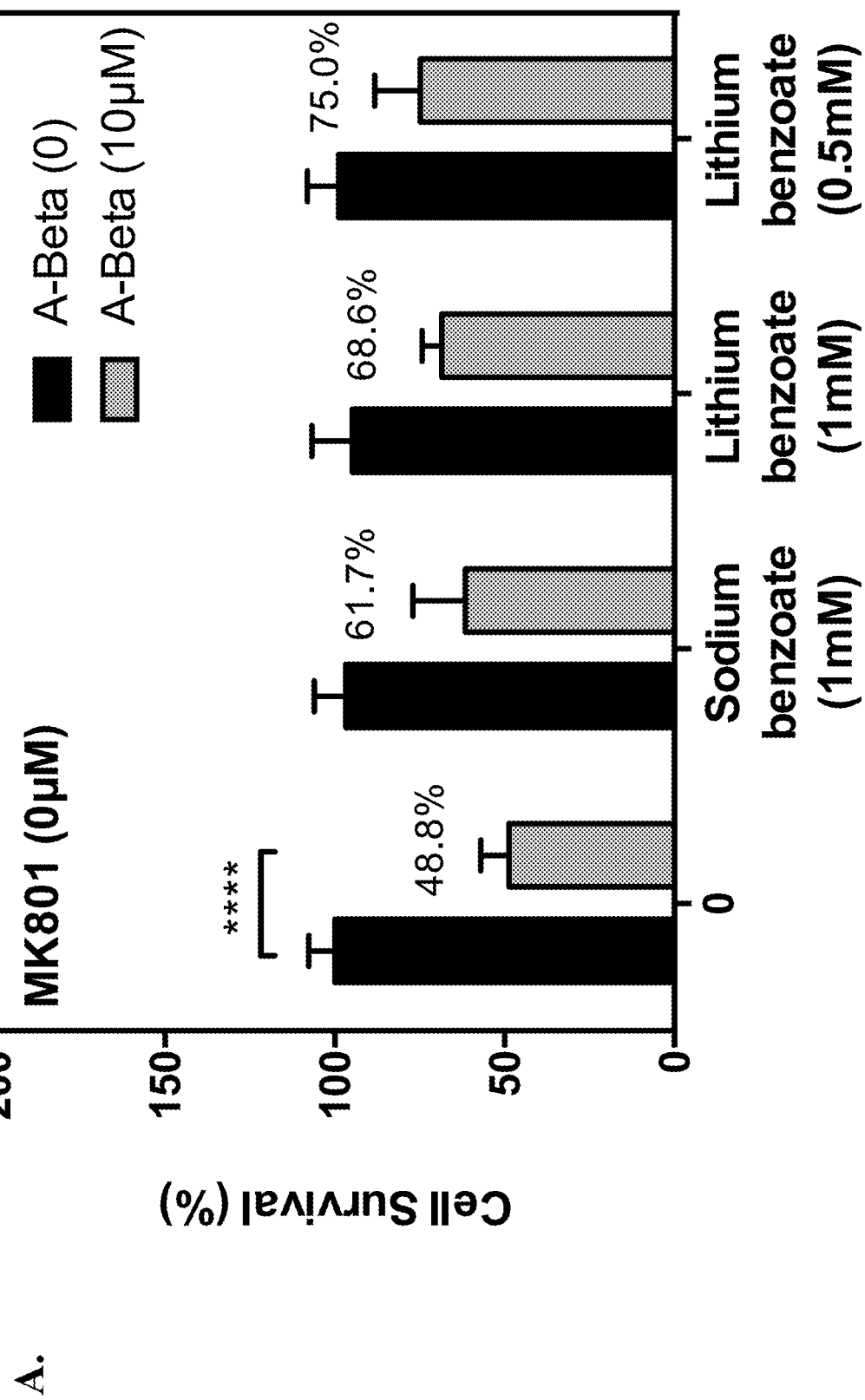
Figure 18:
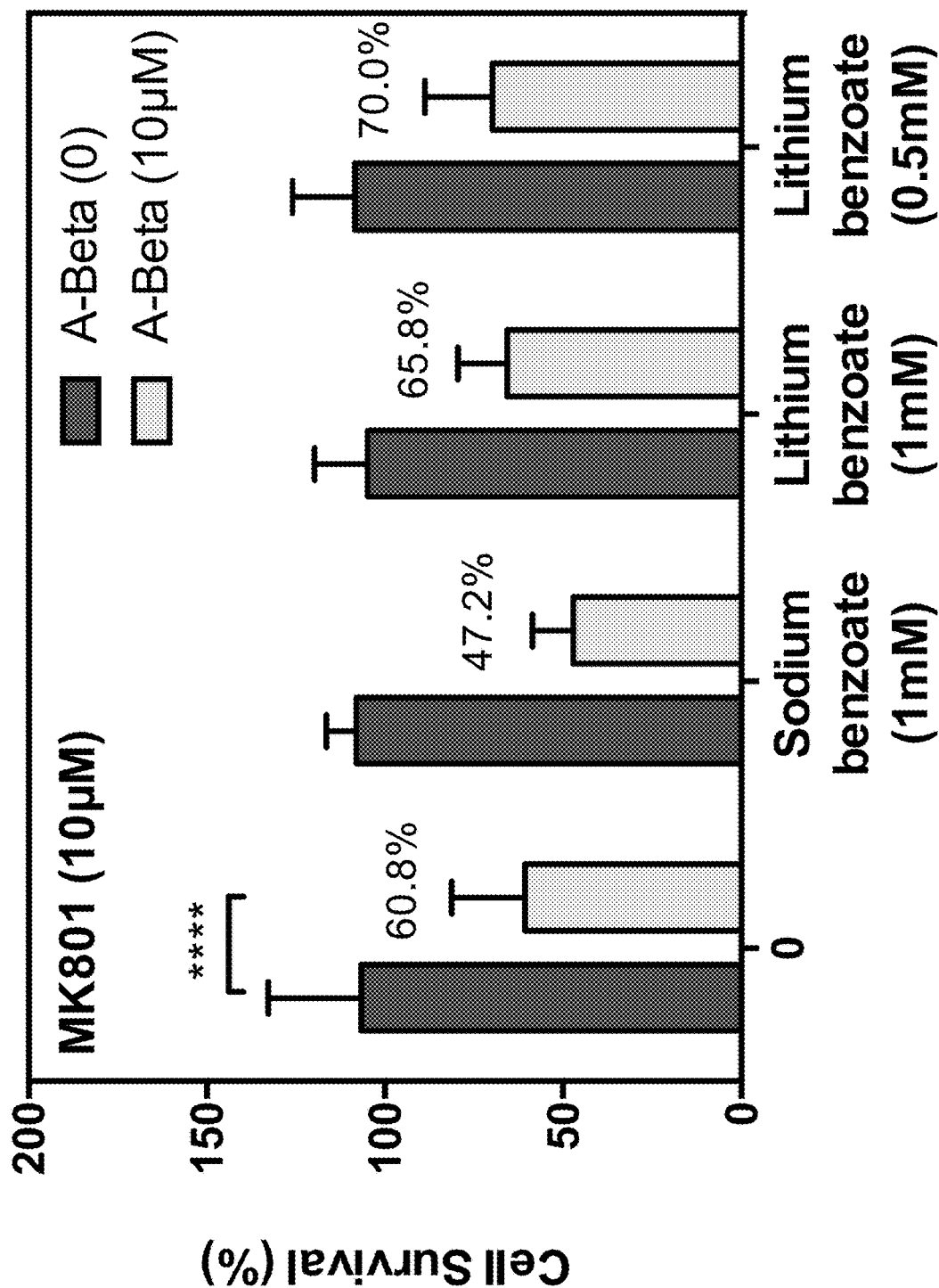

FIG. 18 includes bar graphs of MTT assays showing that decreased cell survival percentages would only be observed in the NaBen treatment group when MK801 blocked NMDA receptor whereas the MK801 treatment did not change the protection effects of lithium benzoate. A: a chart showing plasma lithium concentration in the absence of MK801 treatment (0 μM). B: a chart showing plasma lithium concentration in the presence of MK801 at 10 μM. While the effect of NaBen can be blocked by an NMDA antagonist, the effect of lithium benzoate is not affected by an NMDA antagonist.

Figure 19:
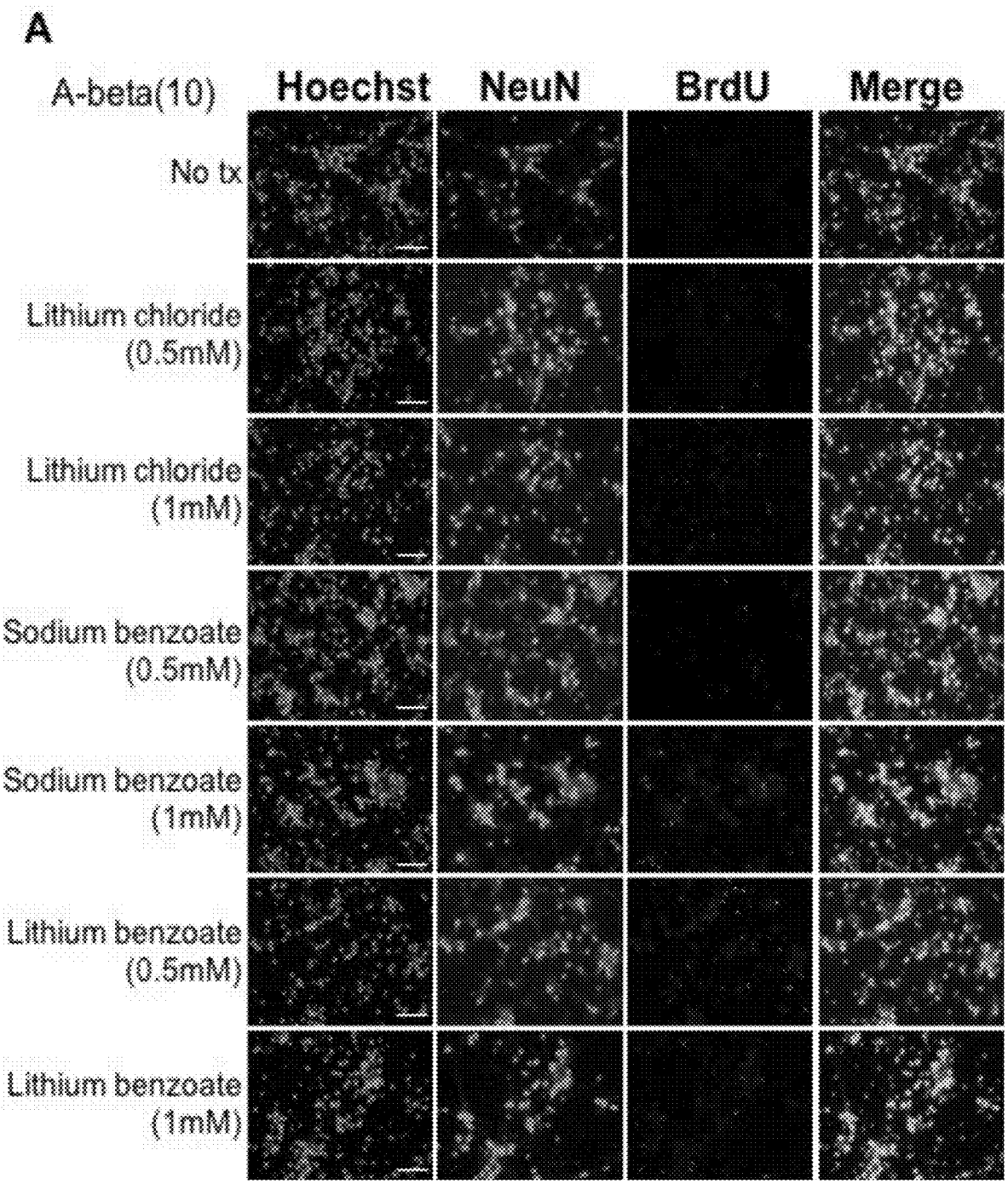
Figure 19:
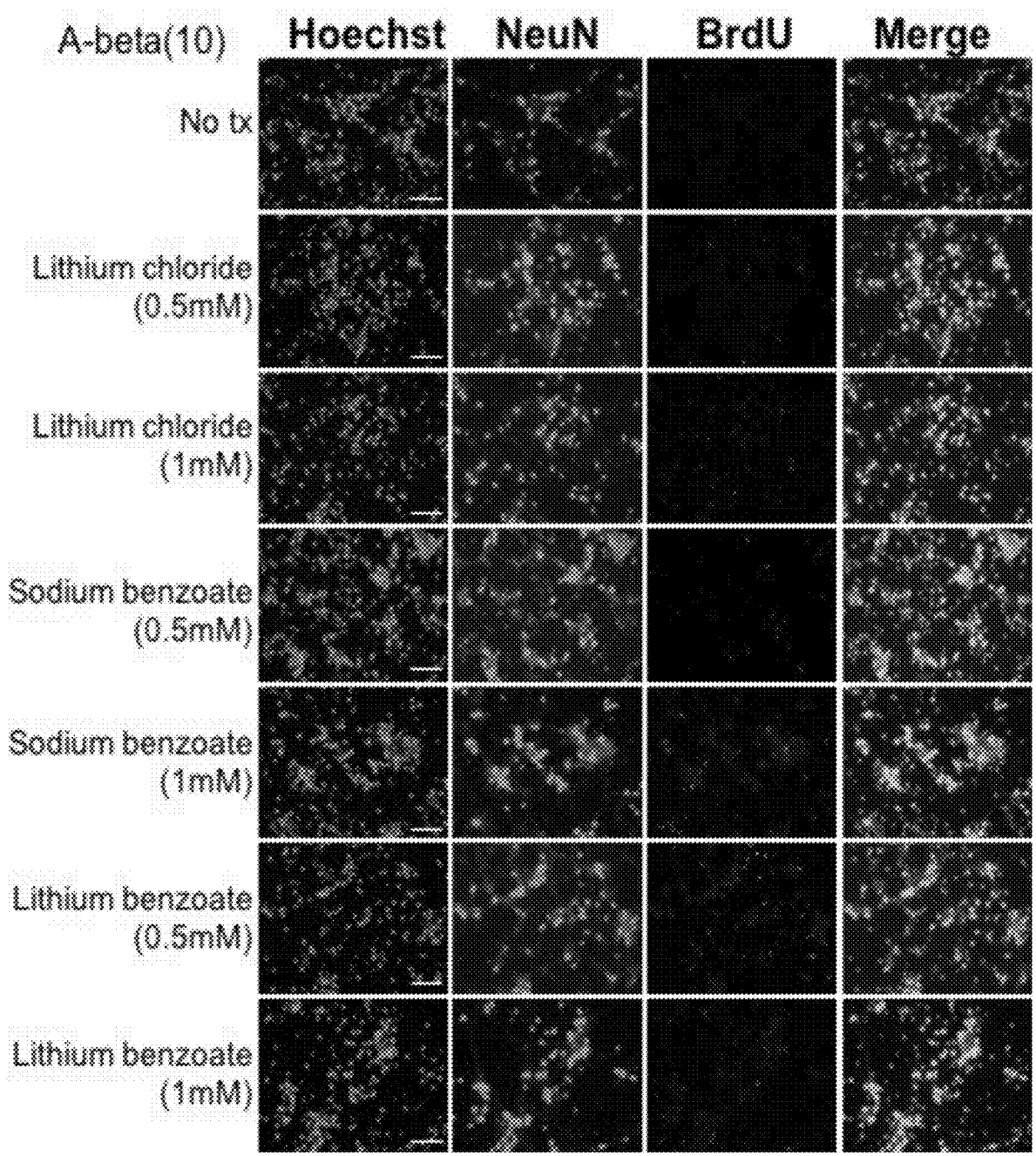
Figure 19:
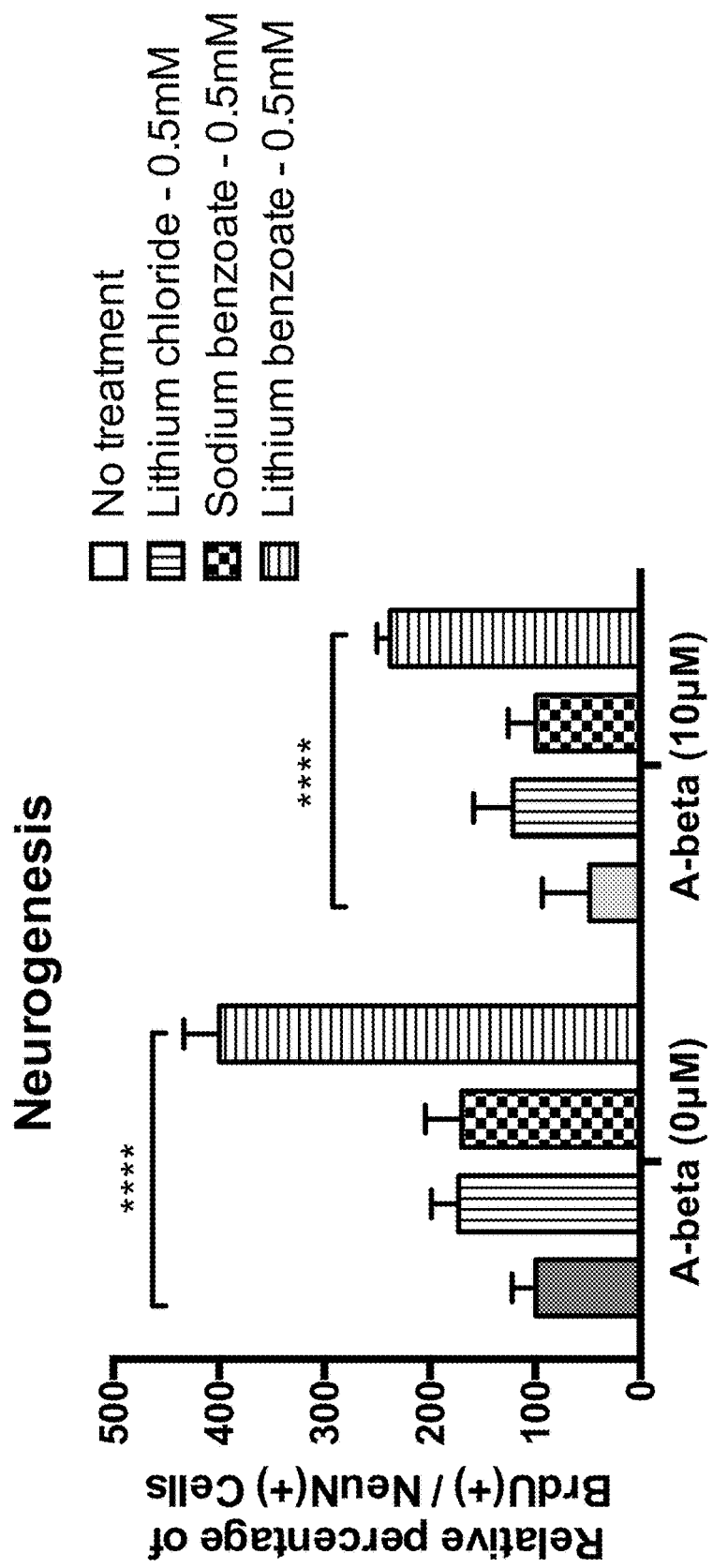

FIG. 19 includes diagrams showing that lithium benzoate enhanced neurogenesis in primary cortical culture. A and B: the immunocytochemistry assays showing Hoechst, NeuN and BrdU staining cells. Increased numbers of BrdU(+)/NeuN(+) cells were observed in LiCl/NaBen/LiBen-treated cortical cells compared to no treatment group. C: a bar graph of quantitating the results of A and B. **** indicates p<0.0001. LiBen has much stronger neurogenesis than LiCl and NaBen.

Figure 20:
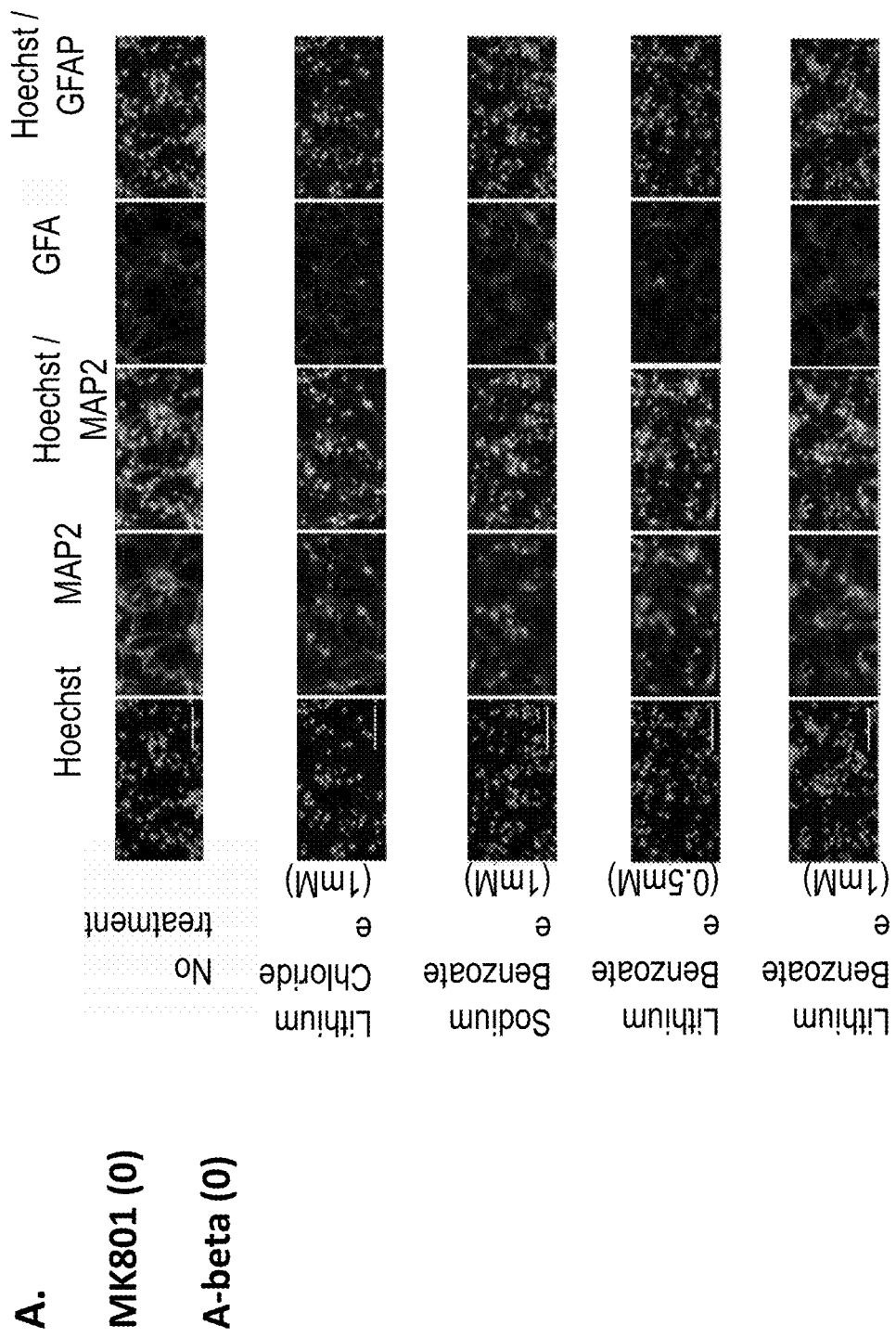
Figure 20:
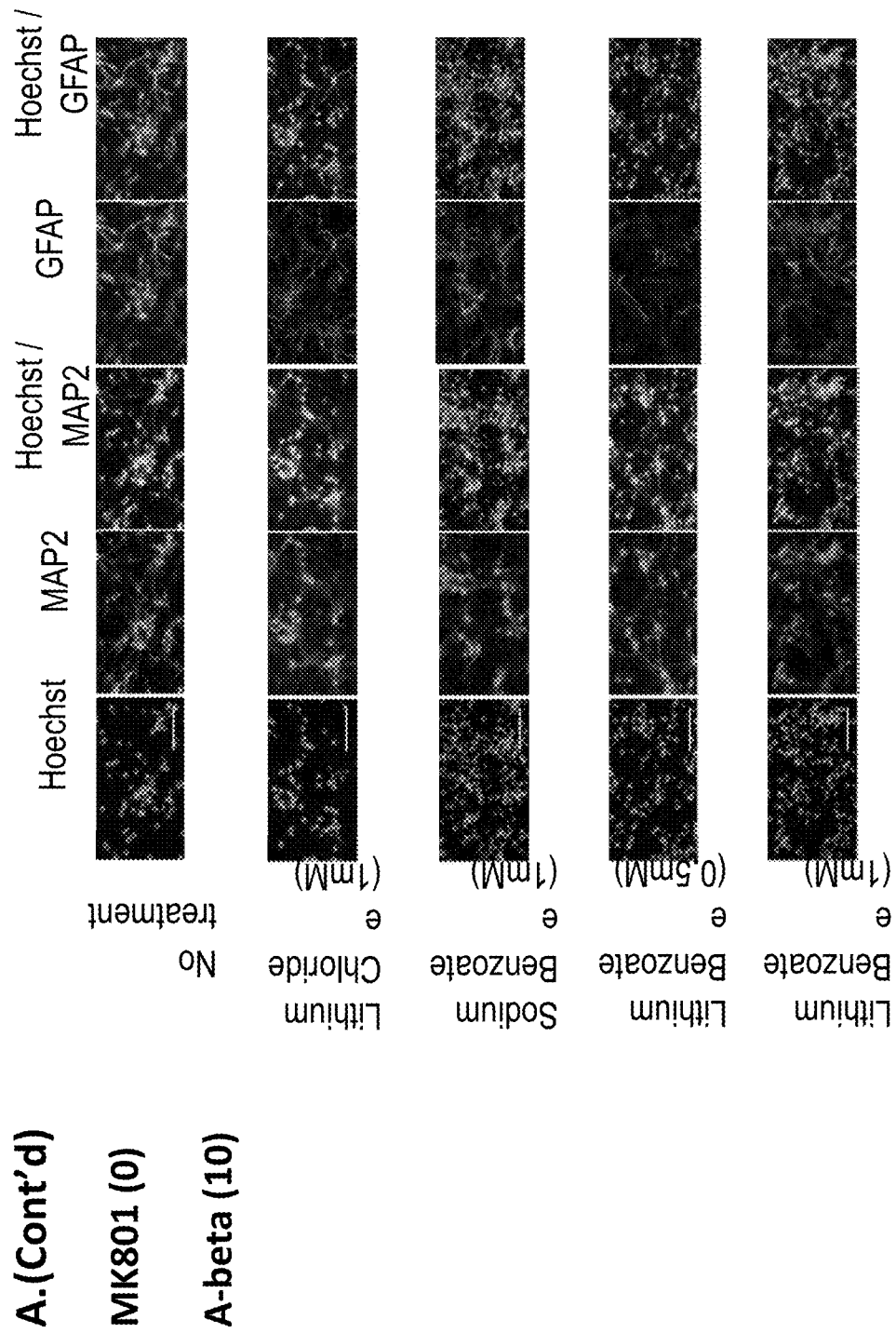
Figure 20:
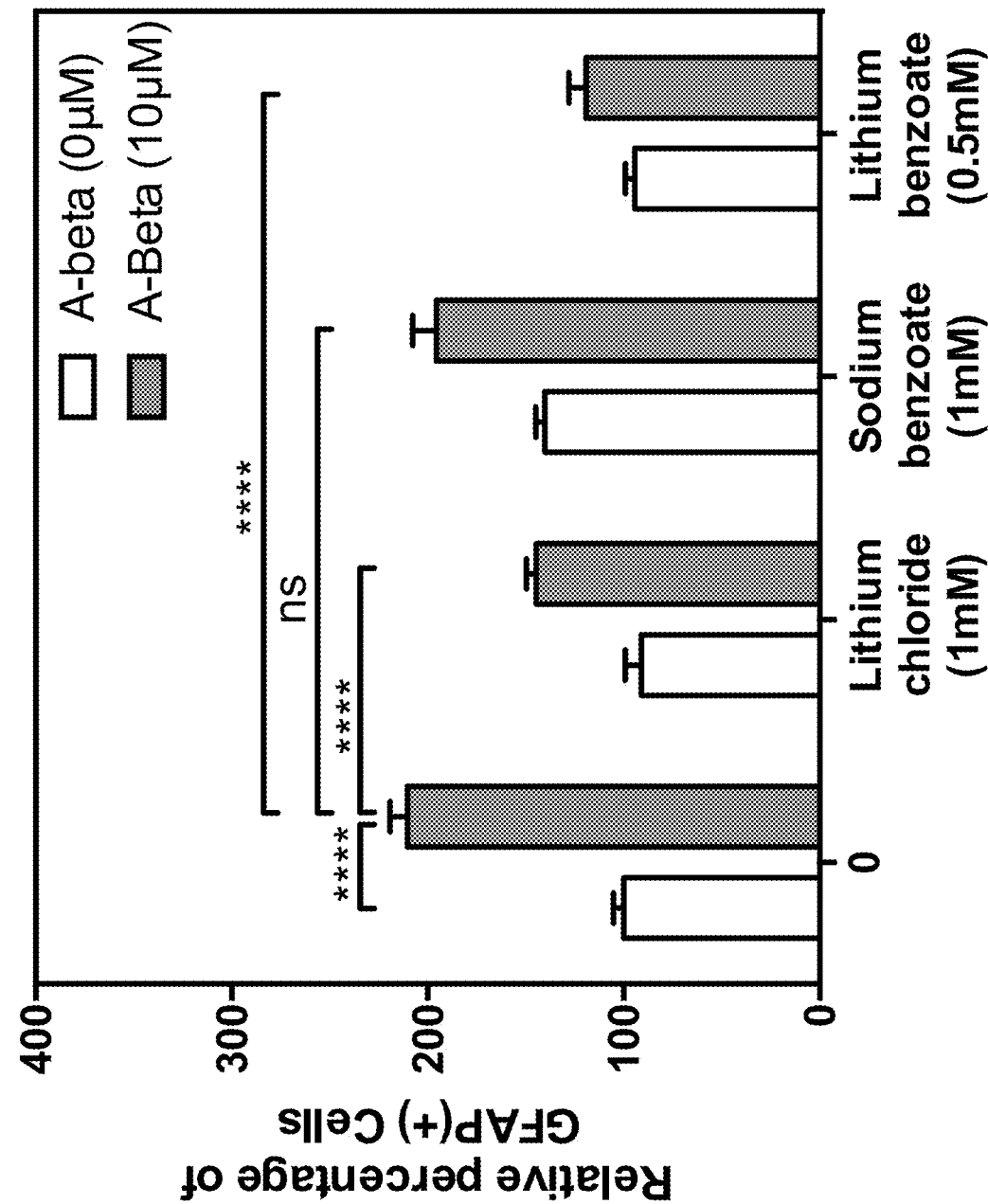

FIG. 20 includes diagrams showing that LiBen and LiCl significantly reduced the number of GFAP(+) cells after Aβ25-35 cytotoxicity compared to NaBen. At the same time, LiBen exhibited a better protection effect than LiCl. A: immunocytochemistry assay results. B: the bar graph of A. ****: p<0.0001.

Figure 21:
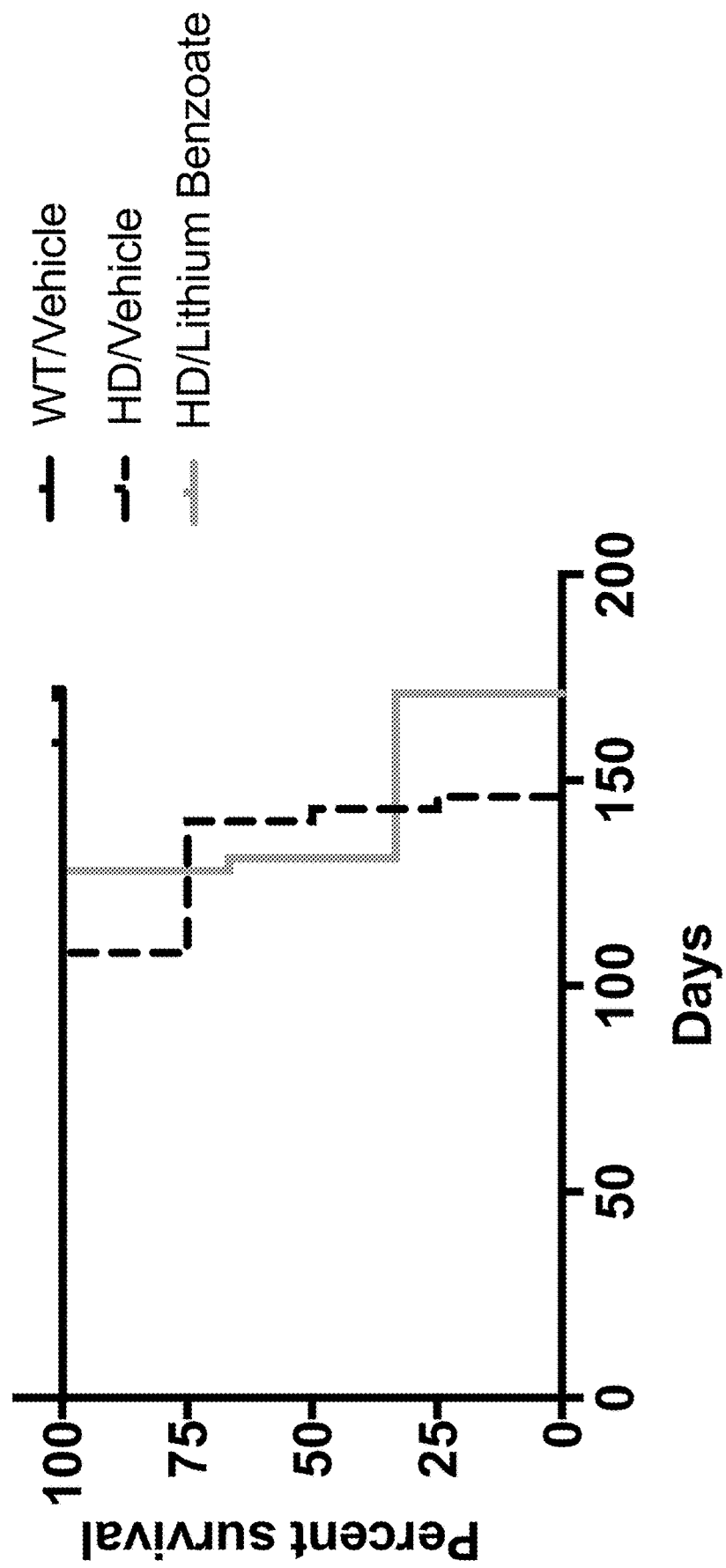

FIG. 21 is a diagram showing that lithium benzoate improves the survival rate in Huntington's disease (HD).

DETAILED DESCRIPTION OF THE INVENTION

The present disclosure is based at least in part on the unexpected results that lithium benzoate exhibited protective effects in various in vitro and in vivo CNS disease models. Lithium benzoate successfully rescued neuron toxicity induced by 3-nitropropionic acid (3-NP), which is known to induce mitochondria dysfunction, oxidative stress, and reactive oxygen species overproduction. The 3-NP model is reliable for studying Huntington's disease (HD) (Ramaswamy et al., *ILAR J.* 48(4):356-73 (2007)); fullblown MSA (Fellner et al., Front Neurosci. 10:99 (2016)); and seizure (Bhowmik et al., Br. J. Pharmacol., 167(7):1398-1414 (2012)). Also, 3-NP was known to induce oxidative stress and ROS over-production, which are known to be associated with various CNS diseases, including periventricular leukomalacia (Volpe et al., Pediatric Res. 50:553-562 (2001)), Friedreich's ataxia (Hayashi, Free Radical Biology and Medicine, 88:10-17 (2015)), Gaucher disease (de la Mata, Sci. Rep. 5: 10903 (2015)), subarachnoid hemorrhage (Ayer, Acta Neurochir Suppl. 104: 33-41 (2008)), perinatal hypoxic ischemic encephalopathy (Lai, J. Biomed Biotechnol 2011, Article ID 609813 (2011)), progressive supranuclear palsy (PSP) (Stamelou, Brain 133, 1578-1590 (2010)), intracranial hypertension (Martínez-Revelles S. Antioxid Redox Signal. 18: 51-65 (2013)), sporadic Creutzfeldt-Jacob disease (Kovacic, Curr Neuropharmacol 10:289-302 (2012)), tardive dyskinesia (Lohr J. B. CNS Drugs 17:47-62 (2003)), Rett syndrome (De Felice Neurobiology of Disease 68:66-77 (2014)), and various motor neuron diseases: ALS, primary lateral sclerosis, hereditary spastic paraparesis, progressive bulbar palsy (some have SOD1 mutation), spinal muscular atrophy, X-linked spinobulbar muscular atrophy (Kennedy disease)) (Rossi, Int'l J. Cell Biol. 2012, Article ID 908724 (2012)). Accordingly, a lithium benzoate compound as described herein would be expected to be effective in treating any of these CNS disorders.

Lithium benzoate was also observed to enhance spare respiratory capacity for mitochondria function. Mitochondria dysfunction has been found to be involved in the development of various CNS disorders, for example, Parkinson's disease (Wood-Kaczmar et al., PLoS ONE, 3, e2455 (2008), Exner, N. et al., J. Neurosci., 27:12413-12418 (2007), and Dagda, R. K. et al., J. Biol. Chem., 284: 13843-13855 (2009)), Alzheimer's disease (Baloyannis, S. J. et al., J. Alzheimers Dis., 9:119-126 (2009), Manczak, M. et al., Hum. Mol. Genet., 15:1437-1449 (2006), and Lustbader, J. W. et al., Science, 304: 448-452 (2004)), HD (Bossy-Wetzel, et al., Trends. Neurosci., 31:609-616 (2008)), ALS (Menzies et al., Brain, 125:1522-1533 (2002) and Cozzolino, M., et al., Mol. Cell. Neurosci. 2012), myoclonic epilepsy (Greaves L C et al., J Pathol., 226:274-86 (2012)), and multiple sclerosis (Morris et al., BMC Medicine, 13:68 (2015)). Accordingly, a lithium benzoate compound as described herein would be expected to benefit the treatment of such CNS disorders via reducing oxidative stress and/or ROS overproduction.

Indeed, lithium benzoate was found to ameliorate disease progression in an amyotrophic lateral sclerosis (ALS) animal model having SOD1*G93A mutation, which account for about 20% of familial ALS (Acevedo-Arozena et al., Disease Models and Mechanisms, 4: 686-700 (2011)). This result suggests that a lithium benzoate compound would be effective in treating CNS disorders involving genetic mutations associated with motor neuron diseases.

Further, lithium benzoate was found to protect neurons from oxygen and glucose deprivation, which contributes substantially to a number of CNS disorders, including ischemia stroke and vascular dementia (Bacigaluppi et al., The Open Neurology Journal, 4:34-38 (2010) and Li et al., Phytomedicine, 19 (8-9): 677-681 (2012)). Thus, a lithium benzoate compound would benefit the treatment of such CNS disorders via protective effects on oxygen and glucose deprivation.

Also, lithium benzoate reduced cell death and behavior disability from toxicity induced by 1-methyl-4-phenyl-1,2,3,6-tetrahydropyridine (MPTP) either alone, or in combination with 3-NP. MPTP-induced toxicity is a well-established model for Parkinson's disease and mitochondrial dysfunctions-induced neuron death (Langston et al., Science, 219 (4587): 979-980 (1983), and Gloria et al., J Parkinsons Dis.

2012 Dec. 26). Dual toxicity induced by MPTP and 3-NP is an established model for studying multiple system atrophy with predominant parkinsonism (MSA-P) and mitochondrial dysfunctions-induced neuron death (Fernagut et al., Experimental Neurology 185:47-62 (2004) and Fernagut et al., Neuroscience (2011)).

Moreover, lithium benzoate protected neuron damages caused by amyloid-β peptides in an animal model, indicating that a lithium benzoate compound would be effective in treating AD, Down syndrome, sporadic inclusion body myositis (sIBM), and sporadic cerebral amyloid angiopathy (CAA) (GöTz et al., Cell. Mol. Life Sci. 68:3359-3375 (2011) and Masters et al., Medical Sciences, 82:4245-4249 (1985), Mollenhauer et al, Journal of Alzheimer's Disease 24:383-391 (2011), Lu et al., Ann Neurol, 61:476-483 (2007), and Charidimou et al. 83:124e137 (2012)).

In addition, lithium benzoate was observed unexpectedly to alleviate pain, suggesting that a lithium benzoate compound would benefit alleviating of pain, such as neuropathic pain, complex regional pain syndrome, or (chronic) pain associated with diabetic neuropathy, inflammation, or osteoporosis (Wang et al., Advanced Drug Delivery Reviews 55:949-965 (2003).

In addition to the above newly discovered therapeutic effects, lithium benzoate unexpectedly showed superior pharmacokinetic features and therapeutic efficacies as compared with sodium benzoate and lithium chloride in combination. See examples below.

Accordingly, described herein are methods for treating CNS disorders such as those described herein and/or for alleviating pain using an effective amount of a composition comprising a lithium benzoate compound (e.g., lithium benzoate).

Definitions

A "lithium benzoate compound" refers to a compound of the formula:

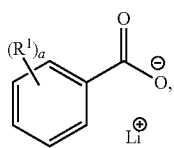

wherein $R^1$ is hydrogen, $C_{1-3}$ alkyl, halogen, —CN, —NO$_2$, —N$_3$, $C_1$-$C_3$ alkenyl, $C_1$-$C_3$ alkynyl, —OR, —NH$_2$, or —SR, R being hydrogen, halogen, —CN, —NO$_2$, —N$_3$, acyl, $C_{1-3}$ alkyl, $C_{2-3}$ alkenyl, $C_{1-3}$ alkynyl; and a being 0, 1, 2, 3, 4, or 5. In certain embodiments, the lithium benzoate compound is

(lithium benzoate)

"$C_{1-3}$ alkyl" refers to a radical of a straight-chain or branched saturated hydrocarbon group having from 1 to 3 carbon atoms, e.g., 1 to 2 carbon atoms ("$C_{1-2}$ alkyl") or 1 carbon atom ("$C_1$ alkyl"). Unless otherwise specified, each instance of an alkyl group can be independently unsubstituted (an "unsubstituted alkyl") or substituted (a "substituted alkyl") with one or more substituents (e.g., halogen, such as F). In certain embodiments, the alkyl group is an unsubstituted $C_{1-3}$ alkyl (e.g., —CH$_3$ or —CF$_3$). "Halo" or "halogen" refers to fluorine (fluoro, —F), chlorine (chloro, —Cl), bromine (bromo, —Br), or iodine (iodo, —I).

"$C_{2-4}$ alkenyl" refers to a radical of a straight-chain or branched hydrocarbon group having from 2 to 4 carbon atoms, one or more carbon-carbon double bonds, and no triple bonds. In some examples, an C2-4 alkenyl group has 2, 3, or 4 carbon atoms. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-4}$ alkenyl. In certain embodiments, the alkenyl group is substituted $C_{2-4}$ alkenyl, e.g., substituted with a halogen such as F or Cl, or a $C_{1-3}$ alkyl such as —CH3. In an alkenyl group, a C═C double bond for which the stereochemistry is not specified

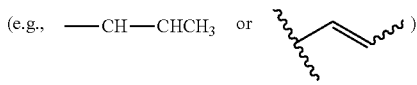

may be an (E)- or (Z)-double bond.

"$C_{2-4}$ alkynyl" refers to a radical of a straight-chain or branched hydrocarbon group having from 2 to 4 carbon atoms, one or more carbon-carbon triple bonds, and optionally one or more double bonds. In some embodiments, an alkynyl group has 2, 3, or 4 carbon atoms. Unless otherwise specified, each instance of an alkynyl group is independently optionally substituted, i.e., unsubstituted (an "unsubstituted alkynyl") or substituted (a "substituted alkynyl") with one or more substituents, e.g., halogen such as F or Cl, or a $C_{1-3}$ alkyl such as —CH3.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference.

Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, gluceptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\,alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter-ions such as halide, hydroxide, carboxylate, sulfate, phosphate, nitrate, lower alkyl sulfonate, and aryl sulfonate.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "patient" refers to a human subject in need of treatment of a disease.

The terms "administer," "administering," or "administration" refers to implanting, absorbing, ingesting, injecting, inhaling, or otherwise introducing a lithium benzoate compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of a composition comprising a lithium benzoate compound described herein refers to an amount sufficient to elicit the desired biological response, i.e., treating and/or reducing the risk of the condition. As will be appreciated by those of ordinary skill in this art, the effective amount of a lithium benzoate compound described herein may vary depending on such factors as the desired biological endpoint, the pharmacokinetics of the lithium benzoate compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a lithium benzoate compound described herein in a single dose. In certain embodiments, an effective amount is the combined amounts of a lithium benzoate described herein in multiple doses.

A "therapeutically effective amount" of a lithium benzoate compound described herein is an amount sufficient to provide a therapeutic benefit in the treatment of a condition or to delay or minimize one or more symptoms associated with the condition. A therapeutically effective amount of a lithium benzoate compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a lithium benzoate compound described herein is an amount sufficient to prevent a condition, or one or more symptoms associated with the condition or prevent its recurrence. A prophylactically effective amount of a lithium benzoate compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The terms "health food" or "health food product" refers to any kind of liquid and solid/semi-solid materials that are used for nourishing humans and animals, for alleviating at least one symptom associated with a target CNS disease as described herein or for alleviating pain or for facilitating treatment of any of the target diseases noted herein. The term "nutraceutical composition" refers to compositions containing components from food sources and conferring extra health benefits in addition to the basic nutritional value found in foods.

The term "medical food product" refers to a food product formulated to be consumed or administered enterally, including a food product that is usually used under the supervision of a physician for the specific dietary management of a target disease, such as those described herein. A "medical food product" composition may refer to a composition that is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management). The term "nutraceutical composition" refers to compositions containing components from food sources and conferring extra health benefits in addition to the basic nutritional value found in foods.

Compositions

The present disclosure provides compositions comprising a lithium benzoate compound such as lithium benzoate (LiBen) as described herein and a carrier. The lithium benzoate compound can be prepared by chemical synthesis following routine technology or obtained from a commercial vendor. In certain embodiments, the carrier is a pharmaceutically acceptable excipient. In certain embodiments, a composition described herein comprises a lithium benzoate compound described herein, and a carrier. The compositions described herein are useful in treating a target CNS disease as described herein or for alleviating pain.

In certain embodiments, the composition is a pharmaceutical composition. In certain embodiments, the composition is a nutraceutical composition. In certain embodiments, the composition is a health food. In some embodiments, the compositions described herein can be a health food or health food product, which can be any kinds of liquid and solid/semi-solid materials that are used for nourishing humans and animals, for benefiting treatment of a target CNS disease or for alleviating pain. The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product described herein, may comprise one or more edible carriers, which confer one or more of the benefits to the product as described herein. Examples of edible carriers include starch, cyclodextrin, maltodextrin, methylcellulose, carbonmethoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the health food products described herein may further include neuroprotective foods, such as fish oil, flax seed oil, and/or benzoate.

In some examples, the health food product is a nutraceutical composition, which refers to compositions containing components from food sources and conferring extra health benefits in addition to the basic nutritional value found in foods. A nutraceutical composition as described herein comprises the lithium benzoate compound described herein and additional ingredients and supplements that promote good health and/or enhance stability and bioactivity of the lithium benzoate compound.

The actions of nutraceutical compositions may be fast or/and short-term or may help achieve long-term health objectives as those described herein. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolysate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration. For oral administration, the composition can take the form of, for example, tablets or capsules, prepared by conventional means with acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the health food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate). In certain embodiments, the composition is a medical food. A medical food product is a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management). In some examples, a medical food composition described herein is not one of those that would be simply recommended by a physician as part of an overall diet to manage the symptoms or reduce the risk of a disease or condition.

Any of the medical food compositions described herein, comprising a lithium benzoate compound and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the lithium benzoate compound in the composition, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

In certain embodiments, the lithium benzoate compound described herein is provided in an effective amount in the pharmaceutical composition. In certain embodiments, the effective amount is a therapeutically effective amount (e.g., amount effective for treating and/or reducing the risk for a CNS disease or for alleviating pain). In certain embodiments, the effective amount is a prophylactically effective amount (e.g., amount effective for preventing a neuropsychiatric disorder in a subject in need thereof).

Pharmaceutical compositions described herein can be prepared by any method known in the art of pharmacology. In general, such preparatory methods include bringing the lithium benzoate compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the digestive tract, optionally, in a delayed manner. Examples of encapsulating agents which can be used include, but are not limited to, polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The lithium benzoate compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition or lithium benzoate compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or lithium benzoate compound described herein. In some embodiments, the pharmaceutical composition or lithium benzoate compound described herein provided in the first container and the second container are combined to form one unit dosage form.

In certain embodiments, a kit described herein includes a first container comprising a lithium benzoate compound or composition described herein. In certain embodiments, a kit described herein is useful in treating and/or reducing the risk for a CNS disease or pain in a subject in need thereof.

In certain embodiments, a kit described herein further includes instructions for using the lithium benzoate compound or composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating and/or reducing the risk for a neuropsychiatric disorder in a subject in need thereof. A kit described herein may include one or more additional pharmaceutical agents described herein as a separate composition.

Methods of Treatment

The present disclosure provides methods of treating, reducing the risk, or delaying the onset for a CNS disorder or pain disorders, in a subject in need thereof, the methods comprising administering to the subject an effective amount (e.g., therapeutically effective amount) of a lithium benzoate compound (e.g., LiBen) or composition comprising such, as described herein.

In certain embodiments, the CNS disorder to be treated by a lithium benzoate compound is a neurodegenerative disease, including, but not limited to, Huntington's disease (HD), multiple system atrophy (MSA), seizure-associated neurotoxicity, Parkinson's disease (PD), mitochondrial dysfunctions-induced CNS disorders, mitochondrial myopathy encephalomyopathy lactic acidosis stroke-like symptoms (MELAS), neuropathy ataxia retinitis pigmentosa and ptosis (NARP), myoneurogenic gastrointestinal encephalopathy (MNGIE), Leber hereditary optic neuropathy (LHON), Leigh syndrome, Alzheimer's disease (AD), amyotrophic lateral sclerosis (ALS), myoclonic epilepsy, multiple sclerosis, ischemia stroke, vascular dementia, traumatic brain injury, spinal cord injury, Down syndrome, Lewy body dementia (LBD), sporadic inclusion body myositis (sIBM), or sporadic cerebral amyloid angiopathy (CAA), frontotemporal dementia (FTD), fragile X syndrome (FXS), periventricular leukomalacia, Friedreich's ataxia, Gaucher disease, subarachnoid hemorrhage, perinatal hypoxic ischemic encephalopathy, progressive supranuclear palsy (PSP), intracranial hypertension, sporadic Creutzfeldt-Jacob disease, tardive dyskinesia, Rett syndrome, lateral sclerosis, hereditary spastic paraparesis, progressive bulbar palsy, spinal muscular atrophy, or X-linked spinobulbar muscular atrophy (Kennedy disease).

In some embodiments, the CNS disorder is associated with oxidative stress and/or overproduction of ROS. Examples include, but are not limited to, periventricular leukomalacia, Friedreich's ataxia, Gaucher disease, subarachnoid hemorrhage, perinatal hypoxic ischemic encephalopathy, progressive supranuclear palsy (PSP), intracranial hypertension, sporadic Creutzfeldt-Jacob disease, tardive dyskinesia, Rett syndrome, or a motor neuron disease (e.g., ALS, Huntington's disease, primary lateral sclerosis, hereditary spastic paraparesis, progressive bulbar palsy (some have SOD1 mutation), spinal muscular atrophy, or X-linked spinobulbar muscular atrophy (Kennedy disease)).

In some embodiments, the CNS disorder is associated with a genetic defect associated with a motor neuron function, for example, a mutated SOD1 gene, or a mutated huntingtin (HTT) gene. Examples include ALS, Huntington's disease, hereditary spastic paraplegia; lethal congenital contracture syndrome, primary lateral sclerosis; spinal bulbar muscular atrophy, lethal congenital contracture syndrome and spinal muscular atrophy.

In other embodiments, the CNS disorder is associated with oxygen and/or glucose deprivation, for example, brain injury. Examples include ischemic stroke and vascular dementia.

In yet other embodiments, the CNS disorder is associated with mitochondria dysfunction, e.g., Parkinson's disease, Alzheimer's disease, HD, ALS, myoclonic epilepsy, and multiple sclerosis.

In still other embodiments, the CNS disorder is associated with amyloid-β toxicity, for example, AD, Down syndrome, sporadic inclusion body myositis (sIBM), and sporadic cerebral amyloid angiopathy (CAA).

In addition, the CNS disorder can be a striatonigral degeneration diseases, e.g., MSA-P.

A lithium benzoate compound or a composition comprising such can also be used to alleviate pain in a subject in need of the treatment. For example, the subject may be suffering from a pain caused by various factors, including neuropathic pain, complex regional pain syndrome, or pain associated with diabetic neuropathy, inflammation, or osteoporosis.

Any of the methods described herein may further include administering to the subject an additional pharmaceutical agent, which can be an anti-CNS disorder agent or a pain reliever. Examples include antipsychotics selected from butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, a dopamine partial agonist, lamotrigine, memantine, tetrabenazine, cannabidiol, LY2140023, droperidol, pimozide, butaperazine, carphenazine, remoxipride, piperacetazine, sulpiride, acamprosate, and tetrabenazine; antidepressant or mood stabilizer selected from the group consisting of a fluoxetine, paroxetine, escitalopram, citalopram, seriraline, fluvoxamine, venlafaxine, milnacipram, duloxetine, mirtazapine, mianserin, reboxetine, bupropion, amitriptyline, nortriptiline, protriptyline, desipramine, trimipramine, amoxapine, bupropion, bupropion sr, s-citalopram, clomipramine, desipramine, doxepin, isocarboxazid, velafaxine xr, tranylcypromine, trazodone, nefazodone, pheneizine, lamatrogine, lithium, topiramate, gabapentin, carbamazepine, oxacarbazepine, valporate, maprotiline, mirtazapine, brofaromine, gepirone, moclobemide, isoniazid, and iproniazid; medication for improving cognition and/or inhibiting neurodegeneration selected from the group consisting of aricept, donepezil, tacrine, rivastigmine, memantine, physostigmine, nicotine, arecoline, huperzine alpha, selegiline, riluzole, vitamin C, vitamin E, carotenoids, Ginkgo biloba; pain reliever selected from hydrocodone-acetaminophen, Lyrica, tramadol, Neurontin, oxycodone, gabapentin, Percocet, OxyContin, Vicodin, Vicodin ES, Vicodin HP, methadone, Norco, Ultram, Celebrex, naproxen, naproxen sodium, oxycodone-acetaminophen, Nucynta, Dilaudid, Opana ER, morphine, MS Contin, ibuprofen, Roxicodone, etodolac, Kadian, Opana, Endocet, hydromorphone, Aleve, Ultracet, acetaminophen, tramadol-acetaminophen, hydrocodone-ibuprofen, Vicoprofen, Butrans transdermal, pregabalin oral, diclofenac potassium, acetaminophen-codeine, Tylenol-Codeine #3, Tylenol, Embeda, ketorolac, Demerol, Excedrin Migraine, Advil PM, Nucynta ER, Naprosyn, Ponstel, Prialt intrathecal, oxymorphone, Zipsor, Sprix nasal, aspirin, Methadose, Gralise, Cambia, Demerol injection, pentazocine-naloxone, Lortab Elixir, Percogesic, entanyl citrate epidural, Dolophine, Zorvolex, butorphanol tartrate nasal, Methadone Intensol, ketoprofen, meperidine, Advil, Tylenol PM Extra Strength, celecoxib, Reprexain, Xodol 10/300, Zohydro ER, fentanyl intravenous, morphine intramuscular, morphine intravenous, Dilaudid injection, Lorcet Plus, Advil Migraine, Hysingla ER, diflunisal, hydromorphone intravenous, codeine sulfate, tapentadol, Buprenex injection, methadone injection, Trezix, morphine injection, Nalfon oral, fentanyl injection, Tylenol-Codeine #4, Zamicet, ketamine injection, hydromorphone injection, magnesium salicylate, buprenorphine transdermal, Duramorph injection, mefenamic acid, Advil Liqui-Gel, Tylenol Extra Strength, ketorolac injection, Ibuprofen PM, Gralise 30-Day Starter Pack, Motrin IB, morphine intravenous, buprenorphine HCl injection, morphine rectal, meclofenamate oral, oxycodone-aspirin, ketorolac intramuscular, Anaprox DS, fentanyl in 0.9% sodium chloride intravenous, Hycet, ziconotide intrathecal, Percogesic Extra Strength, Xartemis XR, Naprelan CR, aspirin-acetaminophen-caffeine, oxymorphone injection, levorphanol tartrate, Demerol injection, hydrocodone bitartrate, nalbuphine injection, hydromorphone rectal, fentanyl HCl transdermal, methadone intravenous, Q-PAP, diphenhydramine-acetaminophen, Alka-Seltzer, meperidine injection, hydromorphone injection, Dologesic, acetaminophen rectal, dihydrocodeine-acetaminophen-caffeine, Endodan, Ibuprofen IB, Vanquish, Xodol 7.5/300, Xodol 5/300, Ofirmev intravenous, Belbuca buccal, ketamine intravenous, Ecotrin oral, Opana injection, Diskets oral, Lortab 10-325, phenyltoloxamine-acetaminophen, Relagesic, butorphanol tartate, Synalgos-DC, Talwin injection, Feverall rectal, fenoprofen, Mediproxen, Athenol, Midol PM, Bufferin, Dologen, Wal-Profen, clonidine epidural, Pamprin Max, ibuprofen intravenous, diclofenac submicronized, Lortab 7.5-325, Oxaydo, Alfenta injection, Sublimaze injection, Lorcet HD, Tactinal, pentazocine lactate injection, Anacin, dihydrocodeine-aspirin-caffeine, Provil, Anacin Maximum Strength, meperidine in 0.9% sodium chloride intravenous, Infumorph P/F injection, ibuprofen-diphenhydramine citrate, hydromorphone in 0.9% sodium chloride intravenous, Primlev, ketorolac nasal, Ketalar injection, alfentanil injection, chlorpheniramine-acetaminophen, Nortemp, Acephen rectal, Astramorph injection, Masophen, Ultiva intravenous, remifentanil intravenous, Duraclon epidural, Extraprin, acetaminophen-pyrilamine maleate, remifentanil in 0.9% NaCl intravenous, brompheniramine-acetaminophen, diclofenac intravenous, naproxen-diphenhydramine, indomethacin submicronized, buprenorphine. Any anti-CNS disorder agent or pain reliever known in the art can be co-used with a lithium benzoate compound to achieve the intended therapeutic effects.

The lithium benzoate compounds and compositions comprising such provided herein can be administered by any suitable route, including enteral (e.g., oral), parenteral, intravenous, intramuscular, intra-arterial, intramedullary, intrathecal, subcutaneous, intraventricular, transdermal, interdermal, subcutaneous, intradermal, rectal, intravaginal, intraperitoneal, topical (as by powders, ointments, creams, and/or drops). Specifically, contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a lithium benzoate compound required to achieve an effective amount will vary from subject to subject, depending, for example, on species, age, and general condition of a subject, severity of the side effects or disorder, identity of the particular lithium benzoate compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a lithium benzoate compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every other week, one dose monthly or one dose every other month. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a lithium benzoate compound described herein. In certain embodiments, a dose described herein includes independently between 3 mg and 10 mg, inclusive, of a lithium benzoate compound described herein. In certain embodiments, a dose described herein includes independently between 10 mg and 30 mg, inclusive, of a lithium benzoate compound described herein. In certain embodiments, a dose described herein includes independently between 30 mg and 100 mg, inclusive, of a lithium benzoate compound described herein. In certain embodiments, a dose described herein includes independently between 100 mg and 300 mg, inclusive, of a lithium benzoate compound as described herein. In certain embodiments, a dose described herein includes independently between 300 mg and 1000 mg, inclusive, of a lithium benzoate compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A lithium benzoate or a composition comprising such, as described herein, can be administered in combination with one or more additional pharmaceutical agents (e.g., therapeutically and/or prophylactically active agents) useful in treating, reducing the risk for, or delaying the onset of any of the target diseases/conditions as described herein. The lithium benzoate or the composition comprising such can be administered in combination with the additional pharmaceutical agents that improve their activity (e.g., activity (e.g., potency and/or efficacy) in treating and/or reducing the risk for a neuropsychiatric disorder in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a lithium benzoate compound described herein and an additional pharmaceutical agent shows a synergistic effect that is absent in a pharmaceutical composition including one of the lithium benzoate compound and the additional pharmaceutical agent, but not both.

The lithium benzoate or a composition comprising such can be administered concurrently with, prior to, or subsequent to one or more additional pharmaceutical agents, which may be useful as, e.g., combination therapies in treating and/or reducing the risk for a neuropsychiatric disorder in a subject. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating and/or reducing the risk for a neuropsychiatric disorder in a subject. In certain embodiments, the additional pharmaceutical agent is a pharmaceutical agent approved by a regulatory agency (e.g., the US FDA) for treating and/or reducing the risk for a neuropsychiatric disorder in a subject. Each additional pharmaceutical agent may be administered at a dose and/or on a time schedule determined for that pharmaceutical agent. The additional pharmaceutical agents may also be administered together with each other and/or with the lithium benzoate or a composition comprising such described herein in a single dose or administered separately in different doses. The particular combination to employ in a regimen will take into account compatibility of the lithium benzoate compound described herein with the additional pharmaceutical agent(s) and/or the desired therapeutic and/ or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an agent for treating a neuropsychiatric disorder. In certain embodiments, the lithium benzoate compounds described herein or pharmaceutical compositions can be administered in combination with a therapy for treating a CNS disorder or alleviating pain.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the present disclosure may be more fully understood, the following examples are set forth. The synthetic and biological examples described in this application are offered to illustrate the lithium benzoate compounds, compositions comprising such, and methods provided herein and are not to be construed in any way as limiting their scope.

Example 1: Lithium Benzoate Protects Primary Cortical Neurons from 3-NP Toxicity Mitochondrial dysfunction has been implicated in the pathogenesis of many neurodegenerative disorders as well as neural injuries, such as, Huntington's disease (HD), MSA, periventricular leukomalacia, Friedreich's ataxia, Gaucher disease, subarachnoid hemorrhage, perinatal hypoxic ischemic encephalopathy, progressive supranuclear palsy (PSP), intracranial hypertension, sporadic Creutzfeldt-Jacob disease, tardive dyskinesia, Rett syndrome, and various motor neuron diseases: ALS, primary lateral sclerosis, hereditary spastic paraparesis, progressive bulbar palsy (some have SOD1 mutation), spinal muscular atrophy, X-linked spinobulbar muscular atrophy (Kennedy disease). 3-Nitropropionic acid (3-NP) is an irreversible mitochondrial complex II inhibitor and is commonly used in both in vivo and in vitro models for the studies of mitochondria dysfunction. 3-NP can also induce in vivo protein oxidation and thus can be used as an agent for inducing oxidative stress and/or reactive oxygen species (ROS) overproduction, which are known to be associated with various CNS disorders, such as multiple system atrophy (MSA) and seizure. In this example, the neuro-protective effect of lithium benzoate was investigated on 3-NP induced toxicity in primary cortical culture.

Materials and Methods

Preparation of Primary Culture

Primary cortical cultures were prepared from embryonic day 18 (E18) fetal Sprague Dawley (SD) rat brains. The cells were maintained in Neurobasal medium supplemented with B27 (GIBCO/Life Technologies of Thermo Fisher Scientific Corporation) at 37° C. for 7 days to allow growth of dendrites before experimentation.

Drugs and Reagents

3-NP (Cat. No. 73803, Sigma, St. Louis, Mo., USA) was dissolved in phosphate-buffered saline (PBS) as a stock solution of 1 M and adjusted to pH 7.4 with 10 M sodium hydroxide. The 3-NP stock solution was then dispensed into 1-ml aliquots, protected from light, and stored at −20° C. until use. Lithium benzoate (LiBen), sodium benzoate (NaBen), and lithium chloride (LiCl) were all reconstituted in sterile ddH$_2$O to make stock solutions of 50 μM before storage at 4° C. until use.

Hoechst Staining

Hoechst staining is used to assess the extent of the cell survival. Cells were fixed in 4% paraformaldehyde (PFA) in phosphate-buffered saline (PBS), incubated with the Hoechst 33342 diluted in PBS (1:1000) for 5-15 minutes. The Hoechst staining is used to assess the extent of the cell survival after the exposure to 2.5 mM 3-NP for 24 hours.

Immunocytochemistry and Confocal Microscopy

Cells were fixed in 4% PFA and washed in PBS, blocked with 2% bovine serum albumin (BSA) and treated by 0.03% Triton X-100 in PBS, before being incubated with mouse monoclonal antibody against microtubule-associated protein-2 (MAP-2) in 1:150 dilution (Cat. No. MAB378, CHEMICON International, Inc., Temecula, Calif., USA). The goat anti-mouse IgG Alexa fluor-conjugated secondary antibodies (Cat No. A11003, Thermo Scientific) in 1:500 dilution were applied to recognize the primary antibodies of the MAP-2. For confocal microscopy, the coverslips were observed under a laser-scanning confocal microscope (Zeiss LSM700; Oberkochen, Germany) equipped with filter sets to detect the corresponding fluorescent signals.

Detection of Cellular Reactive Oxygen Species (ROS)

Reactive oxygen species (ROS) are detected on primary cortical neuronal culture by CellROX Oxidative Reagents (catalog number 10444, Life Technologies Corp. USA). To study the therapeutic effects of lithium benzoate, the cultured cells were treated with lithium benzoate (0, 0.5, 1 or 3 mM) for 24 hours. The cells were then exposed to 2.5 mM 3-NP for 24 hours. Subsequently, 2 mM CellROX Reagent was added, and then incubated for 10 hours. CellROX Green Reagent is a DNA dye, and upon oxidation, it binds to DNA; thus, its signal is localized in the nucleus and mitochondria. ROS were quantified by fluorescence intensity. The samples were observed under a laser scanning confocal microscope Zeiss LSM700 (Zeiss, Germany) equipped with filter sets to detect fluorescent signal.

Data Analysis

Multiple groups were first analyzed by one-way analysis of variance (ANOVA) followed by a post hoc Student-Newman-Keuls test. P-value of less than 0.05 was considered significant.

Results

Cell Survival of Primary Cortical Culture Pre-Treated with Lithium Benzoate

Figure 1:
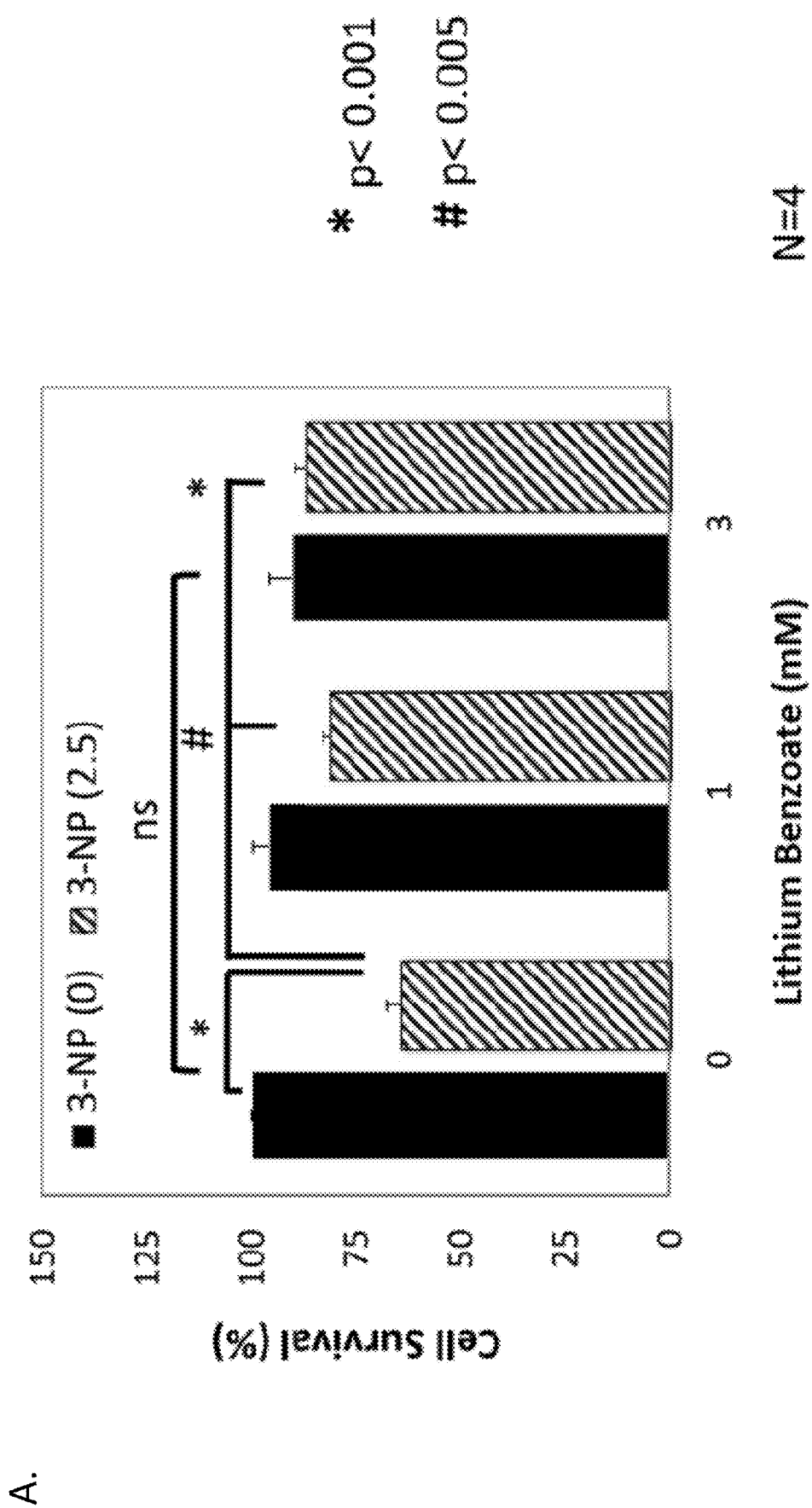
FIG. 1 includes diagrams showing the neuro-protective effect of lithium benzoate on toxicity induced by 3-nitropropionic acid (3-NP) in primary cortical culture. A: a bar graph indicating the percentage of cell survival for cells treated with 0, 1, or 3 mM lithium benzoate. B: a bar graph showing the "Death index," which was defined as the ratio of dead cells to survived cells, in cortical culture treated or not treated by 3-NP. C: a photo showing the result of MAP-2 immunocytochemistry of cells pre-treated with lithium benzoate (1 or 3 mM). 3NP causes cell death, while lithium benzoate rescued the cell in a dose-dependent manner.
Figure 1:
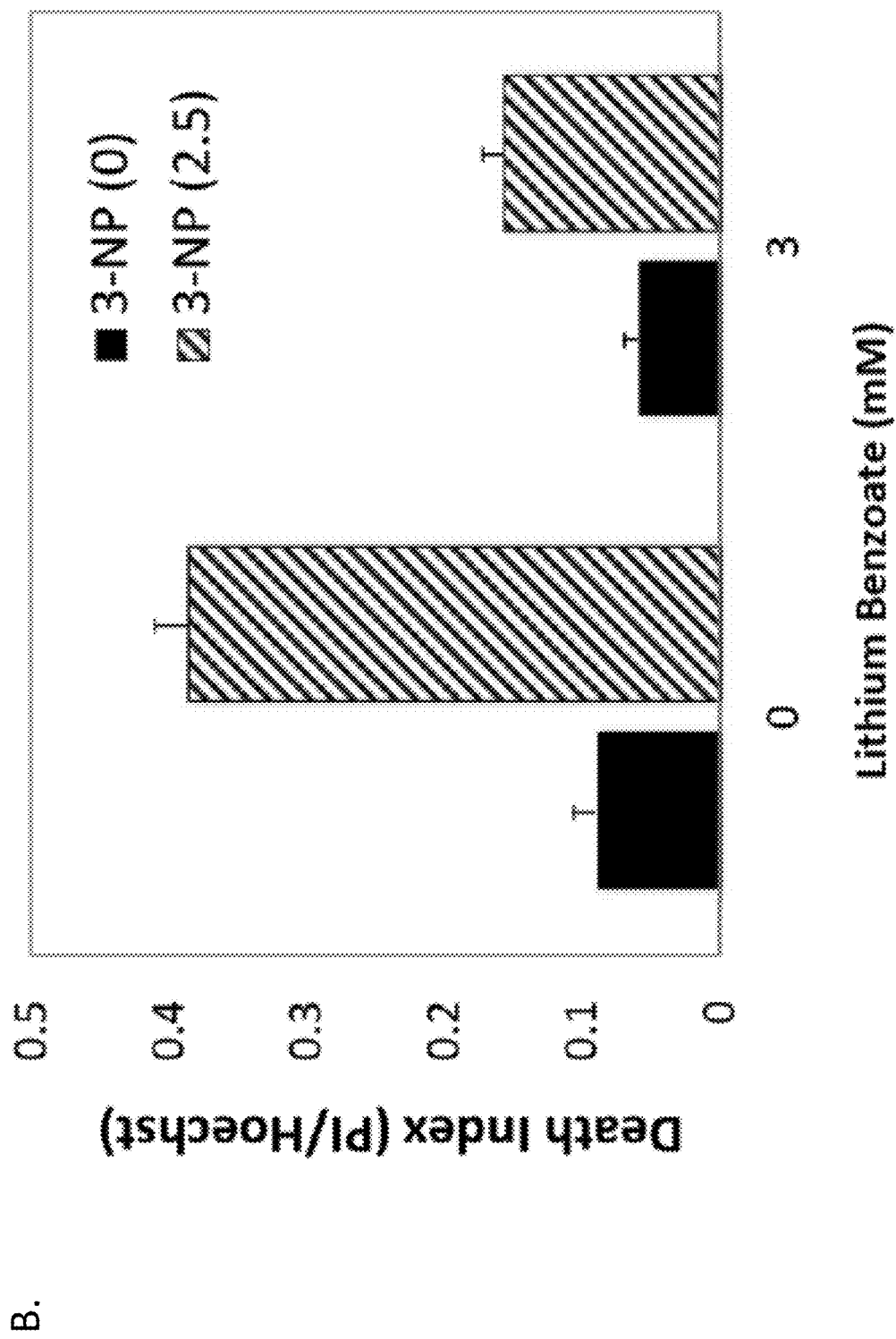
Figure 1:
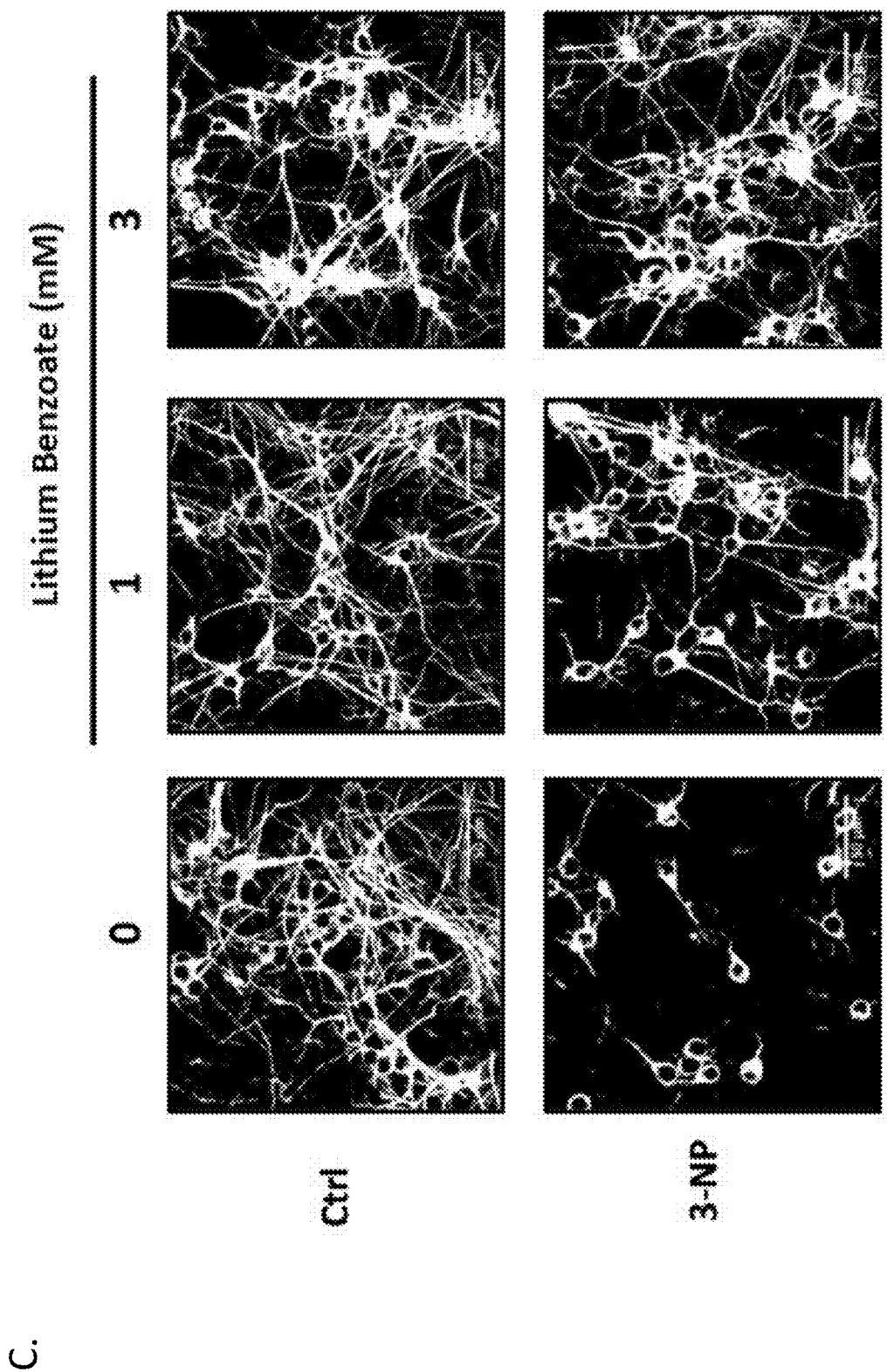

For cell survival test, primary cortical neurons grown on coverslips in 24-well were pre-treated with lithium benzoate (1 or 3 mM) for 24 hours. The cells were then exposed to 2.5 mM 3-NP for 24 hours. As shown in FIG. 1, panel A, the treatment of 3-NP induced cell death of primary cortical neurons, while the treatment with lithium benzoate (at 1 mM or 3 mM) significantly protected primary cortical neuron death induced by 3-NP toxicity. No difference was observed in cortical culture treated only with lithium benzoate, not 3-NP. These results indicate that lithium benzoate rescued the 3-NP-induced neuronal death.

Quantitative analysis was also performed to assess the extents of cell death. At least three vision fields were randomly selected and the averaged numbers of dead cells and all nuclei per vision field on each coverslip were calculated. As shown in FIG. 1, panel B, exposure to 3-NP drastically raised the death index of primary cortical neurons from 0.1 to 0.4, while pre-treatment by lithium benzoate (3 mM for 24 hours) substantially reduced the death index of 3-NP treated cells to less than 0.2. The reduction in the death index indicates a neuronal protective effect of lithium benzoate.

For immunocytochemistry, neurons treated with lithium benzoate, 3-NP, or both as described above were incubated with mouse monoclonal antibody against MAP-2. MAP-2 is a neuronal protein found in the neuronal cell body and dendrites. The confocal microscopy analysis revealed that the protective effects of lithium benzoate on primary cortical cultures subjected to 3-NP exposure was, at least in part, associated with the neuronal protection (FIG. 1, panel C).

Figure 2:
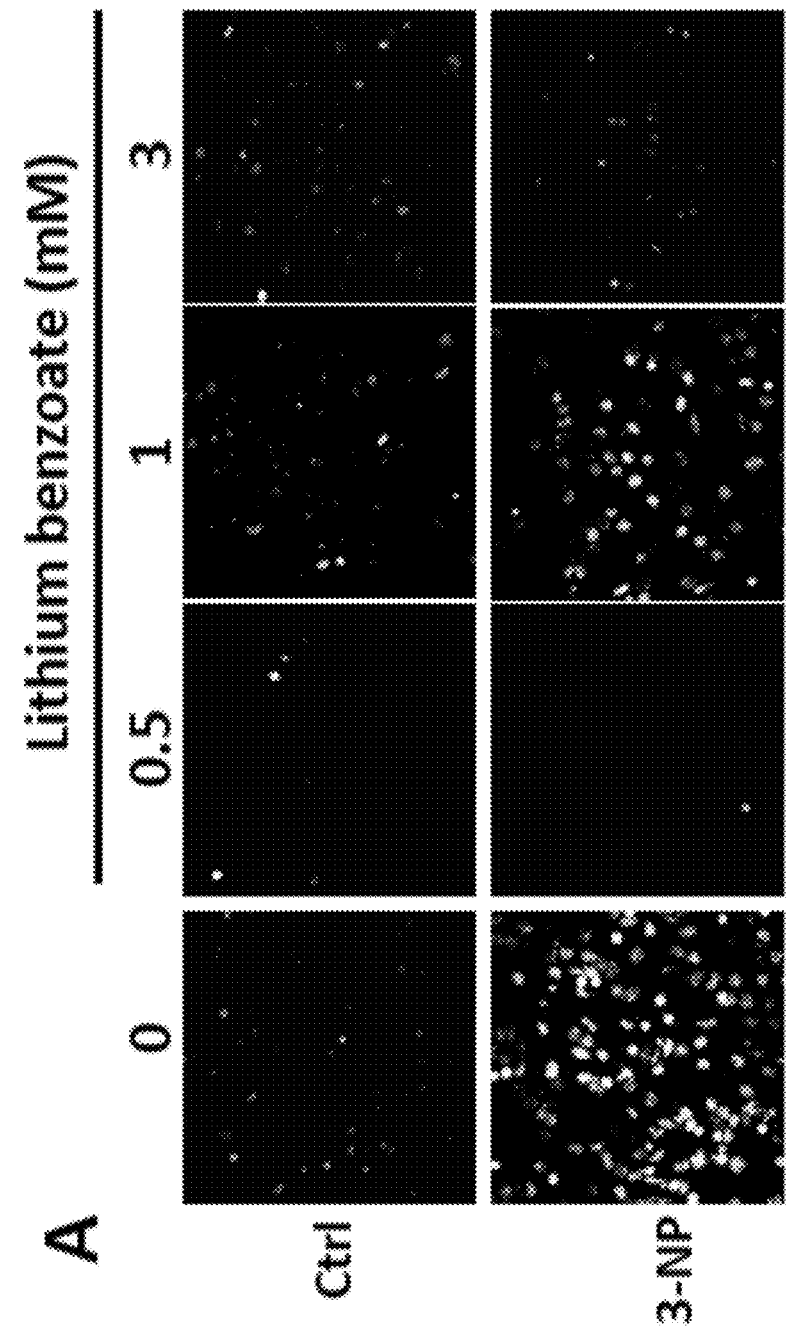
FIG. 2 includes diagrams showing the effect of lithium benzoate in rescuing ROS production induced by 3-NP in primary cortical culture. A: Examples of the fluorescence diagram of ROS in cortical culture pre-treated with lithium benzoate at 0, 0.5, 1, 3 mM. B: a graph showing statistical analysis results of the fluorescence signals shown in panel A, comparing the ROS reduction effects among lithium benzoate (0.5 mM), sodium benzoate (0.5 mM) and lithium chloride (0.5 mM). Bars indicate the standard error mean. * $p$-value $<0.05$;  $p$-value $<0.01$; * $p$-value $<0.001$; **** $p$-value $<0.0001$, $ indicates LiBen comparing to LiCl, $: $p$-value $<0.05$; # indicates LiBen comparing to NaBen, ##: $p$-value $<0.01$.
Figure 2:
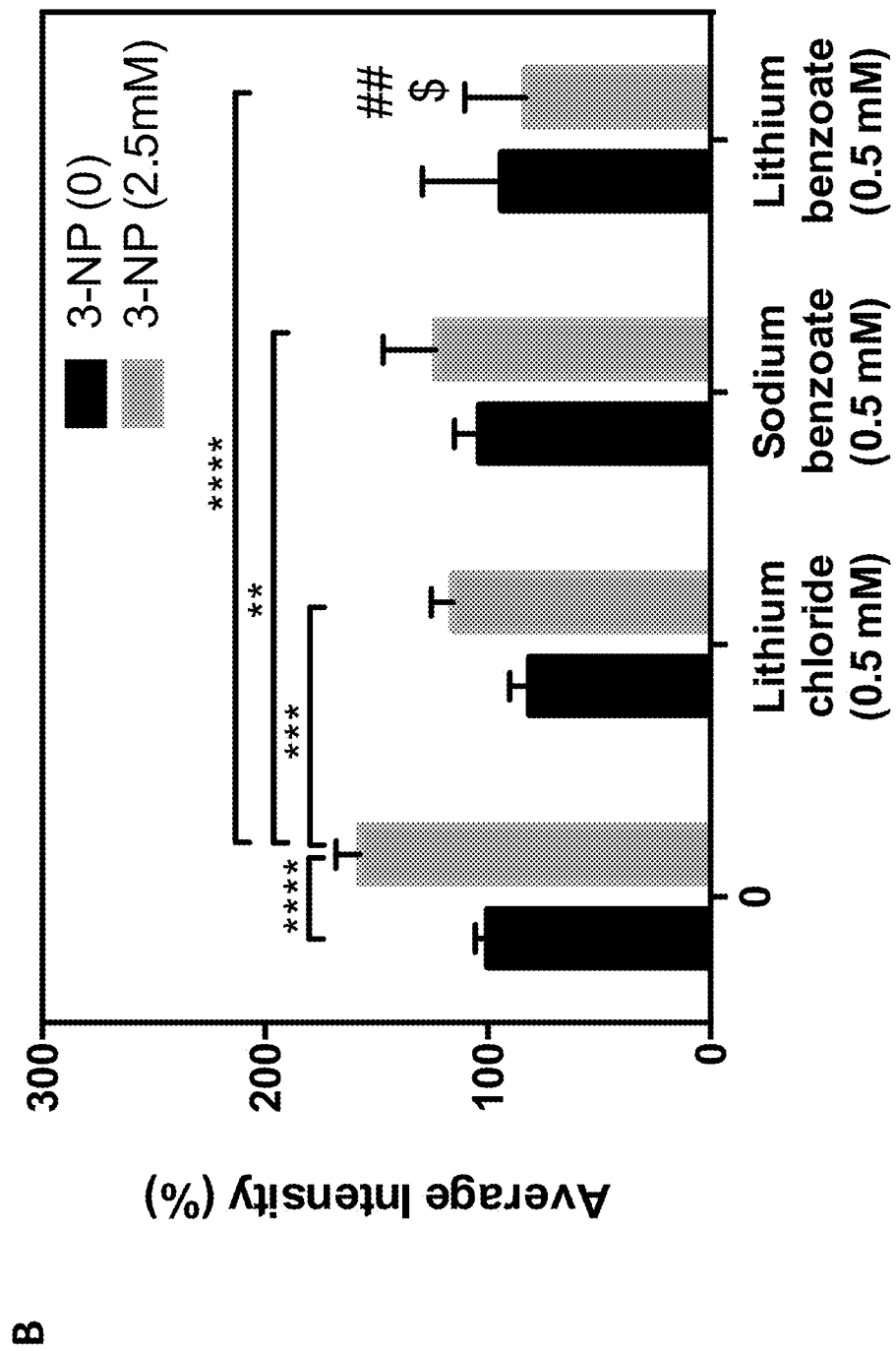

Detection of Cellular Reactive Oxygen Species (ROS) in Cortical Culture Pre-Treated with Lithium Benzoate Furthermore, 3-NP evokes reactive oxygen species (ROS) production correlated with mitochondrial dysfunction. Total and mitochondrial ROS productions could be quantified by CellROX reagents. FIG. 2, panels A-B indicated the florescence intensity (%) of ROS with 3-NP at different concentrations in cortical cells. 3-NP increased more than 50% of ROS production, which was significantly reduced by the treatment of lithium benzoate. This effect could be observed especially at of 0.5 mM (p<0.0001) (FIG. 2, panels A and B), indicating lithium benzoate even eliminated or inhibited the production of ROS, back to the basal level. To compare the ROS reduction effect with lithium benzoate, sodium benzoate and lithium chloride were also incubated 24 hours before the exposure of 3-NP in primary cortical culture. As shown in FIG. 2, panel C, sodium benzoate and lithium chloride could also reduce the amount of cellular ROS. However, the effect of ROS reduction is much more significant by lithium benzoate than sodium benzoate and lithium chloride (FIG. 2, panel B).

Taken together, the results obtained from this example indicate that lithium benzoate treatment confers neuronal protection against the mitochondrial dysfunction caused by 3-NP exposure. In addition, the results of ROS studies reveal the antioxidant capacity of lithium benzoate, which is significantly better than sodium benzoate and lithium chloride, suggesting a potential mitochondrial restorative mechanism of lithium benzoate to reduce neuronal cell death. ROS mediates mitochondria damage, which plays an important role in the pathogenesis of neurodegenerative disorders such as Huntington's disease (Reddy et al., Trends Mol Med. 2008 February; 14(2):45-53), MSA, periventricular leukomalacia, Friedreich's ataxia, Gaucher disease, subarachnoid hemorrhage, perinatal hypoxic ischemic encephalopathy, progressive supranuclear palsy (PSP), intracranial hypertension, sporadic Creutzfeldt-Jacob disease, tardive dyskinesia, Rett syndrome, and various motor neuron diseases: ALS, primary lateral sclerosis, hereditary spastic paraparesis, progressive bulbar palsy (some have SOD1 mutation), spinal muscular atrophy, X-linked spinobulbar muscular atrophy (Kennedy disease). Further, oxidative stress and/or ROS overproduction are known to be associated with CNS disorders, such as MSA and Seizure. Fullner et al., Front Neurosci., 10:99 (2016) and Bhowmik et al., Br. J. Pharmacol. 167(7):1398-1414 (2012). Accordingly, lithium benzoate would be effective in treating these CNS disorders associated with mitochondria dysfunction, oxidative stress, and/or ROS overproduction, for example, HD, MSA, and seizure.

Example 2: Lithium Benzoate Enhances Spare Respiratory Capacity for the Mitochondria Function This example demonstrated studies of mitochondrial function improved by lithium benzoate. In addition to the protection of mitochondria dysfunction on neurodegenerative disease, such as Huntington's disease (HD) by lithium benzoate, the oxygen consumption rate (OCR) of cortical neurons treated with lithium benzoate was investigated in this example.

Materials and Methods

Preparation of Primary Culture

The preparation of primary cortical culture was as described before, but the cells were seeded on XF 96 well cell culture microplates. On the day of assay, culture media were changed to XF Assay medium (Seahorse Biosciences, USA). Prior to assay, plates were transferred into an incubator with CO2 supplementation at 37° C. and kept for 1 hour. The overall OCR was calculated.

Mitochondrial Respiration

The XF Cell Mito Stress Test kit (Seahorse Biosciences, USA) was used to measure the mitochondrial activity of cortical neurons pre-treated with, lithium benzoate (LiBen, 3 mM), sodium benzoate (NaBen, 3 mM) or lithium chloride (LiCl, 3 mM) for 24 hours. Oncostatin M (OSM) was performed as a comparable group, which might protect mitochondrial dysfunction. The XF Cell Mito Stress Test modulates respiration that target components of the electron transport chain (ETC) in the mitochondria to reveal key parameters of metabolic function. The modulators (oligomycin, FCCP, and a mix of rotenone and antimycin A) are serially injected to measure ATP production, maximal respiration, and non-mitochondrial respiration. Proton leak and spare respiratory capacity are then calculated using these parameters.

Results

Figure 3:
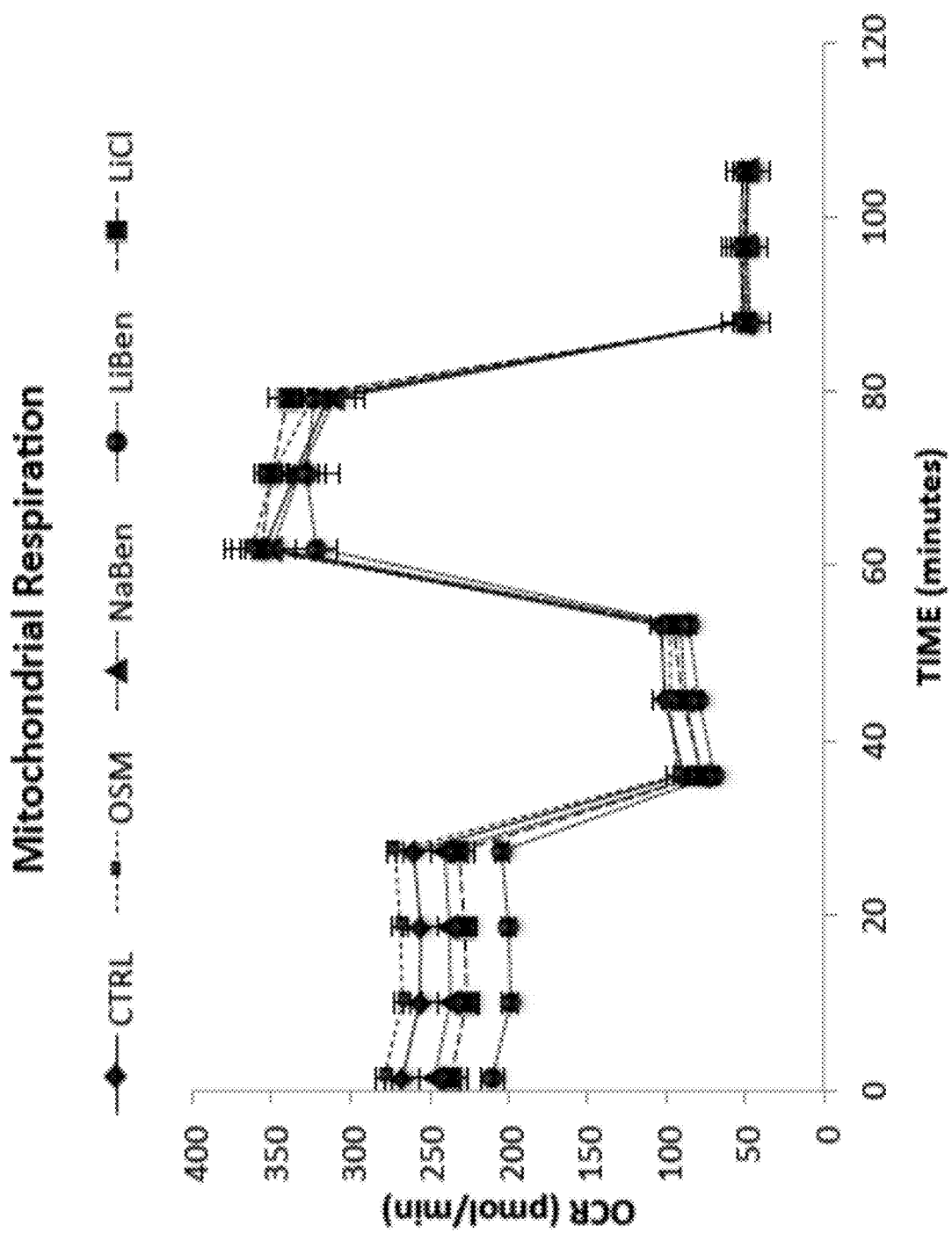
FIG. 3 includes diagrams showing that lithium benzoate enhanced spare respiratory capacity for the mitochondria function. A: a time-dependent line graph of OCR with sequential injection of modulators. CTRL, control; LiBen, lithium benzoate; LiCl, lithium chloride; NABen, sodium benzoate; OCR, oxygen consumption rate; OSM, oncostatin M. B and C: bar graphs of OCR analyzed from the result of panel A with each part of modulators injection, including basal respiration, spare respiratory capacity, proton leak, and ATP production. Lithium benzoate shows better mitochondrial function in less basal activity, proton leak, ATP production than sodium benzoate and lithium chloride as well as more spare respiratory capacity than sodium benzoate.
Figure 3:
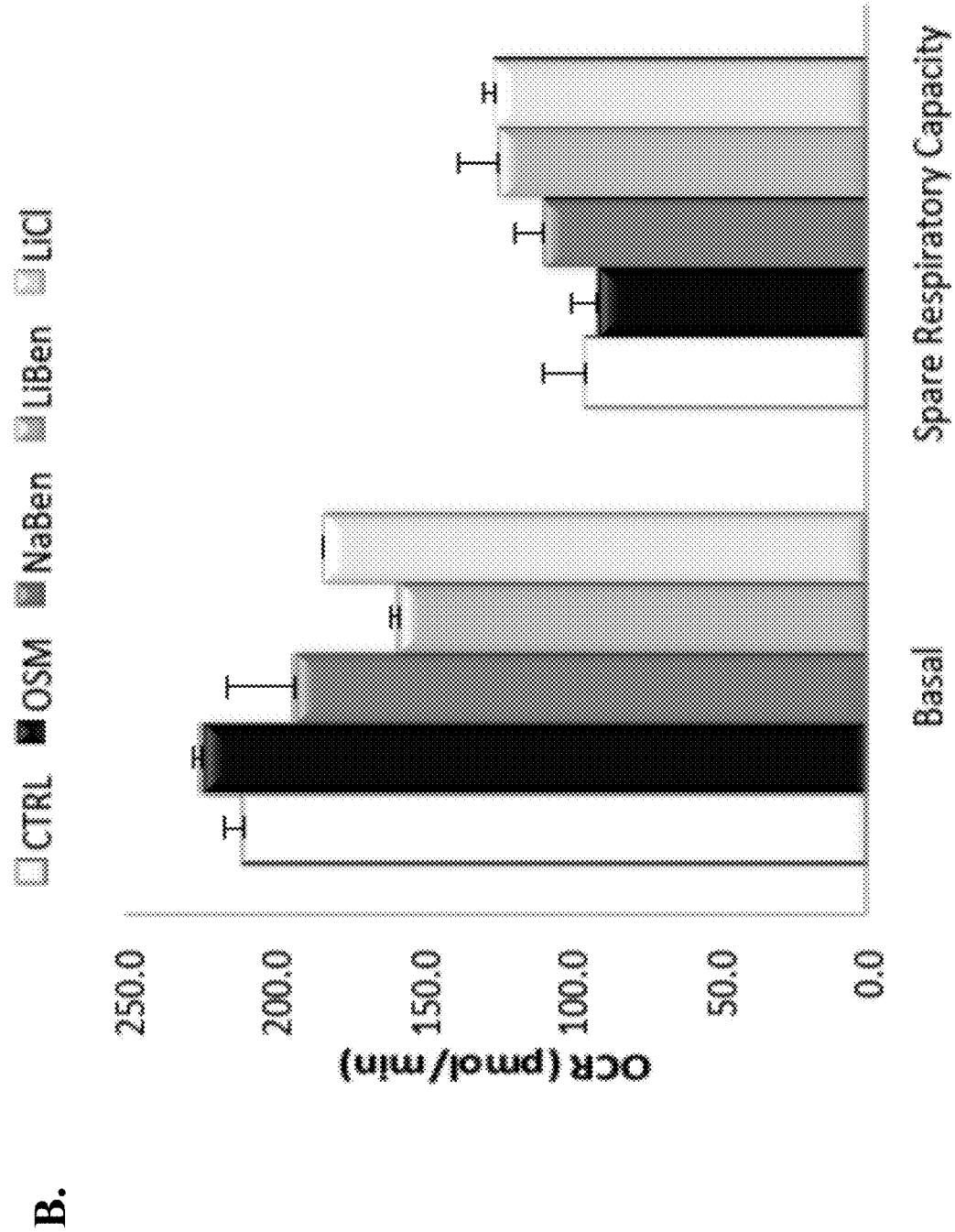
Figure 3:
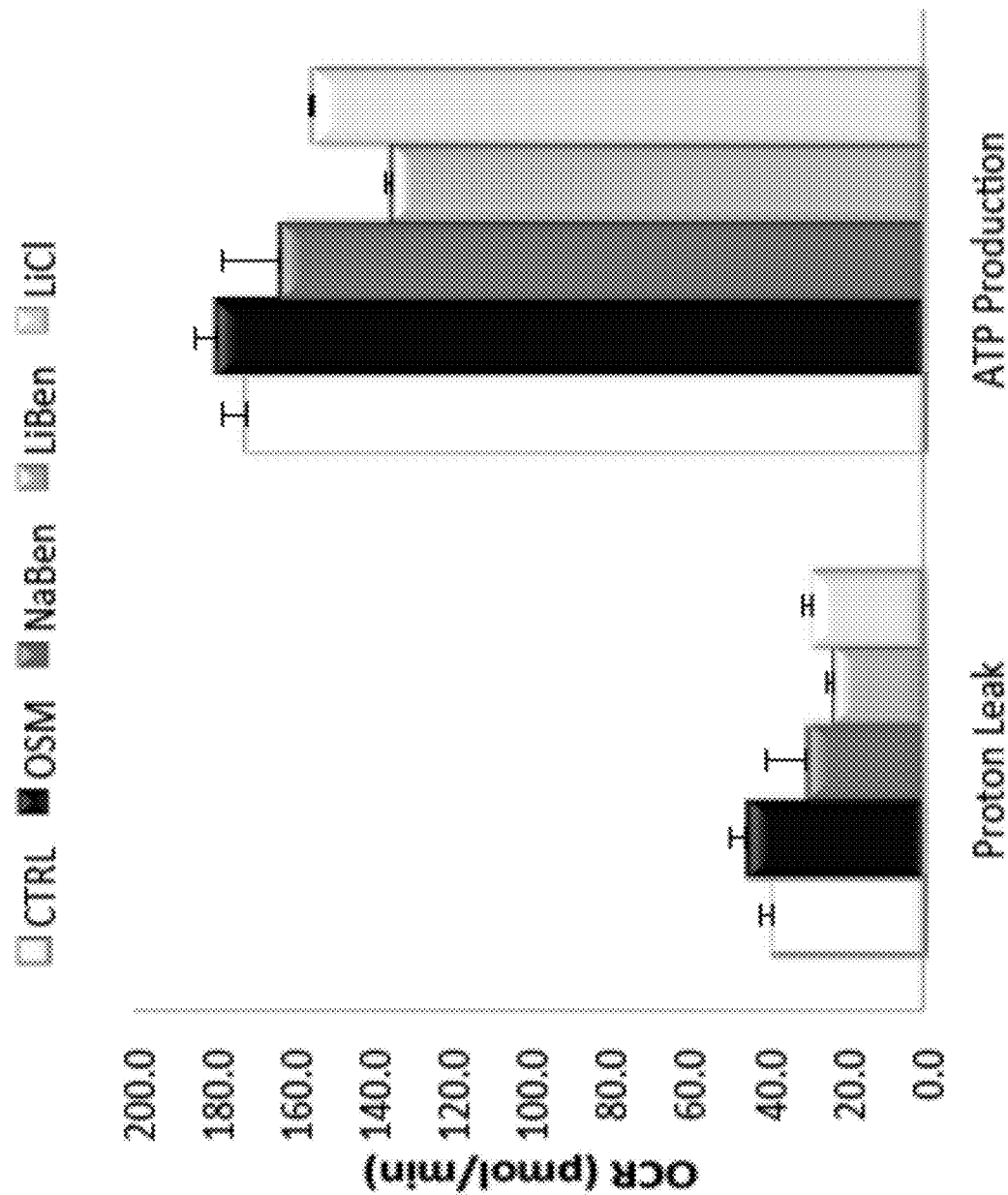

Detection of Mitochondrial Respiration in Cortical Culture Pre-Treated with Lithium Benzoate, Sodium Benzoate, and Lithium Chloride After pre-treatment of OSM, LiBen, NaBen or LiCl in primary cortical culture, the mitochondrial respiration was examined by the XF Cell Mito Stress Test kit as previous described. As shown in FIG. 3, panel A, the maximal respiration had no differences among the groups, which showed the general function of mitochondria to achieve the maximum rate of respiratory are the same. Under different states adjusted by injection of modulators (oligomycin, FCCP, and a mix of rotenone and antimycin A), the basal respiration, spare respiratory capacity, proton leak, and ATP production were determined and shown in FIG. 3, panels B and C.

Pre-treatment of LiBen (3 mM had reduced more basal OCR than the other groups, which showed lower energetic demand of cells under basal conditions. The increasing of spare respiratory capacity by LiBen (3 mM demonstrated better adaptability of cells, also indicating better ability to respond to energy demands. Although NaBen (3 mM) and LiCl (3 mM) had the same tendency to increase spare respiratory capacity of cells, but are less effective than LiBen (3 mM).

LiBen exhibited better reduction levels of proton leak and ATP production than NaBen or LiCl (FIG. 3). Proton leak would reflect mitochondrial damage. Thus, the results indicate the LiBen protected cells from mitochondria damage. The ATP produced by mitochondria are used to meet the energy demand of cells. It was reduced by lithium benzoate, indicating the lower energetic demand as the basal respiration.

In summary, lithium benzoate reduces the basal energy demand of neurons, protected them from proton leak, and improved the adaptability to demands of the mitochondria activity by increasing the spare respiratory capacity. These improvement of mitochondria functions suggest lithium benzoate can help to treat the diseases associated with mitochondria dysfunction, including Huntington's disease (HD), multiple sclerosis (SCA), amyotrophic lateral sclerosis (ALS), cardiomyopathy, mitochondrial myopathy, diabetes mellitus and deafness (DAD), Leber's hereditary optic neuropathy (LHON), Leigh syndrome, neuropathy, ataxia, retinitis pigmentosa, and ptosis (NARP), myoneurogenic gastrointestinal encephalopathy (MNGIE), myoclonic epilepsy with ragged red fibers (MERRF), and mitochondrial myopathy, encephalomyopathy, lactic acidosis, stroke-like symptoms (MELAS).

Example 3: Lithium Benzoate Ameliorates Disease Progression in Amyotrophic Lateral Sclerosis (ALS)

Amyotrophic lateral sclerosis (ALS) is a fatal neurodegenerative disorder characterized in massive loss of motor neurons; symptoms of ALS start with progressive weakness, atrophy of skeletal muscles and paralysis that eventually lead to death. It has been reported that at least some familial ALS cases were resulted from the missense mutation in human SOD1 gene, accordingly, transgenic mice having mutant form of SOD1 gene were established to recapitulate human ALS symptoms. In this example, transgenic mice B6SJL-Tg(SOD1*G93A)1Gur/J carrying the Gly93→Ala amino acid substitution in the SOD1 gene were used to investigate the effect of lithium benzoate in ALS subjects.

Materials and Methods

Animal and Housing Conditions

All animals used in the examples of the present disclosure were housed in an animal room under temperature control (24-25° C.) and 12:12 light-dark cycle. Standard laboratory chow and tap water were available ad libitum. The experiments procedures were approved by the Institutional Animal Care and Use Committee and were performed in compliance with national animal welfare regulations. Transgenic mice B6SJL-Tg(SOD1*G93A)1Gur/J were purchased from the Jackson Laboratory (USA).

In cohort 1, the female transgenic and wild-type littermates were randomly divided into the following groups: vehicle (wild-type treated with saline, n=5), vehicle-ALS (SOD1(G93A) transgenic mice treated with saline, n=6), drug-ALS (SOD1(G93A) transgenic mice treated with lithium benzoate, n=6). Disease onset of B6SJL-Tg (SOD1*G93A)1Gur/J mice occurred at around 80-90 days of age, while progressive clinical weakness followed by paralysis and death occurred by 135-140 days.

In cohort 2, the male transgenic and wild-type littermates were randomly divided into 3 groups as cohort 1: vehicle (n=5), vehicle-ALS (n=6), and drug-ALS (n=11). Disease onset occurred at around 110-120 days of age, while progressive clinical weakness followed by paralysis and death occurred at around 150-155 days.

Drug Administration

In cohort 1, drug regimen was initiated 8 weeks after birth and continued until the end of study. Lithium benzoate was intraperitoneally injected at a dose of 256 mg/kg weight/day. The vehicle groups received injections of the same volume of saline.

The drug regimen for cohort 2 was the same as that for cohort 1 except the dosing was started at 10 weeks of age.

Animal Behavioral Tasks

Various behavioral tasks were routinely performed starting from 50 days of age (cohort 1) or 13 weeks of age (cohort 2) till death to assess the effects of drug on the neurological deficits.

Cohort 1

Open field is an animal behavioral task that can monitor the overall spontaneous locomotor activity. Each animal was placed in an empty test arena (60 cm×60 cm plastic boxes) for 1 hour, and its activity was assessed by VersaMax Animal Activity Monitoring System (AccuScan Instruments, Inc. Columbus Ohio, USA). Total traveling distance, number of rearing movements and rearing time were analyzed. Performance of open field was measured 1-2 times per week.

Cohort 2

In the open field task, each animal was placed in an empty test arena (43.2 cm×21.6 cm plastic boxes) for 1 hour, and its activity was assessed by Photobeam Activity System (San Diego Instruments, USA). Total traveling and rearing activities (beam break times) were analyzed. Performance of open field was measured once per week.

Rorarod task, which requires animals to balance and walk on a rotating cylinder, is a widely used test to measure coordinated motor skills. The mice were placed on a 5-channel automatic revolving rod apparatus (PanLab/Harvard Apparatus). Prior to the experiments, all mice were trained on a constant speed (8 rpm) on Day −5, −4, −3 to acclimate the mice to the apparatus. After the training sessions, motor coordination was evaluated at 16 rpm for a maximum of 5 min. Three trials (with 10-min intervals) were subjected to each animal per day. Performance of rotarod task was measured once per week, and the longest retention time for each animal was recorded.

Hanging test is performed with mouse models of neuromuscular disorders to demonstrate neuromuscular impairments. A metal wire mesh (0.2 cm diameter, 1 cm×1 cm wide grid) was fixed horizontally 30 cm above the table. One mouse was allowed to grab the wire mesh while the mesh was turned upside-down. The latency to fall was recorded when the animal fell, and a maximum time of 180 s was assigned for analysis. There were two sessions for each individual with a 30-min interval, and the longer time was recorded. Performance of hanging test was measured once per week.

Body Weight

For each animal, body weight was measured weekly starting at 10 weeks of age. The body weight loss indicated an inability to obtain food or water due to the motor impairment occurred during disease progression or any malaise.

Survival

Date and cause of death were recorded for each mouse. Animals were closely monitored and euthanized if moribund, which was defined as the inability of mice to right themselves 30 seconds after being placed on a side, in accordance with the criteria for severe morbidity. The moribund mice were recorded as "dead", and euthanized using carbon dioxide.

Results

Figure 4:
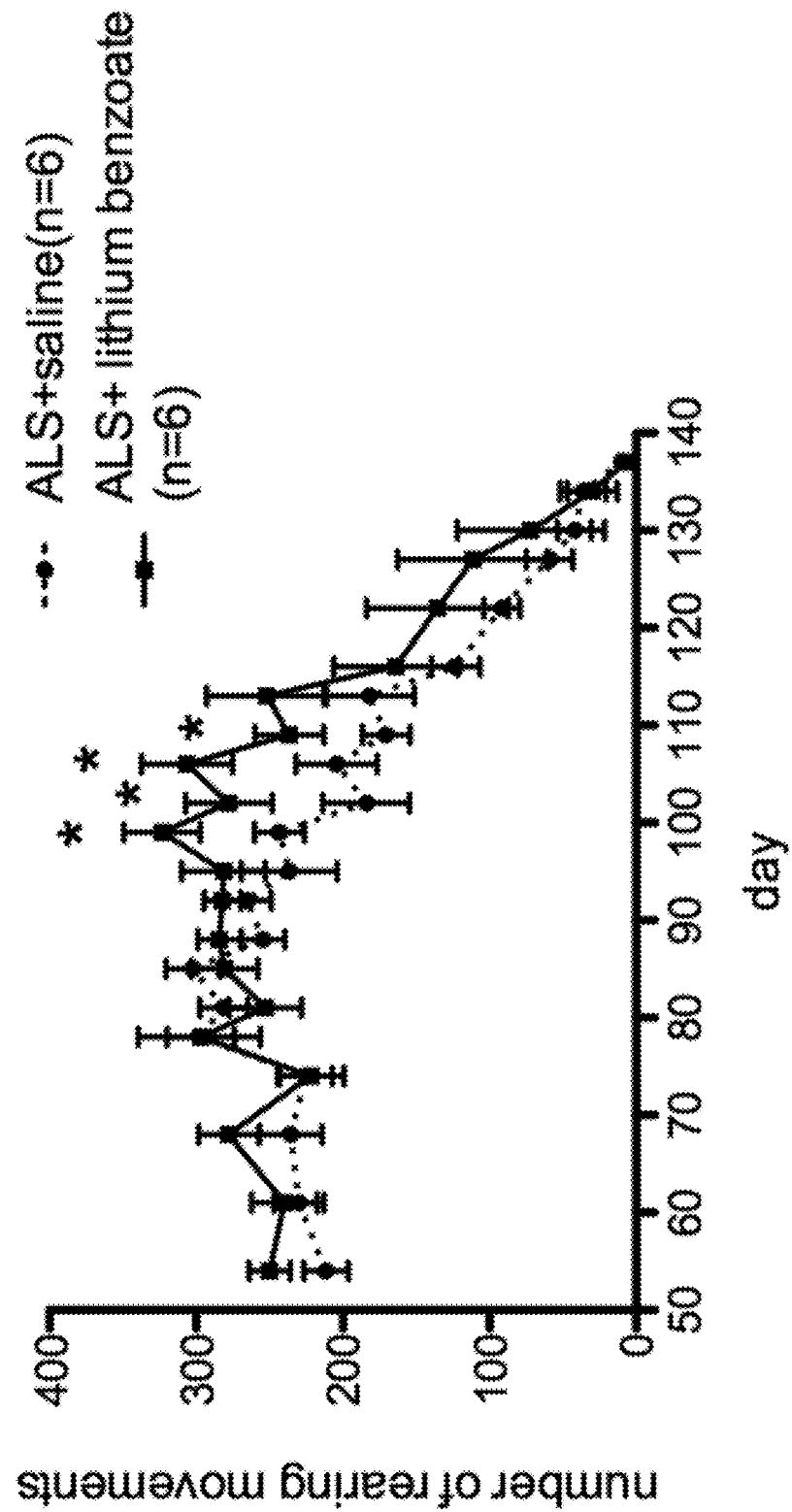
FIG. 4 includes diagrams showing that lithium benzoate ameliorates disease progression in amyotrophic lateral sclerosis (ALS). A: a diagram showing better locomotor activities of number of rearing movements by lithium benzoate treatment. B: a diagram showing better total time of rearing (sec) by lithium benzoate treatment. C: a diagram showing longer latency to fall (sec) in hanging test by lithium benzoate treatment. D: a diagram showing longer latency to fall (sec) in rotarod test by lithium benzoate treatment. E: a diagram showing better rearing activity (beam break times) by lithium benzoate treatment. F: a diagram showing better traveling activity (beam break times) by lithium benzoate treatment. G: a diagram showing less weight loss (g) by lithium benzoate treatment. H: a diagram showing better survival rate (%) by lithium benzoate treatment. * $p$-value $<0.05$.
Figure 4:
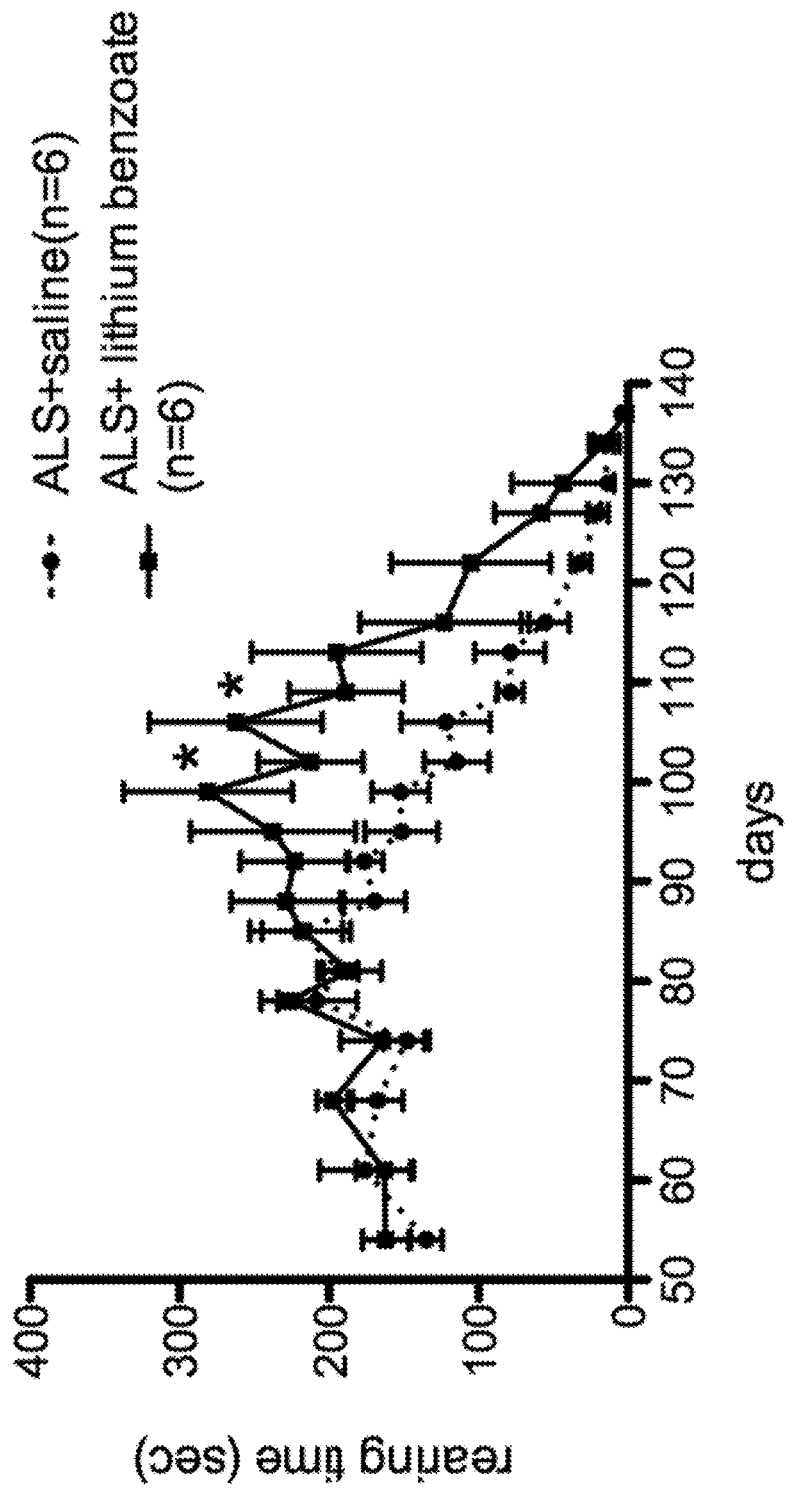
Figure 4:
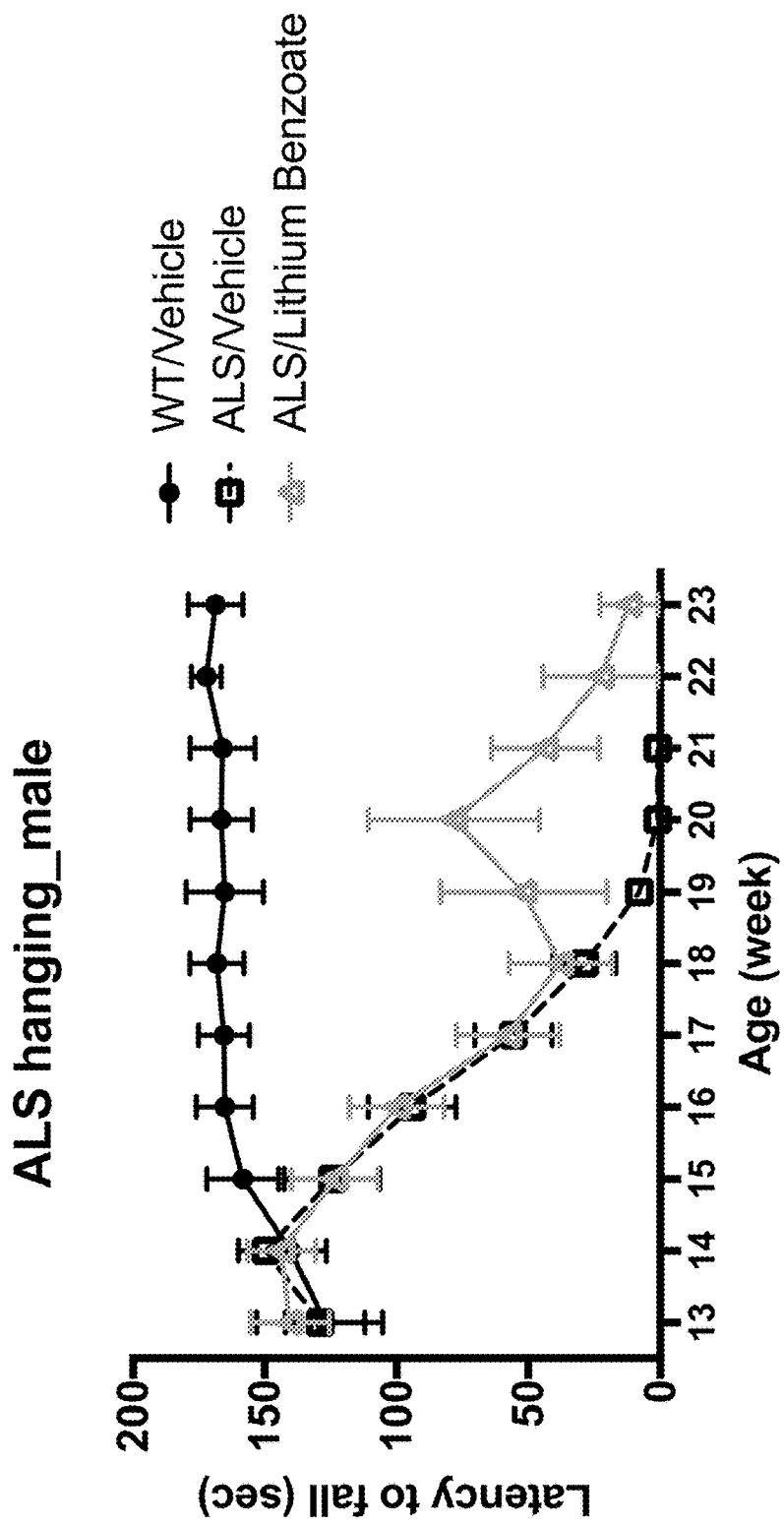
Figure 4:
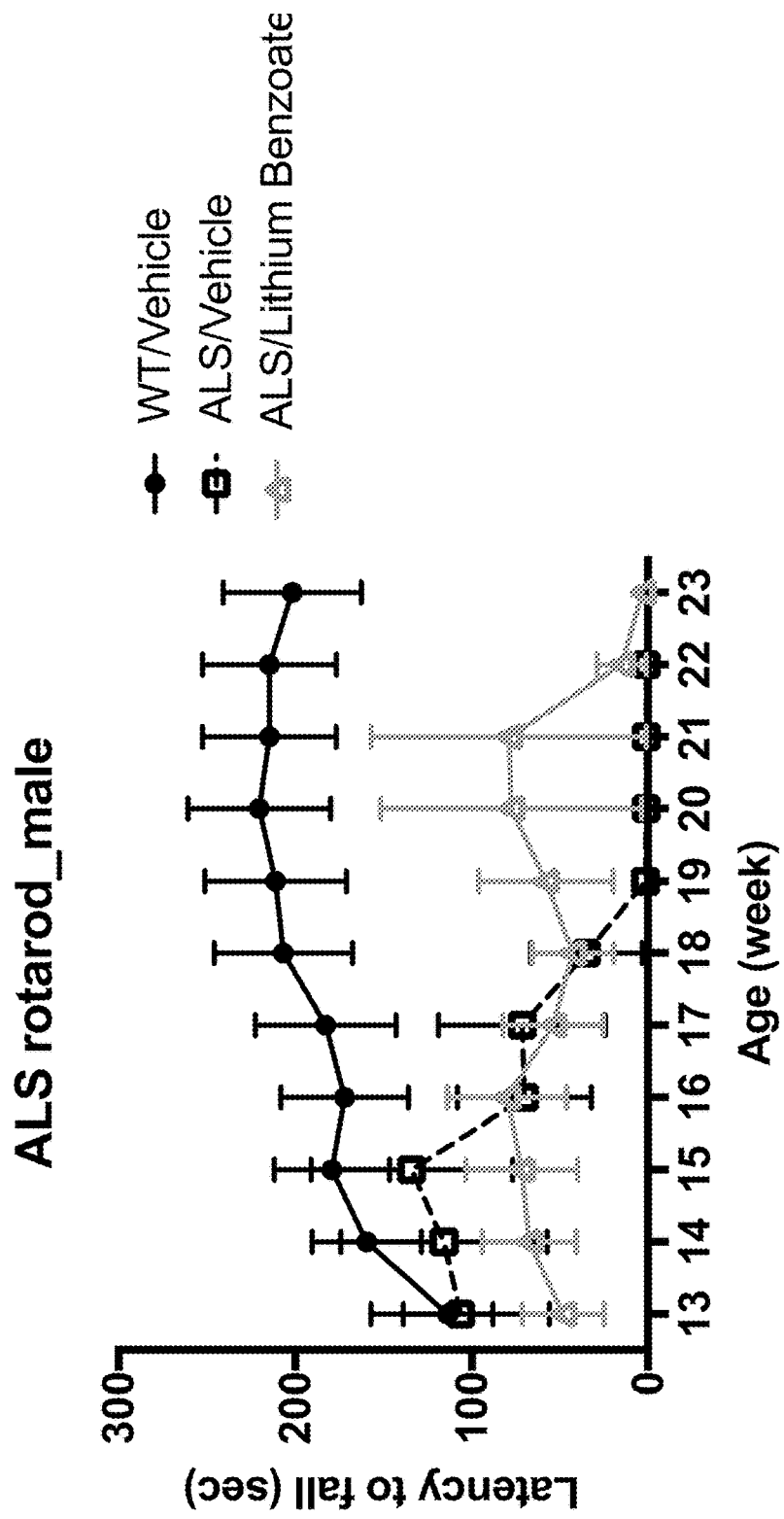
Figure 4:
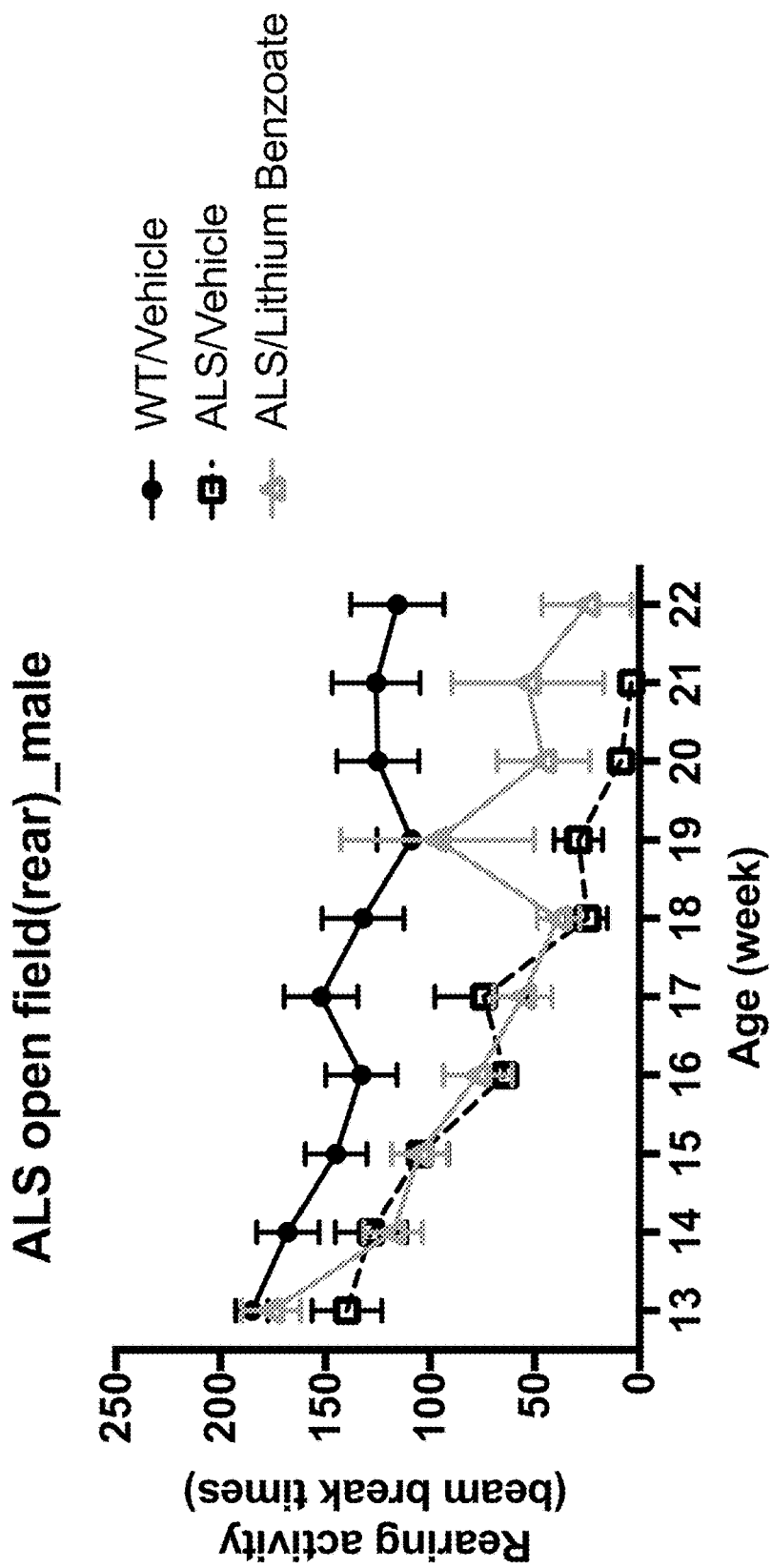
Figure 4:
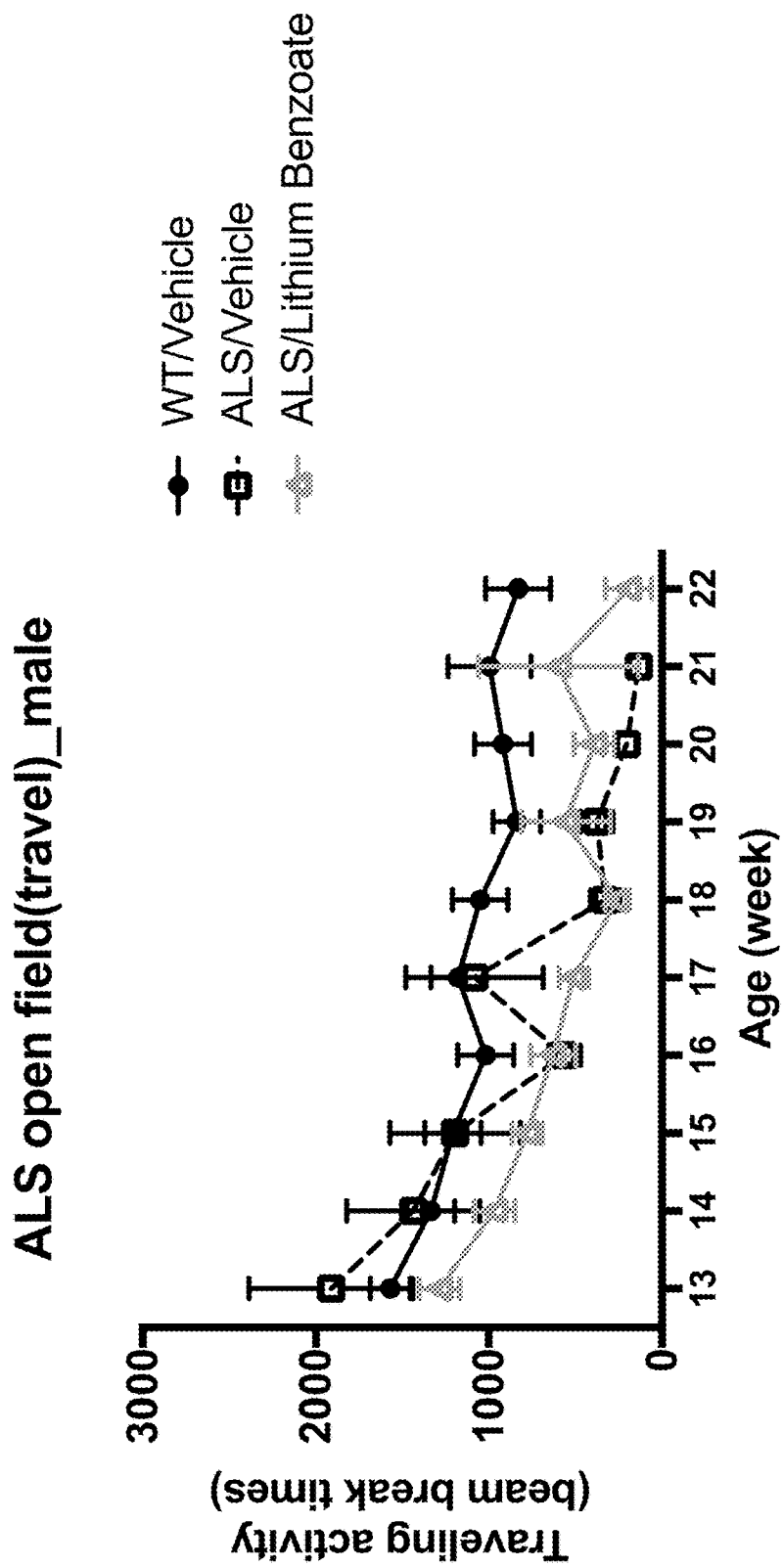
Figure 4:
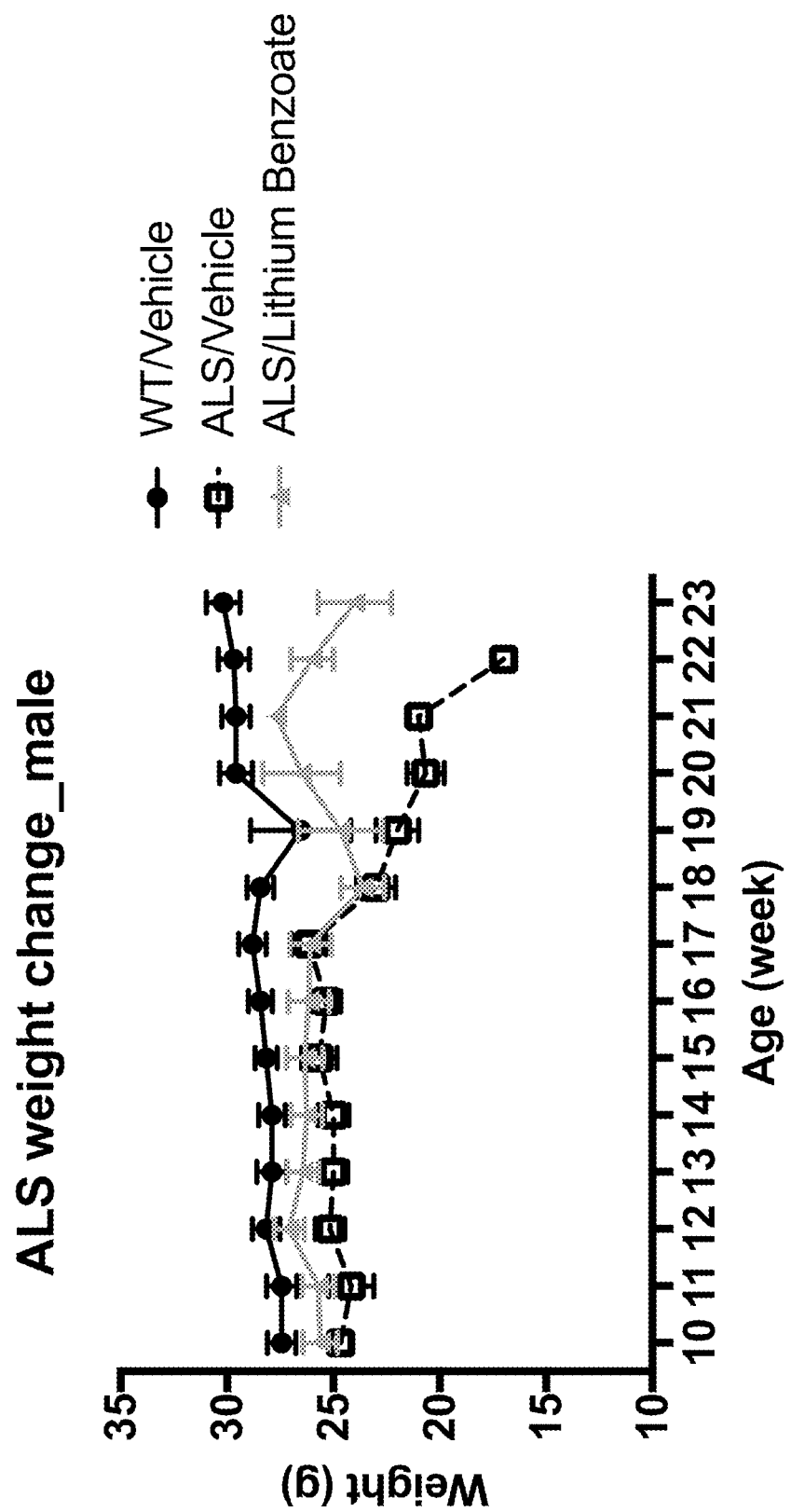
Figure 4:
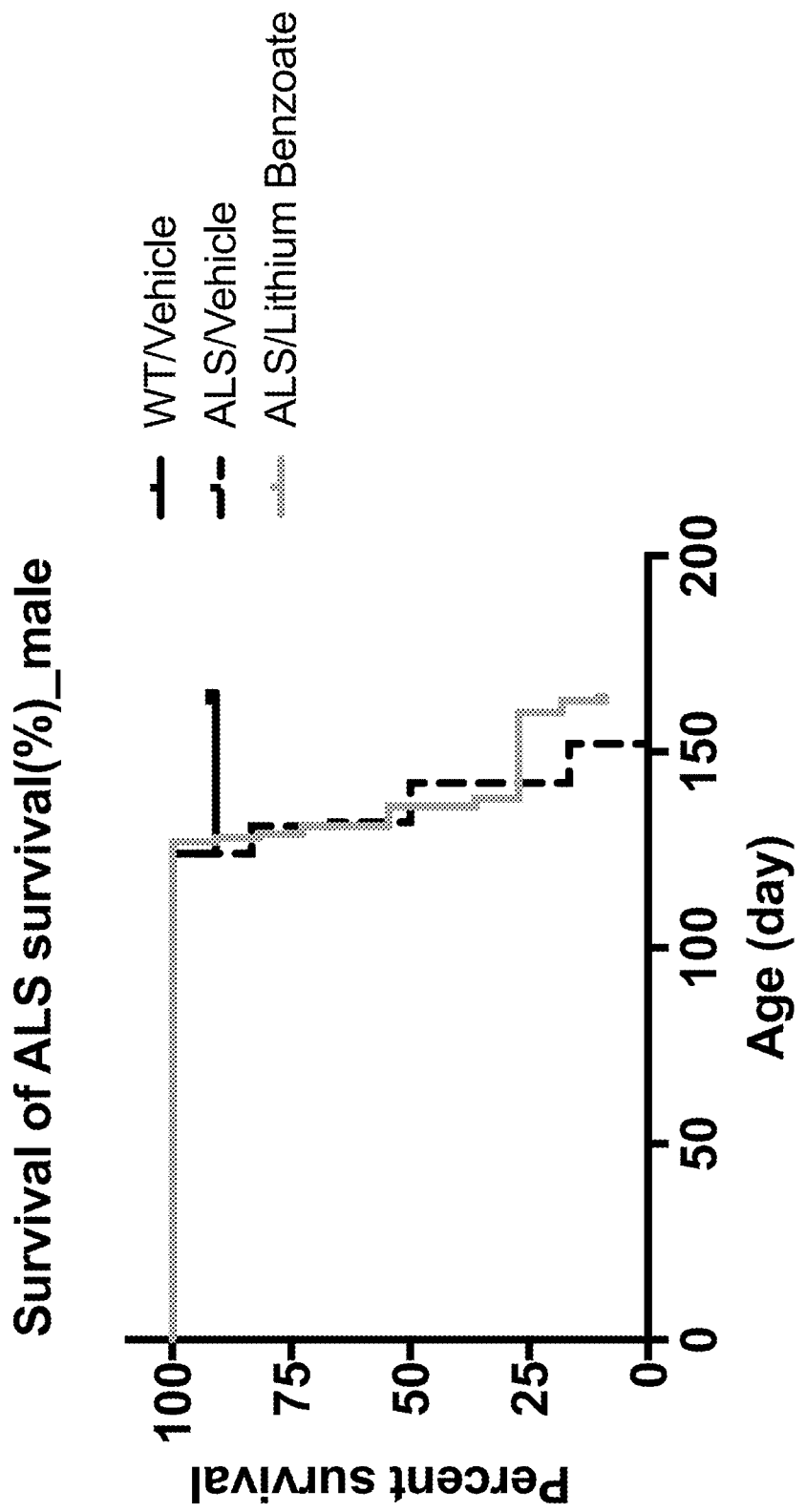

The Performance of Locomotor Activity on Lithium Benzoate Treated SOD1 Transgenic Mice In cohort 1, the open field task was used to investigate the general motility of different groups of mice. FIG. 4, panels A and B are line graphs summarizing the number of rearing movements and rearing time, respectively, covered by transgenic ALS mice treated with saline or lithium benzoate during the test period. The data demonstrated that the hind limb functions of ALS mice treated with lithium benzoate were significantly improved, as compared to their control littermate from about 90 days of age until about 130 days of age. As described above, these results suggest that the lithium benzoate treatment may improve hind limb function during disease progression, especially early in the disease progression. Thus, lithium benzoate would be expected to show therapeutic efficacy in treating ALS.

As for cohort 2, FIG. 4, panels C to F are line graphs summarizing the results of hanging test, rotarod test, rearing activity and traveling activity, respectively, for wildtype and transgenic ALS mice treated with saline, and ALS mice treated with lithium benzoate during the test period. The data demonstrated that the motor functions of ALS mice treated with lithium benzoate were improved, as compared to their control littermate from about 133 days of age until about 147 days of age. These results suggest that the lithium benzoate treatment improves motor functions and/or alleviate coordinated motor function deficit during disease progression of SOD1$^{G93A}$ transgenic mice. Thus, lithium benzoate is expected to show therapeutic efficacy or delay the progression of motor function deficit in ALS.

The Weight Change and Survival Rate of Lithium Benzoate Treated SOD1 Transgenic Mice As shown in FIG. 4, panels G and H, the weight change and the proportion of mice surviving over time of the ALS mice treated with lithium benzoate were also improved as compared with the ALS mice treated with vehicle.

Example 4: Lithium Benzoate Protects the Primary Cortical Neurons from the Oxygen and Glucose Deprivation Brain injuries in central nervous system (CNS) result from poor blood flow and glucose supply to the brain tissues in a variety of conditions including ischemic/hemorrhagic stroke, vascular dementia, seizure, traumatic brain injury (TBI), spinal cord injuries and infection, etc. The disability and even death following the brain injuries are common. Although the mortality has been decreased in the recent decades; the disability is still intractable. Novel therapies to protect, repair neurons, or develop the neuroplasticity are in need for patients suffering from or at risk for brain injuries.

Materials and Methods

Preparation of Primary Culture and OGD Model

The oxygen-glucose deprivation (OGD) is a common and well-validated cell model used for brain injuries like stroke-related studies. Primary cortical cultures were prepared as previous described. To induce the OGD model, the Neurobasal medium supplemented with B27 (GIBCO/Life Technologies of Thermo Fisher Scientific Corporation) was removed from the cultures, and then rinsed with Neurobasal-A Medium (no D-glucose and sodium pyruvate [GIBCO/Life Technologies of Thermo Fisher Scientific Corporation]). The cultured cells were maintained in a humidified incubator at 37° C. with 5% $CO_2$ for 1 h to consume the resting glucose and pyruvate. The cultures were then subjected to an anaerobic environment of 95% $N_2$-5% $CO_2$ for 4 hours. Oxygen concentration was monitored by an oxygen analyzer (Proox-110, Demott St, Lacona, N.Y., USA), as maintained at approximately 1.0% throughout the experiment.

Drugs Application

Figure 5:
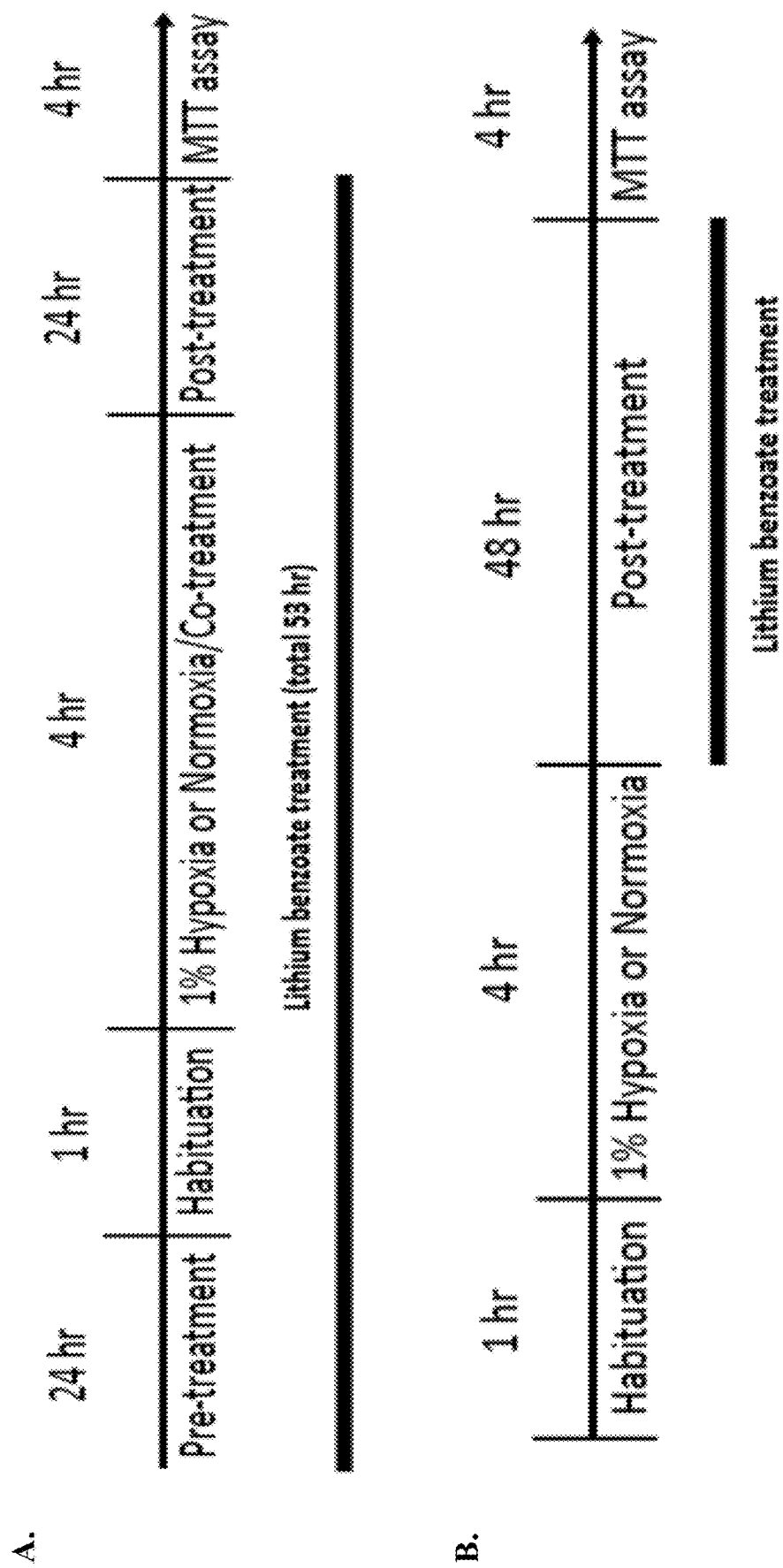
FIG. 5 includes diagrams showing exemplary experimental designs. A: an exemplary experimental design of lithium benzoate treatment for 53 hours on primary cortical culture (solid bar). B: an exemplary experimental design of lithium benzoate post-treatment for 48 hours on primary cortical culture (solid bar).

Cortical culture was treated with lithium benzoate with different conditions, including: (1) the overall treatment of lithium benzoate (0, 0.3, 1, 3, 5 mM) for 53 hours (including pre-treatment 24 hours, habituation 1 hour, oxygen-glucose deprivation 4 hours, and post-treated reperfusion 24 hours) (FIG. 5, panel A); (2) the post-treatment of lithium benzoate (0, 0.3, 0.5, 1, 3, 5 mM) for 48 hour reperfusion (FIG. 5, panel B).

MTT Assay

MTT assay was used to assess the extents of cell survival. MTT (3-(4,5-dimethylthiazol-2-yl)-2,5-diphenyltetrazolium bromide) was added to the culture, incubated at 37° C. for 4 hours. Insoluble purple formazan products were yield by living cells. The colorimetric method was used to quantify the surviving cells, and "cell survival (%)" was defined as the mean numbers of surviving cells.

Results

The Cell Survival of Lithium Benzoate Treated-Primary Cortical Culture

Figure 6:
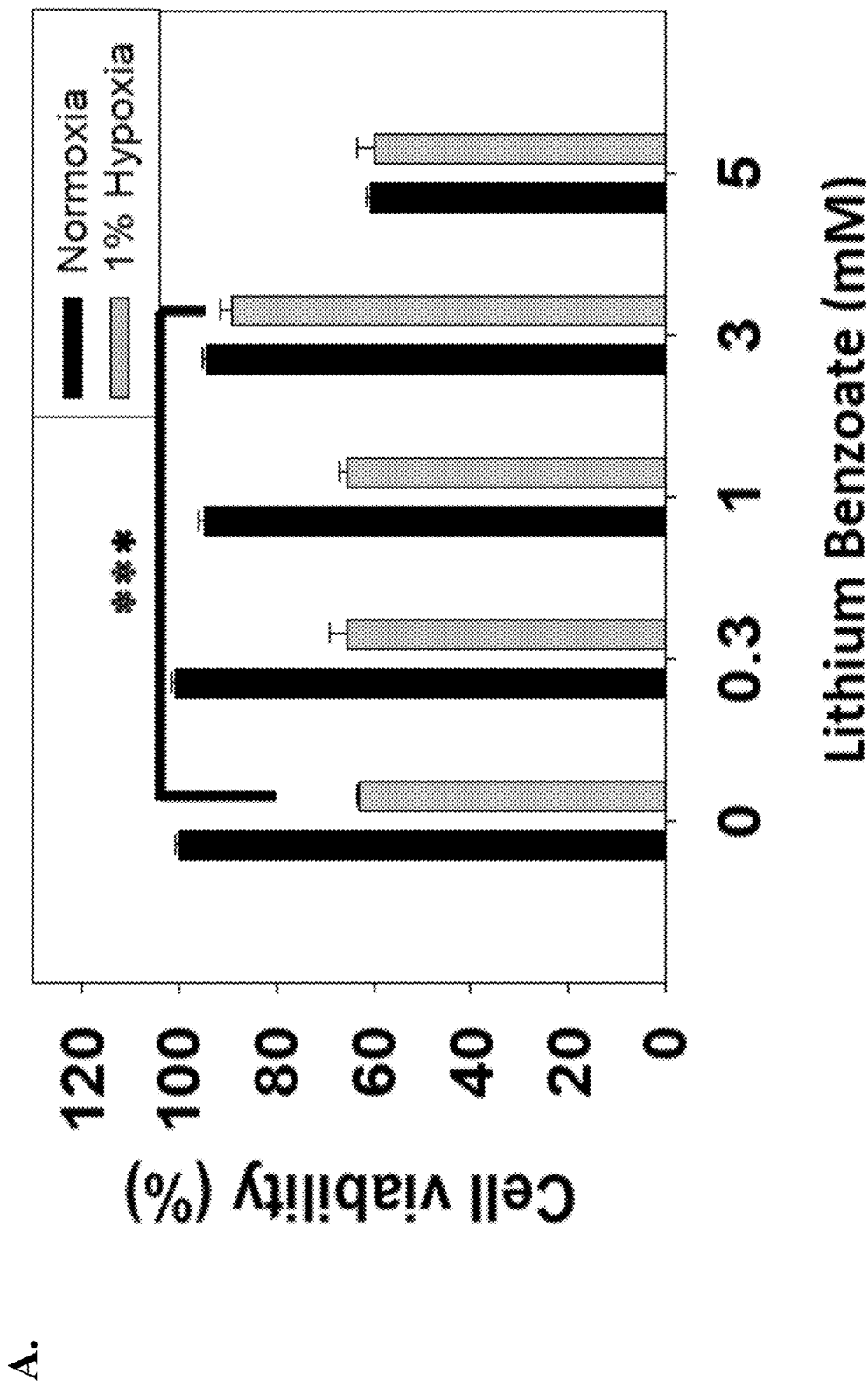
FIG. 6 includes diagrams showing that lithium benzoate protected primary culture neurons from oxygen and glucose deprivation. A: a graph showing cell viability of primary cortical culture treated with lithium benzoate (0, 0.3, 1, 3, 5 mM) for overall 53 hour protection. * $p$-value $<0.001$. B: a graph showing cell survival (%) of primary cortical culture treated with lithium benzoate (0, 0.3, 0.5, 1, 2, 3 mM) for 48 hours.  $p$-value $<0.01$; * $p$-value $<0.001$; ** $p$-value $<0.0001$.
Figure 6:
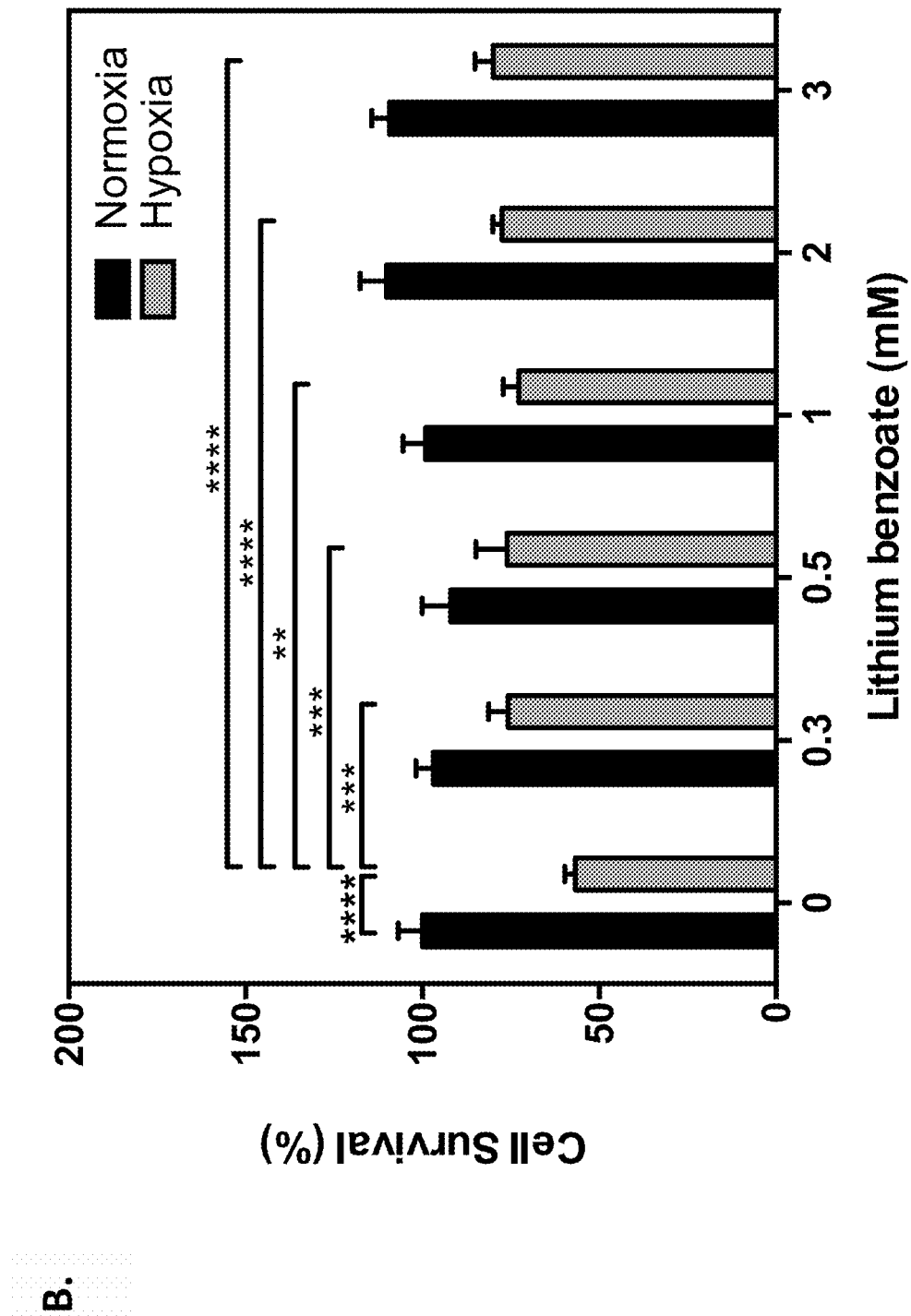

As shown in FIG. 6, panel A, the cell survival of primary cortical cells was reduced about 50% under oxygen-glucose deprivation, while the treatment of lithium benzoate, including before the deprivation for overall 53 hours (FIG. 5, panel A), and post-oxygen & glucose deprivation for 48 hours (FIG. 5, panel B), significantly protected primary cortical cells from death. According to the result in FIG. 6, panel B, lithium benzoate exhibited cell protection effect at all dose levels.

The protection of cell survival on OGD cortical culture by lithium benzoate indicates its potential therapeutic effect on brain injuries, including ischemic/hemorrhagic stroke, vascular dementia (VD), traumatic brain injury (TBI), seizure disorders and spinal cord injuries as well.

Example 5: Lithium Benzoate Reduces Cell Death and Behavioral Disability from MPTP Toxicity Parkinson's disease (PD) is a progressive neurodegenerative disorder primarily due to damage to the nigrostriatal dopaminergic pathway. In this example 1-methyl-4-phenyl-1,2,3,6-tetrahydropyridine (MPTP) was used to produce pathological changes similar to human idiopathic Parkinson's disease in both cell and animal model.

Materials and Methods

Cell Culture and Drug Application

Figure 7:
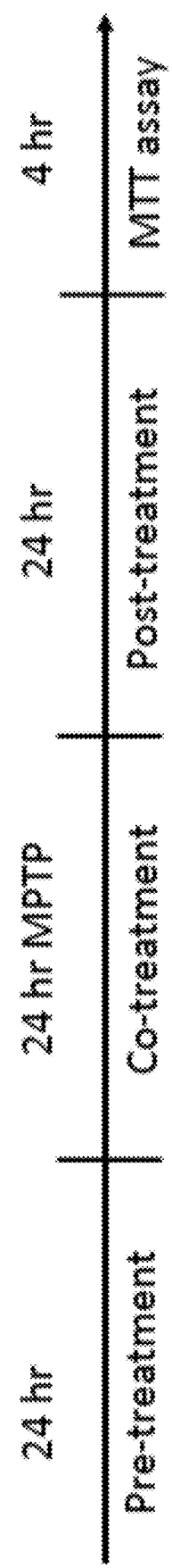
FIG. 7 is a diagram showing an exemplary experimental design of lithium benzoate and sodium benzoate treatments with different conditions on primary cortical culture treated with 1-methyl-4-phenyl-1,2,3,6-tetrahydropyridine (MPTP).

SH-SY5Y, the human neuroblastoma cell line, was incubated with MPTP (750 μM) for 24 hrs. Lithium benzoate/sodium benzoate (0, 0.3, 1, 3 mM) was treated with different conditions on SH-SY5Y cells, including pre-treatment for 24 hours, pre-treatment and co-treatment for 48 hours, and 24 hour post-treatment (FIG. 7). MTT assay was used to assess the extents of cell survival as previous described.

Animal Model and Drug Regimens

Animals were housed and kept in the same condition as previous described. Male C57BL/6J mice (age: 12 weeks) were randomly assigned to 2 groups—vehicle control and MPTP-induced groups. The mice of MPTP-induced group were intraperitoneally injected with MPTP (30 mg/kg body weight/day) for five weeks, while those in the vehicle control group received injections of the same volume of saline. After 5 weeks of MPTP exposure, pole test was performed to elucidate the effect of MPTP-induced disability. The mice with behavioral disability were randomly divided into two groups with different treatment of saline and lithium benzoate (256 mg/kg body weight/day).

Behavioral Task

Pole test was used to measure the degree of bradykinesia, a typical symptom of parkinsonism. The animals were positioned head upward near the top of a rough-surfaced pole (1 cm in diameter and 60 cm in height). The time taken until they turned downward (Tturn) and the total time taken to climb down to the floor (TLA), were recorded. When the mouse was not able to turn downward, Tturn was taken as 60 seconds (default value). TLA was taken as 120 seconds when the mouse failed to turn and dropped from the pole.

Results

Figure 8:
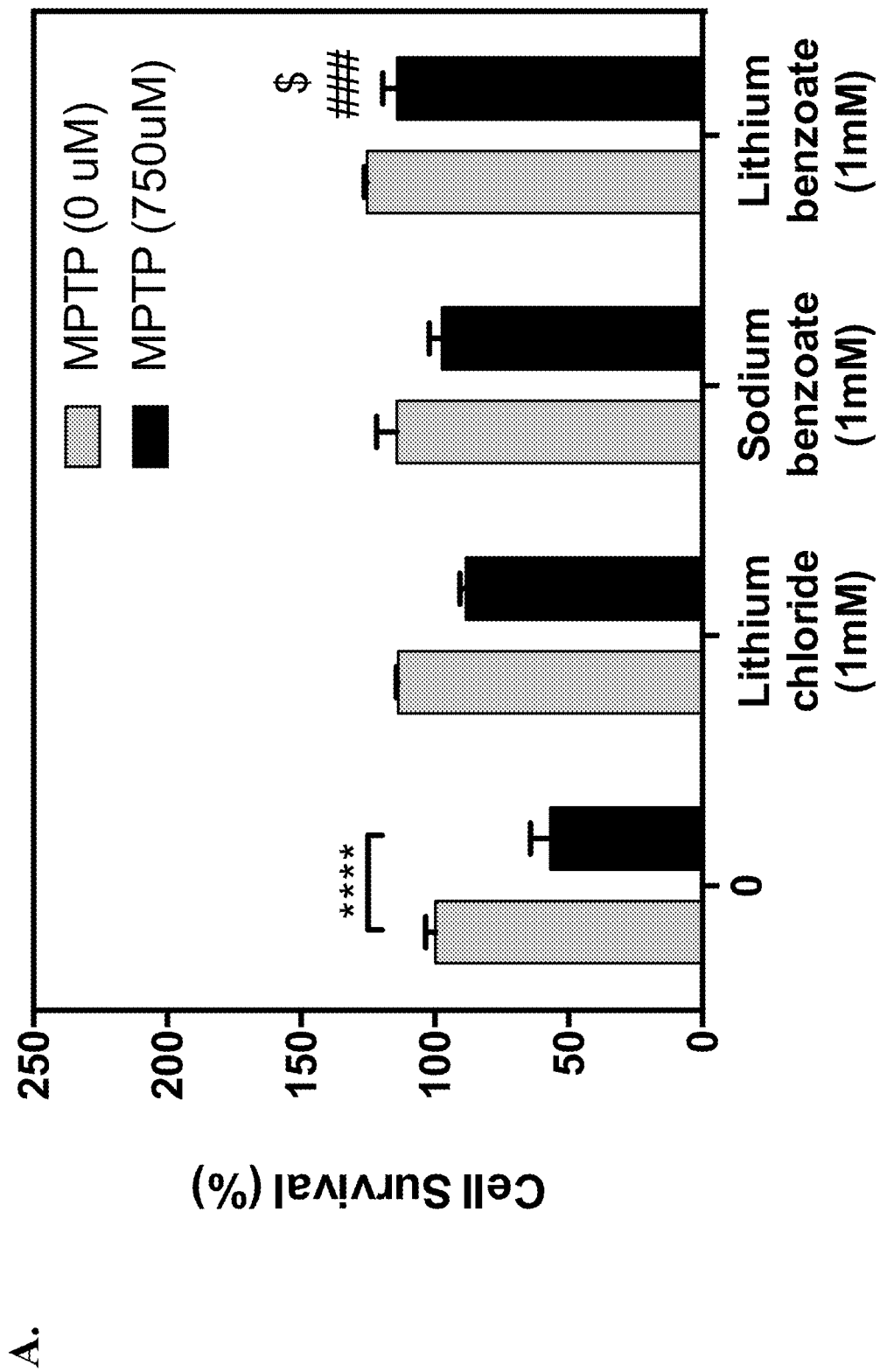
FIG. 8 includes diagrams showing the cell survival rate (%) of primary cortical culture exposed to MPTP. A: a diagram showing survival rates of cells pre-treated for 24 hours with 1 mM lithium chloride, 1 mM sodium benzoate and 1 mM lithium benzoate. B: a diagram showing survival rates of cells 24 hours after treatment with 1 mM lithium chloride, 1 mM sodium benzoate and 1 mM lithium benzoate. Lithium benzoate provides better protection than sodium benzoate and lithium chloride. ****: $p$-value $<0.0001$; $ indicated the comparison between lithium benzoate and sodium benzoate, $: $p$-value $<0.05$; # indicated the comparison between lithium benzoate and lithium chloride, ###: $p$-value $<0.001$.
Figure 8:
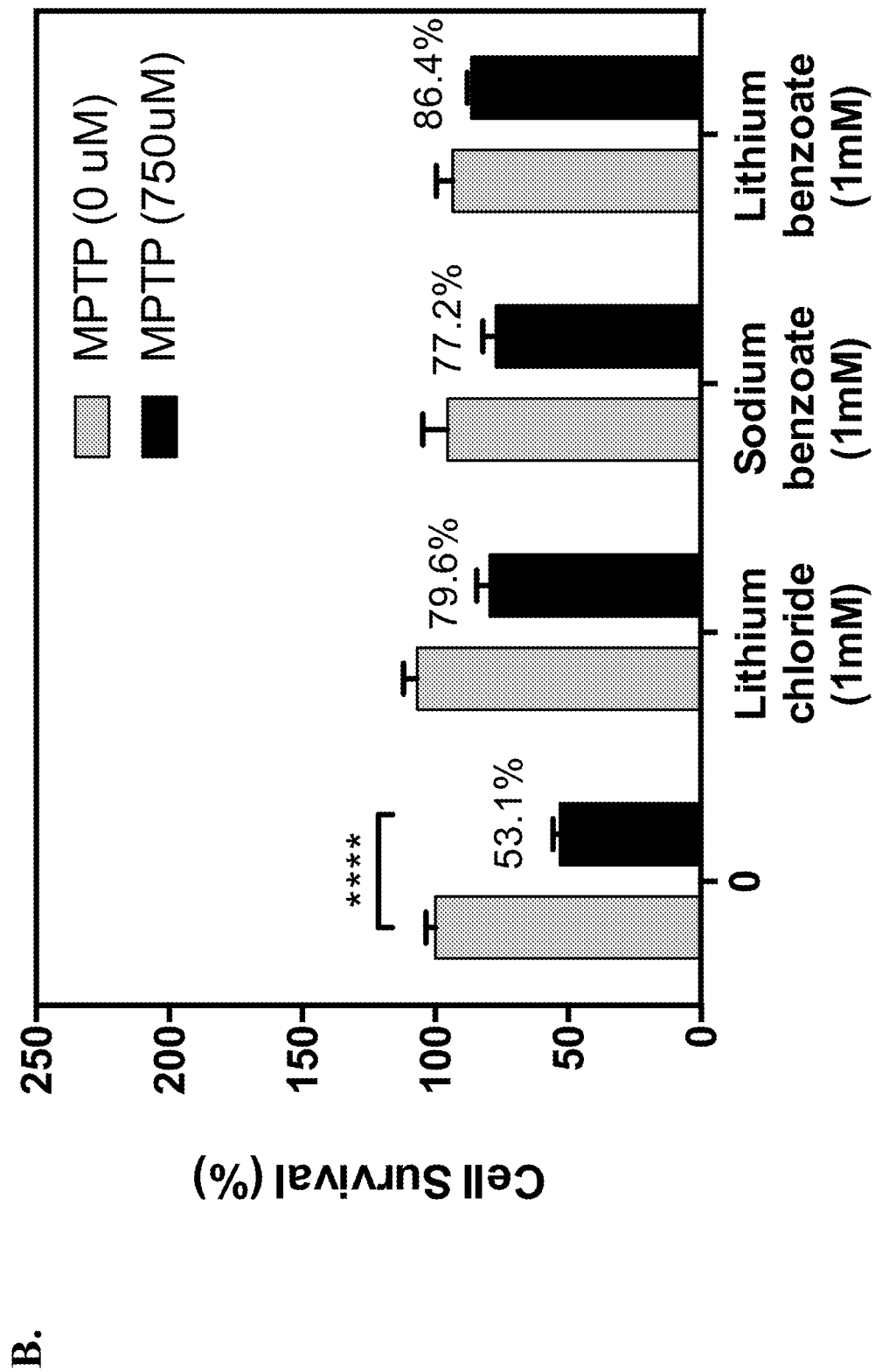
Figure 9:
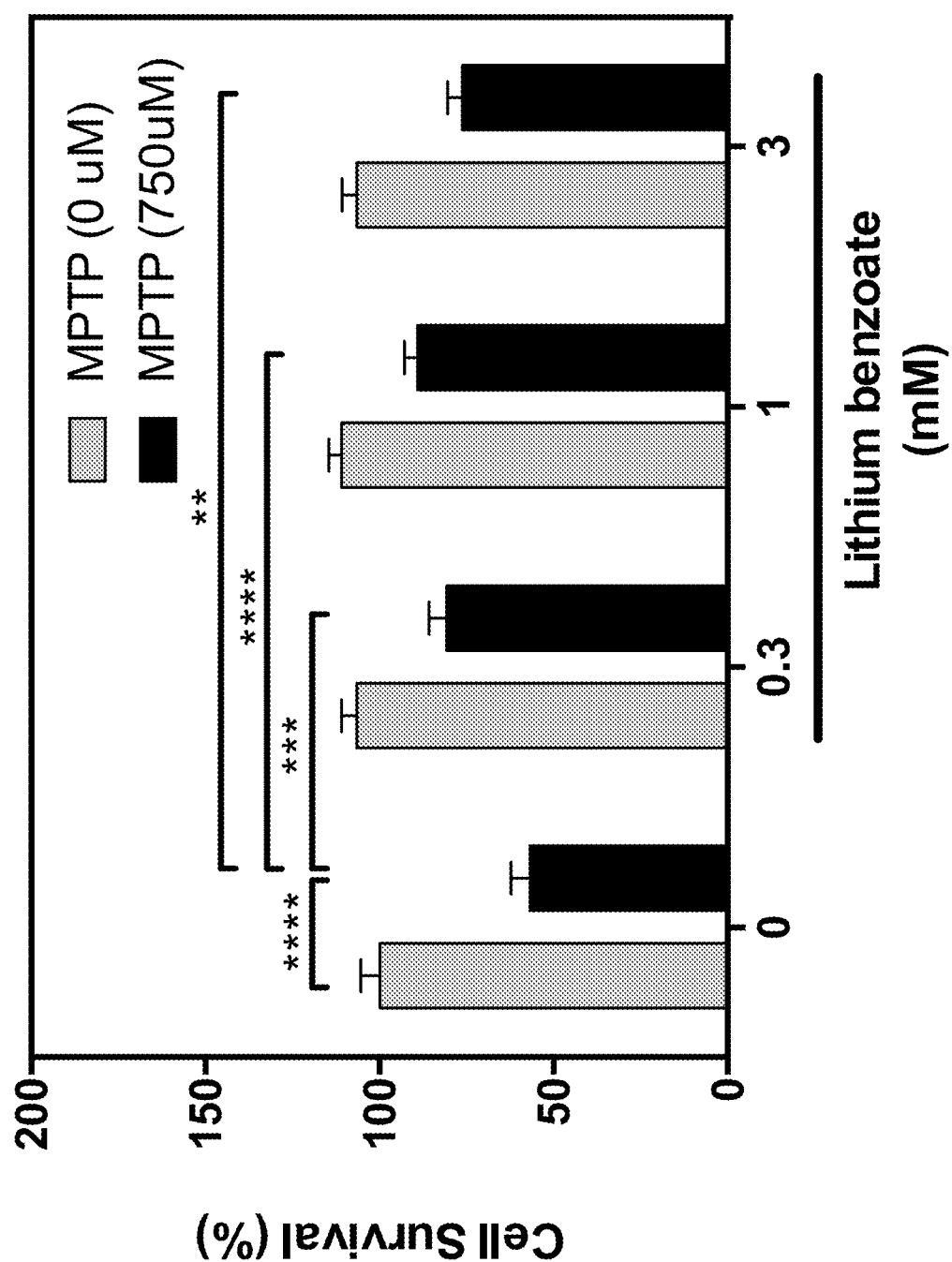
FIG. 9 is a chart showing comparison of cell survival (%) under MPTP treatment by the protection of different concentrations of lithium benzoate (0.3, 1, 3 mM). * $p$-value $<0.05$;  $p$-value $<0.01$; * $p$-value $<0.001$; **** $p$-value $<0.0001$.

The Effect of Lithium Benzoate Treatments on Primary Cortical Culture Exposed with MPTP As shown in FIG. 8, MPTP (750 µM) exposure caused about 50% of cell number reduction. Pre-treatment and post-treatment of all drugs for 24 hours could significantly protect SH-SY5Y cells from MPTP-induced cell death. Comparison the protective effect of lithium benzoate (1 mM), sodium benzoate (1 mM) and lithium chloride (1 mM), lithium benzoate had better performance of cell survival improvement than the other two groups (FIG. 8, panels A-B). For lithium benzoate, this effect was most obvious at the dose of 1 mM (FIG. 9, $p<0.0001$).

The Effect of Lithium Benzoate Treatments on MPTP Toxicity-Induced Mice

Figure 10:
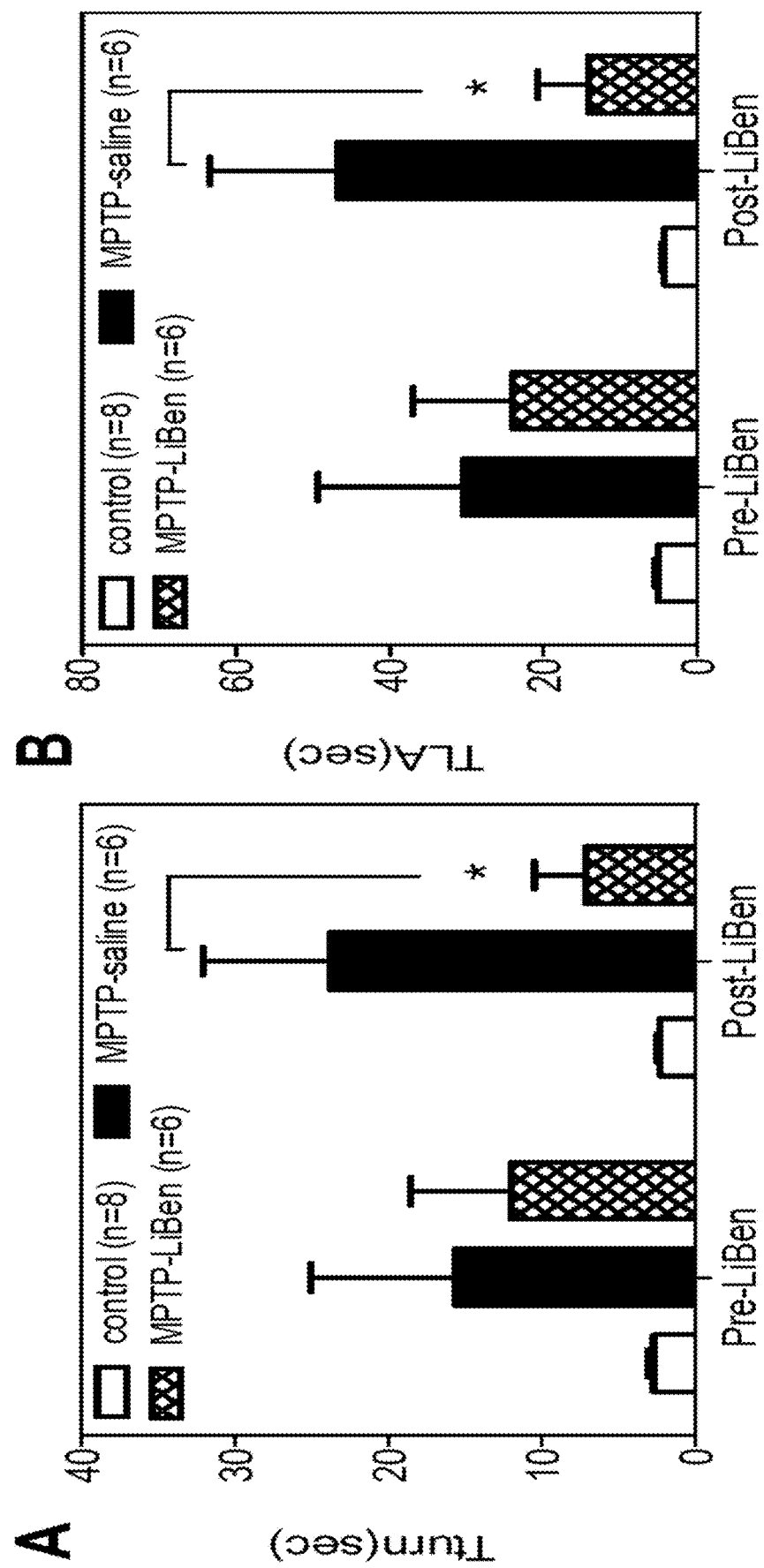
FIG. 10 includes diagrams showing the pole test performance of turning time (panel A) and total time spent on the pole (panel B) of mice treated with control, MPTP-saline, and MPTP-LiBen. LiBen substantially improves the MPTP-induced deficits. Results are mean±SEM.* $p$-value $<0.05$ (t-test).
Figure 11:
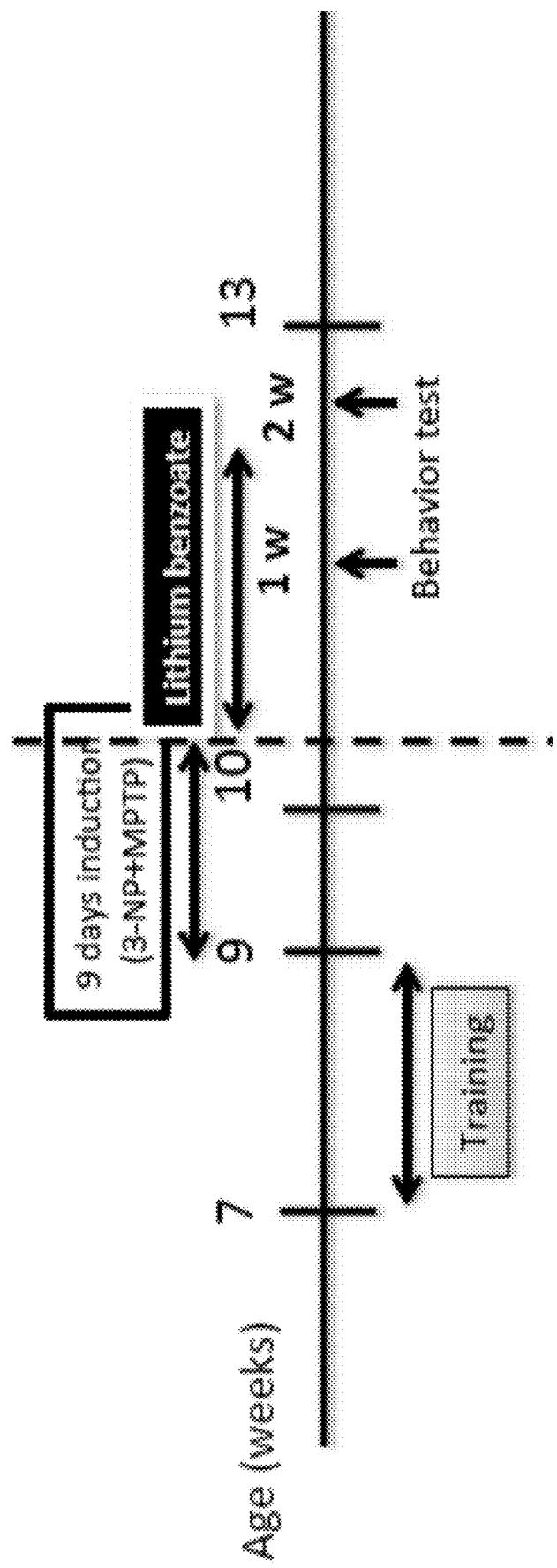
FIG. 11 is a diagram showing an exemplary experimental design of treatment regimen of lithium benzoate on MPTP and 3-NP double toxicity-induced mice of MSA model.

The performance of pole test was recorded before and after the drug treatments. Prior to the MPTP injection, all mice were trained on the pole for a week. The data in FIG. 10, panels A-B demonstrate that the MPTP-induction resulted in longer turning time (Tturn) and the total time for turning down (TLA), whereas the treatment of lithium benzoate significantly reduced both the turning time (Tturn) and the total time for turning down (TLA). The performance of pole test on MPTP-induced mice improved with the regimen of lithium benzoate while becoming sores without lithium benzoate treatment.

These results indicate that the lithium benzoate treatment can rescue the MPTP-induced cell death and behavioral disability, and hence, lithium benzoate can be a therapeutic agent for Parkinson's disease.

Example 6: Lithium Benzoate Reduces Disability Induced by MPTP Plus 3-NP Intoxication Striatonigral degeneration (SND) is a Parkinsonism associated with multiple system atrophy (MSA-P), due to the combined degeneration of dopaminergic neurons in the substantia nigra pars compacta (SNc) and striatal output neurons. SNc displays a specific sensitivity to the inhibition of mitochondrial complex I by MPTP. 3-Nitropropionic acid (3-NP), on the other hand, is an inhibitor of mitochondrial respiration by irreversible inhibition of succinate dehydrogenase (SDH) and induces selective lesions of the striatum in most species. To reproduce the neuropathological hallmarks of SND/MSA-P, "double toxin-double lesion", which combined MPTP plus 3-NP intoxication, in C57BL/6 mice has been established.

Materials and Methods

Animal and Housing Conditions

Male C57BL/6J mice (age, 8-12 weeks) were randomly assigned to 2 groups—vehicle control and MPTP/3-NP-induced groups. MPTP and 3-NP were administered during a 9-day intoxication period. 3-NP was administered i.p. every 12 h (total dose 450 mg/kg in 9 days) and MPTP i.p. at 10 mg/kg/day (total dose 90 mg/kg in 9 days). After 9 days of MPTP/3-NP intoxication, mice performed with more than 20% reduction of rotarod were randomly divided into two groups with treatment of either saline or lithium benzoate (256 mg/kg body weight/day) for one week.

Animal Behavioral Task

Rotarod motor activity was measured before and after chronic MPTP/3-NP induction, respectively. Time spent on the rod at each level of revolving speed indicated motor performance. Mice were trained at the speed accelerating from 4 to 10 rpm over 5 min before the test (−7, −5, −3 Days). During the test, all animals started at 4 rpm and accelerated from 4 to 20 rpm over 5 min with each mouse experiencing three trials per day with inter-trial interval of 10 min. The average latency time of each mouse to fall is calculated. Mice were tested at 1- or 2-week intervals and did not require retraining.

Results

Figure 12:
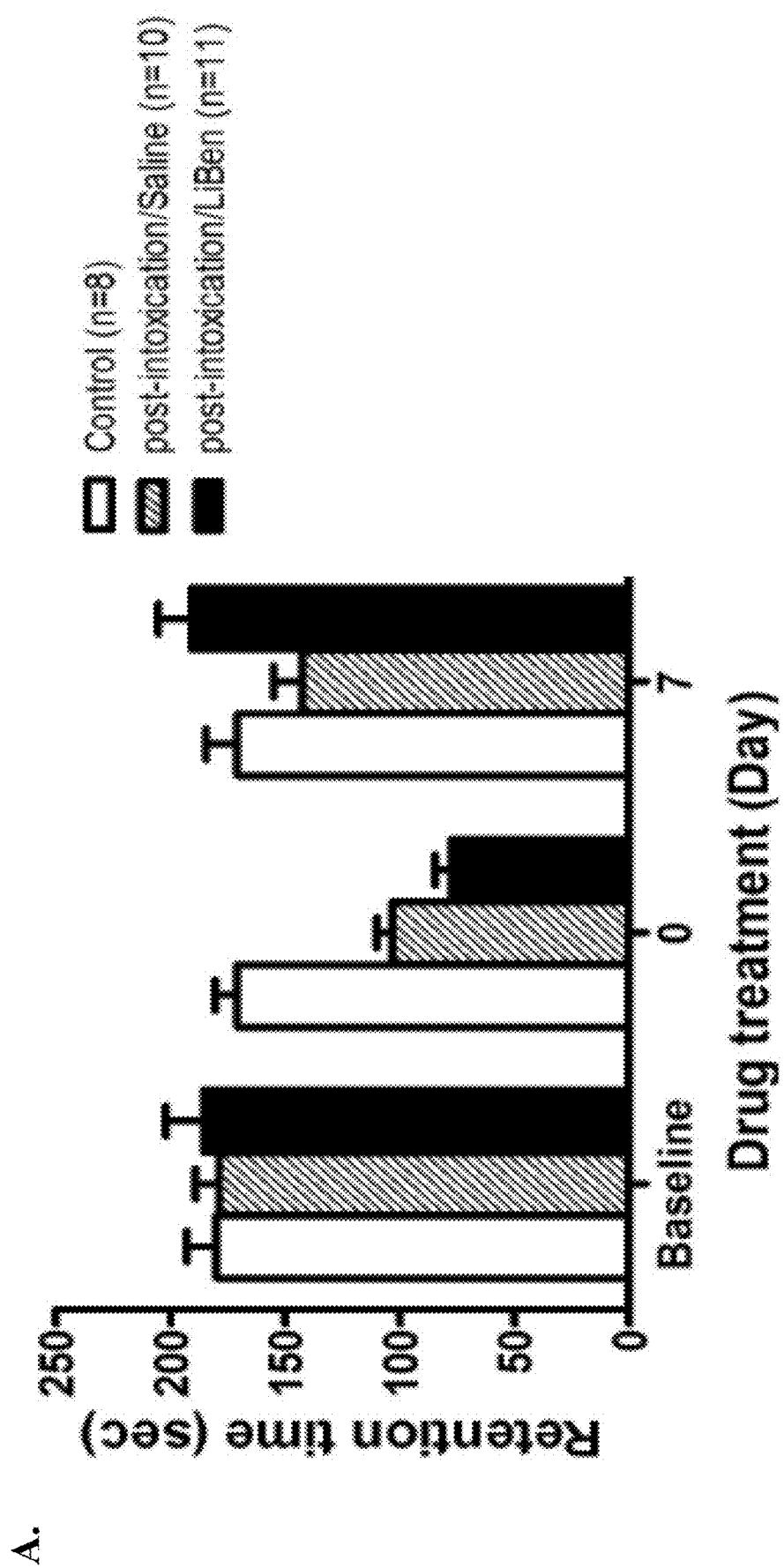
FIG. 12 includes charts showing the effectiveness of lithium benzoate on performance of rotarod on mice exposed to both MPTP and the 3-NP mouse model of MSA. A: a diagram showing retention time on the rod of baseline (no treatment), 0 day (after 9 days of MPTP plus 3-NP induction), and 7 days (with lithium benzoate or saline treatment for 7 days) in different groups as indicated. B: a diagram showing improvement of rotarod retention time in different groups after 7 days of treatment with lithium benzoate for 7 days. Results are mean±SEM. * $p$-value $<0.05$.
Figure 12:
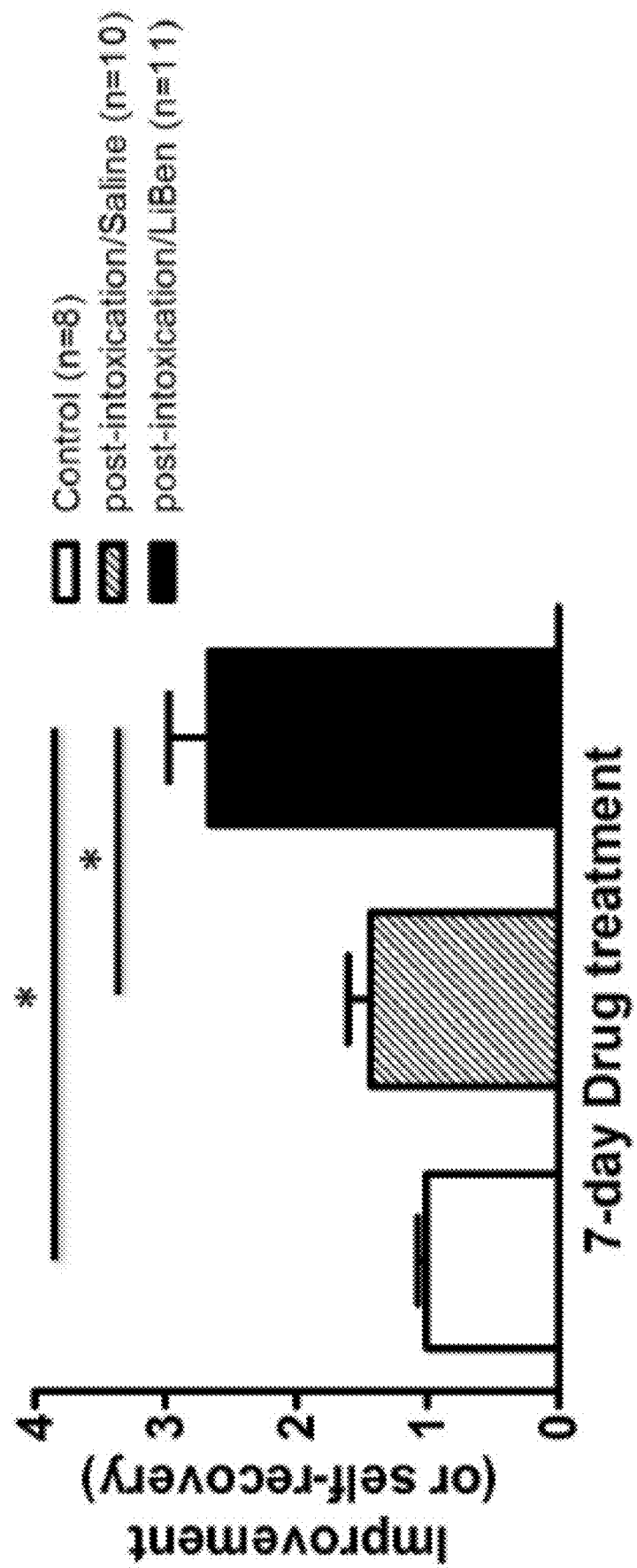

The Performance of Rotarod on MPTP Plus 3-NP Exposed Mice with Lithium Benzoate Treatment As shown in FIG. 12, panels A-B, the retention time on rotarod of mice with 9 days of MPTP plus 3-NP exposure was significantly reduced compared to its baseline or control group. The improvement on FIG. 12B was calculated as retention time (sec) of the $7^{th}$ day treatment divided by the $0^{th}$ day treatment. After one week of lithium benzoate treatment, the retention time on rod of MPTP/3-NP post-intoxicated mice were significantly improved compared to those treated with saline, which demonstrated its potential therapeutic effect on Striatonigral degeneration diseases, especially MSA-P.

Example 7: Lithium Benzoate Alleviates the Suffering from Acute Pain

Pain is a serious clinical problem that affects the quality of patient's life. The International Association for the Study of Pain (IASP) defines pain as an unpleasant sensory and emotional experience associated with actual or potential tissue damage, or described in terms of such damage (IASP 1979). Multiple animal models of pain are developed for relevant clinical conditions to investigate their mechanisms and treatments.

Figure 13:
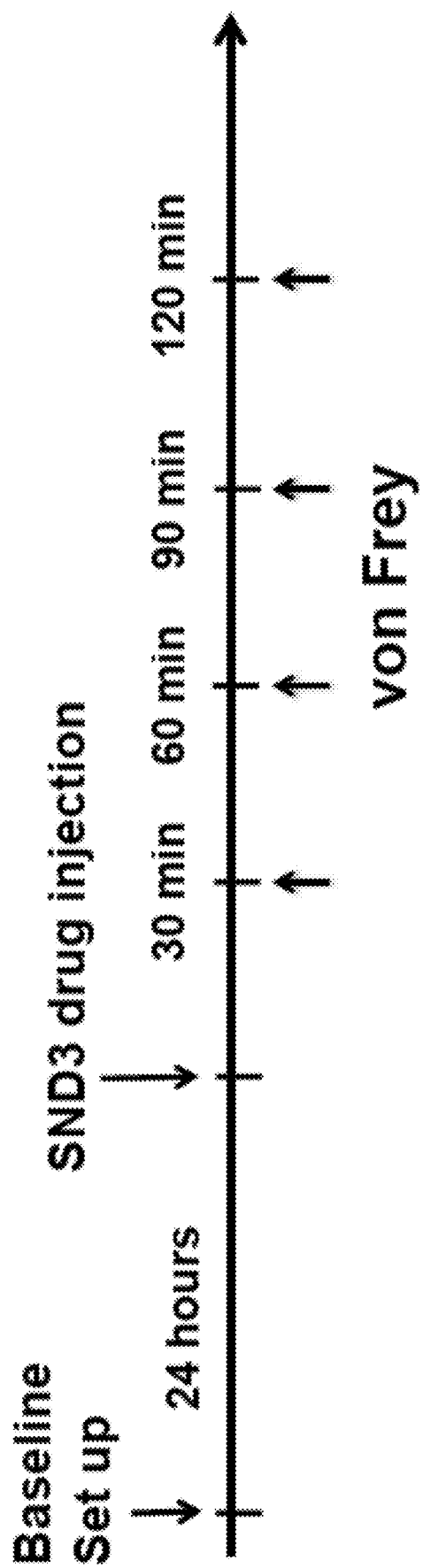
FIG. 13 is a diagram showing an exemplary experimental design for investigating the effect of lithium benzoate on relieving acute pain.

In this example, the procedure of acute pain management was applied to examine the effect of lithium benzoate on animal. The experimental designed is shown in FIG. 13. The baseline of Von Frey mechanical threshold for each mouse was tested 24 hours before lithium benzoate treatment. Then, after the lithium benzoate injection, Von Frey would be tested at the time point of 30 min, 60 min, 90 min, and 120 min.

Materials and Methods

Animal and Drug Administration

Animals are housed and kept in the same condition as previous described. Male C57BL/6J mice (age, 8 weeks) were randomly assigned to 2 groups, PBS control (n=10) and lithium benzoate (n=10) group. Each mouse in lithium benzoate group was intraperitoneally injected at a dose of 256 mg/kg, whereas the mice in PBS control were received injections of the same volume of PBS.

Animal Behavioral Tasks

The Von Frey test is used to assess mechanical nociception. A mouse is placed in a small box (10 cm×6 cm×10.5 cm) on a confined area of wire mesh (65 cm×21 cm×31 cm) (2450 Electronic Von Frey Anesthesiometer, IITC, U.S.A.). The mouse was kept in the box for 60 min to acclimatize. When the tested mouse calms down, a special tip with electrode inside was used to poke its hind paw. Force was slowly increased to poke the mouse, and measure the mechanical threshold that induces a withdrawal response.

Results

The Antinociceptive Effect of Lithium Benzoate

Figure 14:
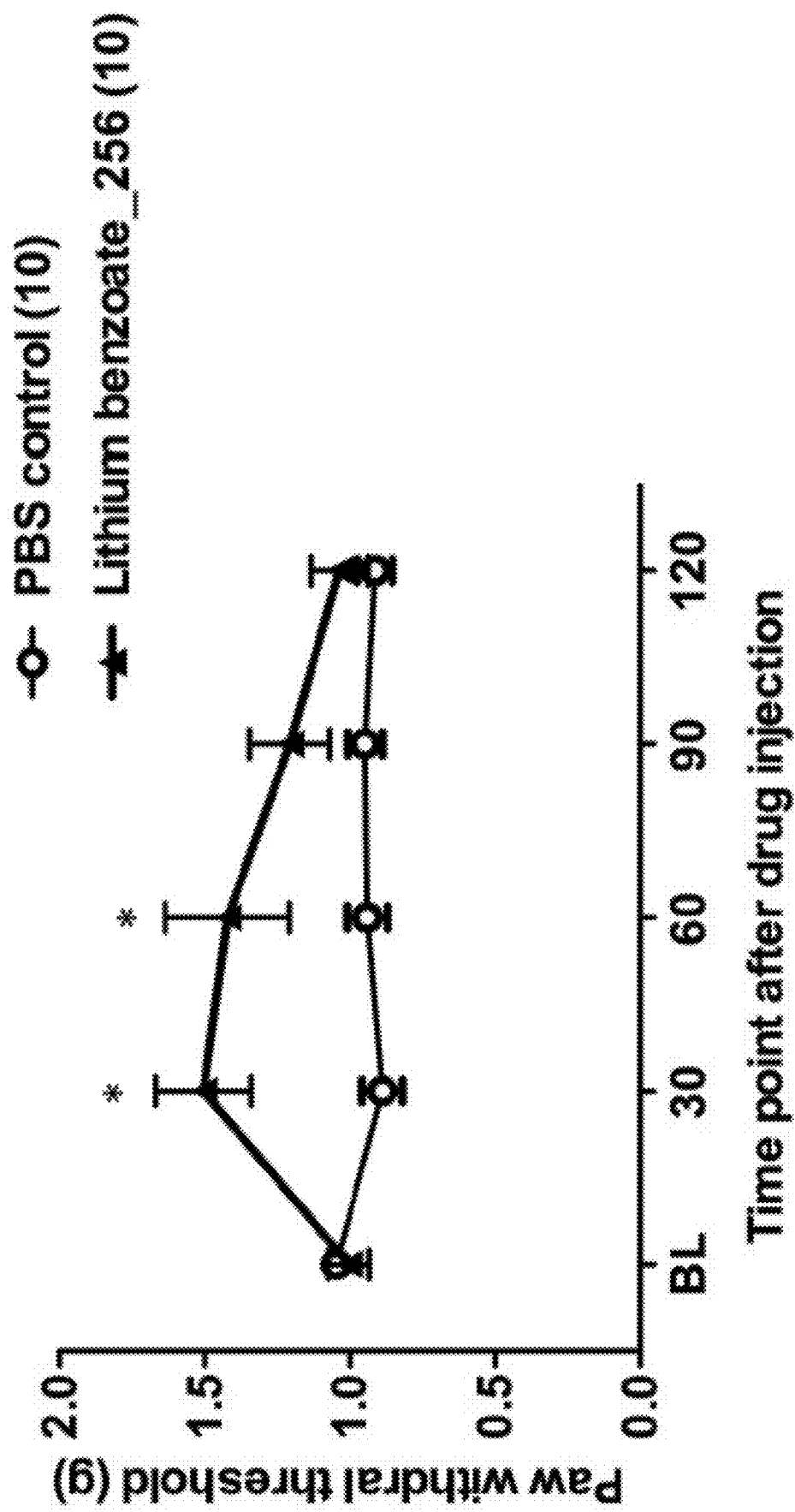
FIG. 14 is a line chart showing different time point of paw withdrawal thresholds after lithium benzoate or PBS control treatment on Von Frey task. Results are mean±SEM. * p-value <0.05 (t-test). Two-way ANOVA analysis showed no interaction of time-dependent results. Student's t-test was analyzed PBS versus Liben at each time point. LiBen group shows better pain threshold at both 30 and 60 minutes.

As shown in FIG. 14, the pre-administration of lithium benzoate alleviated the acute mechanically evoked pain examined by Von Frey test. This effect was obvious after 30 min of administration and lasted till 60 min. Von Frey test measures cutaneous hyperalgesia or allodynia, mimicking the clinical conditions such as neuropathic pain, postoperative pain, inflammation, or osteoarthritis. Therefore, lithium benzoate can be used to treat patients suffer from these types of pain.

Example 8: Lithium Benzoate has Better Bioavailability to Raise Benzoate than Sodium Benzoate In this example, the in vivo pharmacokinetics of lithium benzoate and sodium benzoate was compared.

Materials and Methods

Animal and Drug Administration

Male Sprague-Dawley rats weighed between 240-260 g were randomly assigned to two groups. Group1 rats (n=6) were treated with a single dose of sodium benzoate (NaBen, 287.9 mg/kg) and lithium carbonate ($Li_2CO_3$, 74.2 mg/kg), whereas Group2 rats (n=6) were treated with lithium benzoate (LiBen, 255.3 mg/kg). These two regimens would provide the same molarity of lithium and benzoate. The chemicals were dissolved in PBS, and then administrated by oral gavage. All rats were fasted overnight with free access to water before experiments. After single dose administration of drugs, the blood samples were then collected at the time point 0, 5, 15, 30, 60, 90, 120, 240, 360, 720, and 1440 min.

Plasma Sample Collection

Blood samples were collected in tubes coated with sodium heparin from jugular vein catheterized rats. Then, the blood samples were kept on ice and centrifuged at 2,500×g for 15 min at 4° C. The supernatant was collected and then kept frozen at −80° C. until further processing.

Benzoic Acid Quantification

The plasma concentration of benzoic acid was determined by LC/MS/MS. The chromatographic separation was carried out on a ODS 5 um column (4.6×150 mm, Biosil). The mobile phase consisted of a mixture of 1% mobile phase A and 99% mobile phase B. The mobile phase A contains acetonitrile (ACN)/$H_2O$/1M $NH_4HCO_3$=25/75/0.5 (v/v); the mobile phase B contains $H_2O$/1M $NH_4HCO_3$=100/0.5 (v/v). The eluent had a flow rate of 1 ml/min. The injection volume was 50 μL and the column temperature was 23° C. All solvents were HPLC grade quality.

Data Analysis

Plots of plasma concentration of benzoic acid versus time are constructed. The fundamental pharmacokinetic parameters were obtained from non-compartmental analysis (NCA) of the plasma data using WinNonlin.

Results

The Plasma Concentration of Benzoic Acid Versus Time

Peak plasma concentration (Cmax) and time to Cmax (Tmax) of benzoic acid were observed by HPLC analysis. The $T_{1/2}$, area under curve (AUC) and other pharmacokinetic parameters were calculated. As shown in FIG. 15, panels A-B and Table 1 below, the Cmax of benzoic acid following the single administration of NaBen and $Li_2CO_3$ (Group1) was 71,378 ng/ml at 0.139 hr, and the administration of LiBen (Group2) was 109,321 ng/ml at 0.19 hr, respectively. Benzoic acid in both groups was quickly reached the peak in plasma around 10 min (FIG. 15). For the AUCInf (area under the plasma concentration-time curve from time zero to infinity) value, 41,577 hr*ng/ml was calculated in Group1, and 62,874 hr*ng/ml was in Group2. Further, benzoic acid was observed to be quickly removed from plasma with a half-life of 1.45 hr in Group1 rats (NaBen+$Li_2CO_3$), and 2.52 hr in Group2 rats (LiBen). Both plasma concentration in Group1 and 2 were eliminated to approximate zero at the time point of 12 hr. Consequently, it's an unexpected finding that the Cmax, AUC and $T_{1/2}$ values of benzoic acid in LiBen were much higher than those from NaBen+$Li_2CO_3$, which means LiBen treatment has better bioavailability in releasing more benzoic acid to the plasma, producing better exposure of the body.

TABLE 1

Parameters of benzoic acid pharmacokinetics

| | $T_{max}$ (hr) | $C_{max}$ (ng/mL) | $T_{1/2\ (h)}$ | AUClast (hr * ng/mL) | AUCInf (hr * ng/mL) | AUC Extr (%) | MRT (h) | AUC/D (h * kg * ng/ml/mg) |
|---|---|---|---|---|---|---|---|---|
| NaBen + Li2CO3 | 0.139 | 71,378 | 1.46 | 39,201 | 41,577 | 7.76 | 1.68 | 110.8 |
| LiBen | 0.19 | 109,321 | 2.52 | 62,059 | 62,874 | 2.63 | 0.75 | 245.1 |

The Plasma Kinetics of Lithium

Plasma lithium concentration was detected by ICP-MS. As shown in FIG. 16 and Table 2 below, the Cmax of lithium of Group2 (LiBen) was significantly higher than Group 1 (NaBen and $Li_2CO_3$), moreover, the AUC was also higher in LiBen than in NaBen+$Li_2CO_3$. Overall, Liben has a better pharmacokinetic profile than the combination of NaBen+$Li_2CO_3$.

TABLE 2

Parameters of lithium pharmacokinetics

| | $T_{max}$ (min) | $C_{max}$ (mM) | $T_{1/2}$ (h) | $AUC_{0 \rightarrow t}$ |
|---|---|---|---|---|
| NaBen + Li2CO3 | 222.5 | 0.906 | 539.68 | 605.87 |
| LiBen | 132.5 | 1.717 | 469.62 | 620.59 |

Example 9: Lithium Benzoate Protects Primary Cortical Neurons from Amyloid-beta Damage Aβ is the major neurotoxic component in the senile plaques observed in the brains of Alzheimer's disease (AD) patients. The synthetic Aβ25-35 is also known to cause mitochondrial dysfunction. Therefore, in this example, lithium benzoate was used to explore the potential cytoprotective actions against Aβ25-35 in primary cortical culture. In addition, the effects of sodium benzoate and lithium chloride on the same condition were also examined, revealing the extraordinary potential efficacy of lithium benzoate on Alzheimer's disease.

Materials and Methods

Primary Cortical Culture and Drug Application

Primary cortical cultures were prepared as previous described. Aβ25-35 (Cat. No. A4559, Sigma) was dissolved in autoclaved dd$H_2O$ to make a stock solution of 2 mM, dispensed into aliquots, and immediately stored at −80° C. until use. One day prior to experimentation, aliquots of Aβs were incubated at 37° C. for 24 h to allow aggregation.

Immunocytochemistry

Cells were fixed in 4% PFA and washed in PBS, blocked with 2% bovine serum albumin (BSA) and 0.03% Triton X-100 in PBS, and then incubated with mouse monoclonal antibody against microtubule-associated protein-2 (MAP-2) (Cat. No. MAB378, 1:150, CHEMICON International, Inc., Temecula, Calif., USA); rabbit polyclonal antibody against GFAP (Cat. No. Z0334, 1:600, DakoCytomation Denmark A/S, Denmark). The goat anti-mouse IgG Alexa Fluor-conjugated secondary antibodies (1:500; Cat No. A11003, Thermo Scientific); anti-rabbit IgG Alexa Fluor-conjugated secondary antibodies (1:500; Thermo Scientific) were applied respectively to recognize the primary antibodies of the MAP-2 and GFAP.

Label Cells with BrdU and Immunocytochemistry

Primary cortical cultures were prepared from embryonic day 18 (E18) fetal Spragu-Dawley (SD) rat brains. Culture medium was removed from cells and replace with BrdU labeling solution and incubated at 37° C. for 4 days aligned with treatments after Aβ25-35 for 2 days. Cells were fixed in 4% PFA and washed in PBS, blocked with 2% bovine serum albumin (BSA) and 0.03% Triton X-100 in PBS, acid-washed with 2N HCl and phosphate/citric acid buffer (pH 7.4). Next, anti-BrdU primary antibody (1:250, Thermo Scientific) or anti-NeuN primary antibody (1:300, Abcam) were added. The goat anti-rat IgG Alexa Fluor-conjugated secondary antibodies (1:200; Thermo Scientific); anti-mouse IgG Alexa Fluor-conjugated secondary antibodies (1:500; Thermo Scientific) were applied to recognize the primary antibodies of the BrdU and NeuN respectively.

Fluorescence Microscopy

The coverslips were observed under a digital imaging fluorescence microscope (Olympus BX61; Japan) equipped with filter sets to detect the corresponding fluorescence signals.

Data Analysis

Multiple groups were first analyzed by one-way analysis of variance (ANOVA) followed by a post hoc Student-Newman-Keuls test. P-value of less than 0.05 was considered significant.

Results

Lithium Benzoate Treatment on Cortical Cells Revealed Neuroprotective Effect Against Aft Cytotoxicity Primary cortical neurons were exposed to 10 μM Aβ 25-35 for 2 days, and then followed by treatment of lithium benzoate (1 mM), sodium benzoate (1 mM) or lithium chloride (1 mM) for 4 days. The result of cell survival test was shown in FIG. 17, indicating that exposure of Aβ 25-35 caused large amount of cell death ($p<0.0001$); however, all the drugs show improvement for cortical cells survival. Especially, lithium chloride and lithium benzoate showed statistical improvement compared to no drug treatment, moreover, lithium benzoate significantly reduce the cell death from Aβ 25-35 toxicity much more than the other two drugs ($p<0.0001$).

According to the neuroprotective effect of lithium benzoate, the mechanism to protect cortical cells against amyloid-beta toxicity was examined as follows.

The Neuroprotective Effect of Lithium Benzoate is Not by NMDA Receptor

Firstly, the N-methyl-D-aspartate receptor (also known as NMDA receptor) pathway was studied for lithium benzoate, sodium benzoate and lithium chloride. NMDA receptor is a specific ionotrophic glutamate receptor in neuronal cells, which mediate high calcium permeability. The excitotoxicity caused by excessive calcium influx is considered to be a major mechanism of central neuronal death associated with many neurodegenerative diseases including Alzheimer's disease. Moreover, recent studies indicate NMDA receptor mediated glutamate neurotoxicity may trigger Aβ-induced cell death.

Dizocilpine (also known as MK-801) is an uncompetitive antagonist of NMDA receptor, which has been widely used to study the mechanism of NMDA receptor. In this study, the application of MK801 could reveal whether the neuroprotective effects of drugs were mediated by NMDA receptor. As shown in FIG. 18, panel A, post-treatment of the drugs including lithium benzoate (0.5 mM), and sodium benzoate (1 mM) could elevate the cell survival in cortical cells with Aβ25-35 exposure, whereas this protective effect of sodium benzoate was blocked by MK801 (10 μM) (FIG. 18, panel B). No obvious differences were in lithium benzoate with or without MK801 treatment, which indicated the neuroprotective effect of lithium benzoate were not mediated through the NMDA receptor pathway.

The second part of mechanism study was focused on neurogenesis. The impairment of neurogenesis in the adult hippocampus has been an important evidence of the pathogenesis of Alzheimer's disease. Bromodeoxyuridine (5-bromo-2'-deoxyuridine, also known as BrdU) is a synthetic analog of thymidine, which could replace thymidine during DNA synthesis; therefore, it is commonly used as a marker for cell genesis. In this study, the primary cortical cells with Aβ25-35 exposure were post-conditioning with lithium benzoate, sodium benzoate or lithium chloride at 0.5 or 1 mM for 4 days. The co-localization of NeuN (the neuronal cell marker) and BrdU represents the neurogenesis in cortical culture by immunocytochemistry.

FIG. 19, panels A-C indicated that Aβ25-35 exposure reduced the neurogenesis effect, but all the drugs could reverse this damage. It is obvious that lithium benzoate (0.5 mM) has an unsurpassed performance of neurogenesis ($p<0.0001$), which is extremely greater than the other two drugs.

The GFAP Expression was Reduced in Lithium Benzoate-Treated Cortical Neurons After Aβ25-35 Exposure Glial fibrillary acidic protein (GFAP) is an intermediate filament protein expressed by cells in the CNS, and is also recognized as an astrocyte maturation marker. Upregulation of GFAP, indicating gliosis, is commonly observed after CNS lesion; therefore, expression of GFAP could be useful to understand the state of neurological diseases. In FIG. 20, panels A-B, the exposure of Aβ25-35 in cortical culture increased the number GFAP positive cells ($p<0.0001$), whereas the post-treatment of lithium benzoate (0.5 mM) and lithium chloride (1 mM) significantly reduced this effect. However, sodium benzoate (1 mM) did not influence the GFAP expression under Aβ25-35 exposure. At the same time, LiBen has a better effect than LiCl.

Overall, results from these studies suggest the therapeutic potential of lithium benzoate against Aβ25-35, which was mediated through upregulation of neurogenesis and reduction of GFAP positive cells, but not by NMDA receptor pathway. These effects reveal the efficacy of lithium benzoate to treat Alzheimer's disease.

Example 10: Lithium Benzoate Improves Survival Rate in Huntington's Disease (HD)

Huntington disease (HD) is caused by an expansion of unstable CAG repeats in exon 1 of the huntingtin gene (HTT) that encodes an elongated polyglutamine repeat (polyQ-HTT) (Cell. 1993 Mar. 26; 72(6):971-83). B6CBA-Tg(HD exon1)62Gpb/3J mice (also known as B6CBA-R6/2 mice), which express a transgene that encodes exon 1 of the human mutant HTT, develop a progressive and fatal neurological disease resembling human HD and are used widely to investigate neurodegeneration of HD.

Materials and Methods

Animal and Housing Conditions

Animals used in the examples of the present disclosure were housed in an animal room under temperature control (24-25° C.) and 12:12 light-dark cycle. Standard laboratory chow and tap water were available ad libitum. The experiments procedures were approved by the Institutional Animal Care and Use Committee and were performed in compliance with national animal welfare regulations. Transgenic mice B6CBA-Tg(HDexon1)62Gpb/3J were purchased from the Jackson Laboratory (USA).

The female transgenic and wild-type littermates of both gender were randomly divided into following groups: vehicle (wild-type treated with saline), vehicle-HD (HDexon1transgenic mice treated with saline), drug-HD (HDexon1 transgenic mice treated with lithium benzoate).

Drug Administration

Drug regimen was initiated 11 weeks after birth, and continued until the end of study. Lithium benzoate was intraperitoneally injected at a dose of 256 mg/kg weight/day. The mice of vehicle group received injections of the same volume of saline.

Survival

Date and cause of death were recorded for each mouse. Animals were closely monitored and euthanized if moribund, which was defined as the inability of mice to right themselves 30 seconds after being placed on a side, in accordance with the criteria for severe morbidity. The moribund mice were recorded as "dead", and euthanized using carbon dioxide.

Results

The Survival Rate of Lithium Benzoate Treated HDexon1 Transgenic Mice

Date and cause of death were recorded for each mouse. The survival data were analyzed to investigate any effects of the drug. As shown in FIG. 21, the proportion of mice surviving over time of the HDexon1 transgenic mice treated with lithium benzoate was improved as compared with wildtype and the HDexon1 transgenic mice treated with vehicle.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of protecting cortical neurons from mitochondrial dysfunction, toxicity, or deprivation of oxygen or glucose in a subject, the method comprising administering to a subject in need thereof a solid composition comprising an effective amount of a lithium benzoate compound and a filler excipient, which comprises microcrystalline cellulose, or lactose, wherein the lithium benzoate compound is of the formula:

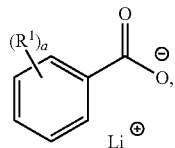

in which R1 is $C_{1-3}$ alkyl or halogen, and a is 0, 1, or 2, wherein the subject has a central nervous system (CNS) disease selected from Huntington's disease, Parkinson's disease, Alzheimer's disease, amyotrophic lateral sclerosis, dementia, or acute pain and wherein the toxicity is associated with oxidative stress, reactive oxygen species overproduction, or both.

2. The method of claim 1, wherein subject is administered with the lithium benzoate compound at about 5 to about 150 mg/kg.

3. The method of claim 1, wherein the lithium benzoate compound is administered by a systemic route.

4. The method of claim 3, wherein the systemic route is oral administration or parenteral administration.

5. The method of claim 1, wherein the subject is administered with the lithium benzoate compound at a frequency of four times a day to one time a month.

6. The method of claim 1, wherein the subject is on another CNS disease treatment or another anti-pain treatment.

7. The method of claim 1, wherein the compound is lithium benzoate.

8. The method of claim 1, wherein the solid composition is a pharmaceutical composition, a medical food, or a health food.

9. The method of claim 1, wherein the solid composition further comprises a lubricant excipient.

10. The method of claim 9, wherein the lubricant excipient is sodium lauryl sulfate, magnesium stearate, talc, calcium stearate, or polyethylene glycol.

11. The method of claim 10, wherein the lubricant excipient is sodium lauryl sulfate or magnesium stearate.

12. A method for treating a central nervous system (CNS) disease, the method comprising administering to a subject in need thereof a solid composition comprising an effective amount of a lithium benzoate compound and a filler excipient, which comprises microcrystalline cellulose, or lactose, wherein the lithium benzoate compound is of the formula:

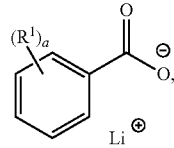

in which R1 is $C_{1-3}$ alkyl or halogen, and a is 0, 1, or 2; wherein the CNS disease is Parkinson's disease, Alzheimer's disease, dementia, Huntington's disease, amyotrophic lateral sclerosis, or acute pain.

13. The method of claim 12, wherein subject is administered with the lithium benzoate compound at about 5 to about 150 mg/kg.

14. The method of claim 12, wherein the lithium benzoate compound is administered by a systemic route.

15. The method of claim 14, wherein the systemic route is oral administration or parenteral administration.

16. The method of claim 12, wherein the subject is administered with the lithium benzoate compound at a frequency of four times a day to one time a month.

17. The method of claim 12, wherein the subject is on another CNS disease treatment or another anti-pain treatment.

18. The method of claim 12, wherein the compound is lithium benzoate.

19. The method of claim 12, wherein the solid composition further comprises a lubricant excipient.

20. The method of claim 19, wherein the lubricant excipient is sodium lauryl sulfate, magnesium stearate, talc, calcium stearate, or polyethylene glycol.

21. The method of claim 20, wherein the lubricant excipient is sodium lauryl sulfate or magnesium stearate.

22. The method of claim 1, wherein the subject has a mitochondrial dysfunction-induced central nervous system disease (CNS).

* * * * *